(12) United States Patent
Kalmeta

(10) Patent No.: US 11,938,171 B2
(45) Date of Patent: *Mar. 26, 2024

(54) THERAPEUTIC SYSTEMS, DEVICES, AND COMPOSITIONS WITH WOUND HEALING AND TISSUE REGENERATIVE PROPERTIES, USES THEREOF, AND CORRESPONDING METHODS

(71) Applicant: BIOREGENTECH, INC., Irvine, CA (US)

(72) Inventor: Margaret V. Kalmeta, Irvine, CA (US)

(73) Assignee: THE BIOREGENTECH INSTITUTE, INC., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/545,178

(22) Filed: Dec. 8, 2021

(65) Prior Publication Data

US 2022/0096605 A1 Mar. 31, 2022

Related U.S. Application Data

(63) Continuation of application No. 16/989,808, filed on Aug. 10, 2020.

(60) Provisional application No. 62/992,579, filed on Mar. 20, 2020, provisional application No. 62/885,761, filed on Aug. 12, 2019.

(51) Int. Cl.

| | |
|---|---|
| *A61K 38/39* | (2006.01) |
| *A61K 31/7004* | (2006.01) |
| *A61K 31/728* | (2006.01) |
| *A61K 33/26* | (2006.01) |
| *A61K 33/34* | (2006.01) |
| *A61N 5/06* | (2006.01) |
| *A61N 5/067* | (2006.01) |
| *G06T 7/00* | (2017.01) |
| *H01S 3/067* | (2006.01) |

(52) U.S. Cl.
CPC .......... *A61K 38/39* (2013.01); *A61K 31/7004* (2013.01); *A61K 31/728* (2013.01); *A61K 33/26* (2013.01); *A61K 33/34* (2013.01); *A61N 5/06* (2013.01); *G06T 7/0012* (2013.01); *H01S 3/06708* (2013.01); *A61N 2005/0632* (2013.01); *A61N 2005/0652* (2013.01); *A61N 5/067* (2021.08); *G06T 2207/20212* (2013.01); *G06T 2207/30088* (2013.01)

(58) Field of Classification Search
CPC ....................................................... A61K 38/39
See application file for complete search history.

(56) References Cited

U.S. PATENT DOCUMENTS

| | | | | |
|---|---|---|---|---|
| 4,414,202 | A | * 11/1983 | Silvetti | A61K 31/715 514/474 |
| 4,808,570 | A | 2/1989 | Michaeli | |
| 5,196,185 | A | 3/1993 | Silver et al. | |
| 6,022,557 | A | 2/2000 | Maser | |
| 6,197,935 | B1 | * 3/2001 | Doillon | C07K 14/78 530/427 |
| 9,610,378 | B2 | * 4/2017 | Ryu | A61L 15/44 |
| 11,389,663 | B2 | * 7/2022 | Kalmeta | A61C 1/0046 |
| 2003/0008830 | A1 | * 1/2003 | Prozillo | A61K 38/39 530/356 |
| 2007/0166369 | A1 | 7/2007 | Neuberger et al. | |
| 2014/0276493 | A1 | 9/2014 | Leung et al. | |
| 2015/0209386 | A1 | * 7/2015 | Gabbay | A61K 9/7007 424/635 |
| 2015/0283287 | A1 | * 10/2015 | Agarwal | A61L 15/24 424/650 |
| 2016/0101207 | A1 | * 4/2016 | Parsons | A61L 15/46 424/618 |
| 2018/0154172 | A1 | 6/2018 | Kalmeta | |
| 2020/0188686 | A1 | * 6/2020 | Kalmeta | A61C 19/063 |
| 2021/0046163 | A1 | * 2/2021 | Kalmeta | A61K 31/7004 |

OTHER PUBLICATIONS

United States Patent and Trademark Office, Non-Final Office Action issued in U.S. Appl. No. 16/989,808, filed Dec. 13, 2022, pp. 1-11.
Chattopadhyay, "Collagen-Based Biomaterials for Wound Healing", Biopolymers, Aug. 2014; pp. 821-833, vol. 101(8).

* cited by examiner

*Primary Examiner* — Gina C Justice

(74) *Attorney, Agent, or Firm* — Pillsbury Pittman LLP (CV)

(57) ABSTRACT

Presented herein are compositions that can be administered to a subject having damaged tissue, for example a wound. The compositions are often administered in combination with administration of energy (e.g., laser energy, light from a light emitting diode, radiofrequency (RF) energy, audio frequency energy, etc.) from an energy generating device and/or system to the affected site. The compositions, systems, devices, and methods herein were found to induce wound healing and tissue regeneration.

10 Claims, 49 Drawing Sheets

*Decrease in mm value from line = increase in tissue height

Bone Densities PA Maxilla #10

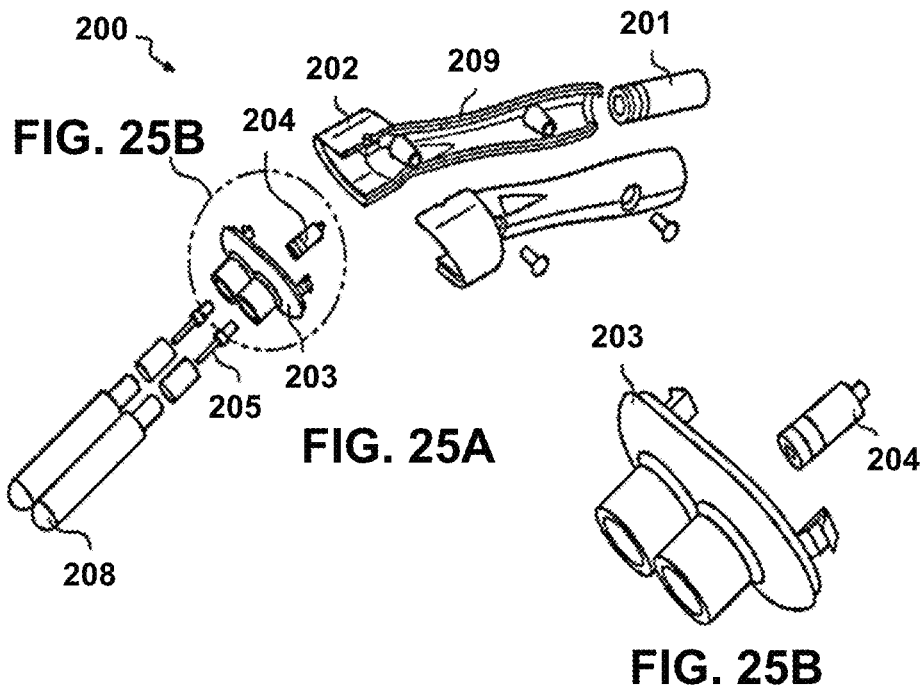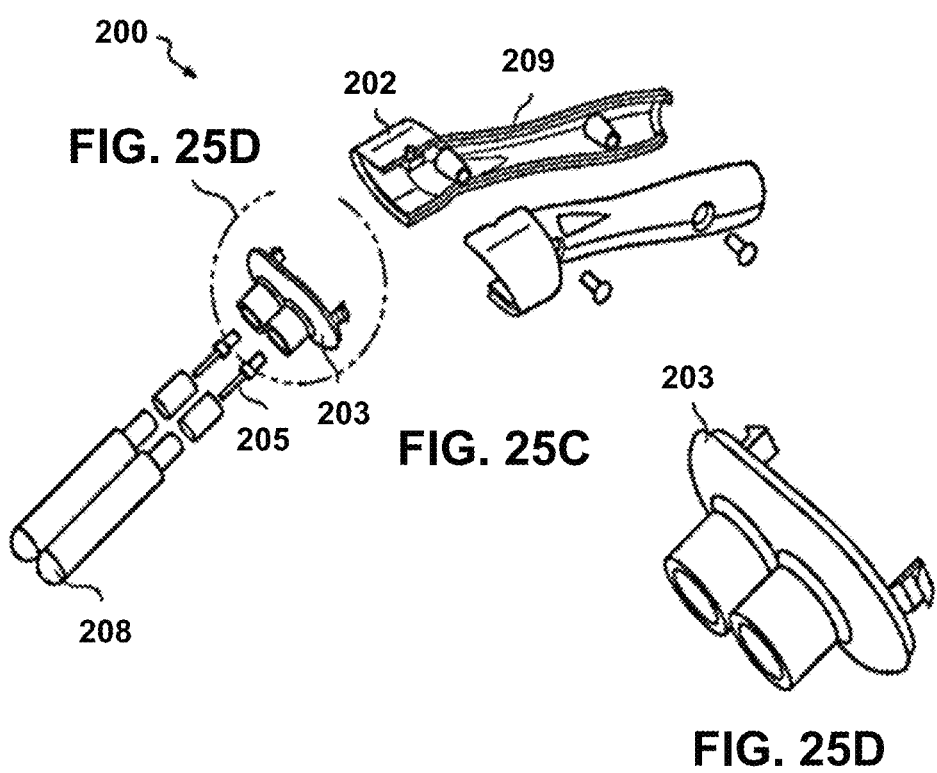

FIG. 35

ACUTE WOUNDS - *Extraction site
Substrate + Laser

| FORMULATION | SUBSTANCE ||||||||| GROWTH (D) Days/mm |||| INFECTION CONTROL ||||
|---|---|---|---|---|---|---|---|---|---|---|---|---|---|---|---|---|---|
| | HA | Fucose | Col | Cu | Au | ATP | Fe | Ag | Ach | 1 | 3 | 5 | 7 | 1 | 3 | 5 | 7 |
| 1 | X | | | | | | | | | | | | | | | | |
| 2 | X | X | | | | | | | | | | | | | | | |
| 3 | X | | | | | | | | | | | | | | | | |
| 4 | X | | | X | | | | | | | | | | | | | |
| 5 | X | | X | | | X | | | | 8 | 8 | 8 | | +++ | +++ | +++ | |
| 6 | X | X | | | X | | | X | | | | | | | | | |
| 7 | X | X | X | | | X | | | X | 8 | 8 | 8 | | +++ | +++ | +++ | |
| 8 | X | X | | | | | | | X | | | | | | | | |
| 9 | X | | | | | | | | | | | | | | | | |
| 10 | X | X | | | | | X | | | | | | | | | | |
| 11 | X | | | | | | | | | | | | | | | | |
| 12 | X | X | X | | | X | | X | | 8 | 8 | 8 | | +++ | +++ | +++ | |
| 13 | X | | | | | | | | | | | | | | | | |
| 14 | | | | | | | | | | | | | | | | | |
| 15 | | | | | | | | | | | | | | | | | |
| 16 | X | | X | X | X | X | X | | | 9 | 9 | 9 | | +++ | +++ | +++ | |
| 17 | X | | X | X | X | X | X | | | 9 | 9 | 9 | | +++ | +++ | +++ | |
| 18 | X | | X | X | X | X | X | X | | 9 | 9 | 9 | | +++ | +++ | +++ | |
| 19 | | | X | X | X | | | | | | | | | | | | |
| 20 | | | | | | | | X | | | | | | | | | |
| 21 | X | X | X | X | | | | | | | | | | | | | |
| 22 | X | | X | | | | | | | 9 | 9 | 9 | | +++ | +++ | +++ | |
| 23 | X | | X | | | | | | | 9 | 9 | 9 | | +++ | +++ | +++ | |

FIG. 36

ACUTE WOUNDS - *leg wounds
Substrate Alone

| FORMULATION | SUBSTANCE | | | | | | | | | | GROWTH (l) Days/mm | | | | INFECTION CONTROL | | | |
|---|---|---|---|---|---|---|---|---|---|---|---|---|---|---|---|---|---|---|
| | HA | Fucose | Col | Cu | Au | ATP | Fe | Ag | Ach | | 1 | 3 | 5 | 7 | 1 | 3 | 5 | 7 |
| 1 | X | | | | | | | | | | | | | | | | | |
| 2 | X | X | | | | | | | | | | | | | | | | |
| 3 | X | | X | | | | | | | | | | | | | | | |
| 4 | X | | | | | | | | | | | | | | | | | |
| 5 | X | | | | | | | | | | | | | | | | | |
| 6 | X | X | | | X | | | | | | 14 | 17 | 20 | | +++ | +++ | +++ | |
| 7 | | X | | | | X | | | | | | | | | | | | |
| 8 | X | | | | | | | | | | | | | | | | | |
| 9 | X | X | | X | | X | | | X | | | | | | | | | |
| 10 | X | X | | | | | X | | X | | 11 | 13 | 15 | | +++ | +++ | +++ | |
| 11 | X | X | | | | | | | | | | | | | | | | |
| 12 | X | X | X | | | | | | | | | | | | | | | |
| 13 | X | | X | X | X | X | | X | | | | | | | | | | |
| 14 | X | | X | | | | | | | | | | | | | | | |
| 15 | X | | X | X | X | X | X | | | | 21 | 23 | 27 | | +++ | +++ | +++ | |
| 16 | | | X | X | X | X | X | | | | 14 | 17 | 17 | | +++ | +++ | +++ | |
| 17 | | | X | X | X | X | X | | | | 42 | 50 | 55 | | +++ | +++ | +++ | |
| 18 | | | X | X | X | X | | | | | | | | | | | | |
| 19 | X | | X | | | X | X | X | | | | | | | | | | |
| 20 | X | | X | X | | X | | X | | | 9 | 12 | 13 | | +++ | +++ | +++ | |
| 21 | | X | X | X | | | | | | | 13 | 17 | 17 | | +++ | +++ | +++ | |
| 22 | | | X | | | | | | | | | | | | | | | |
| 23 | | | X | | | | | | | | | | | | | | | |

FIG. 37

ACUTE WOUNDS - *leg wounds*
Substrate + LASER

| FORMULATION | SUBSTANCE | | | | | | | | | GROWTH (Days/mm) | | | | INFECTION CONTROL | | | |
|---|---|---|---|---|---|---|---|---|---|---|---|---|---|---|---|---|---|
| | HA | Fucose | Col | Cu | Au | ATP | Fe | Ag | Ach | 1 | 3 | 5 | 7 | 1 | 3 | 5 | 7 |
| 1 | X | | | | | | | | | | | | | | | | |
| 2 | X | X | | | | | | | | | | | | | | | |
| 3 | X | | | X | | | | | | | | | | | | | |
| 4 | X | | | | | | X | | | | | | | | | | |
| 5 | X | | | | X | | | | | | | | | | | | |
| 6 | X | | | | | | | X | | 42 | 48 | 55 | | +++ | +++ | +++ | |
| 7 | | | X | | | X | | | X | | | | | | | | |
| 8 | X | X | | | | | | | | | | | | | | | |
| 9 | X | X | X | | | | | | X | | | | | | | | |
| 10 | X | X | X | | | | X | | | | | | | | | | |
| 11 | X | X | | | | | | | | 59 | 85 | 72 | | +++ | +++ | +++ | |
| 12 | X | | X | X | | X | X | X | | | | | | | | | |
| 13 | X | | | | | | X | | | | | | | | | | |
| 14 | | | X | X | X | X | X | X | | 42 | 46 | 50 | | +++ | +++ | +++ | |
| 15 | X | | X | X | X | X | X | X | | 30 | 46 | 60 | | +++ | +++ | +++ | |
| 16 | X | | X | X | X | X | X | | | 39 | 44 | 60 | | +++ | +++ | +++ | |
| 17 | X | | X | X | X | X | | | | | | | | | | | |
| 18 | X | | X | X | X | | | | | | | | | | | | |
| 19 | | X | X | X | | X | | X | | | | | | | | | |
| 20 | | | X | X | X | X | | X | | 24 | 30 | 40 | | +++ | +++ | +++ | |
| 21 | | | X | X | X | X | | | | 29 | 39 | 44 | | +++ | +++ | +++ | |
| 22 | | | X | X | | | | | | | | | | | | | |
| 23 | | | X | | | | | | | | | | | | | | |

FIG. 38

ACUTE WOUNDS
LASER ALONE

| FIRMNESS | Days/mm GROWTH (D) | | | | INFECTION CONTROL D | | | | |
|---|---|---|---|---|---|---|---|---|---|
| | | 1 | 3 | 5 | 7 | 1 | 3 | 5 | 7 |
| No Change | | 1 | 3 | 4 | 6 | ++ | ++ | +++ | ++ |
| | | 2 | 3 | 5 | 8 | ++ | ++ | ++ | ++ |
| | | | | | | | | | |
| | | 2 | 5 | 9 | | ++ | ++ | +++ | Leg Wounds* |
| | | 3 | 4 | 12 | | ++ | ++ | ++ | |

Extraction* Site

FIG. 39

ACUTE WOUNDS -
LASER, Rf and Substrate

| FORMULATION | SUBSTANCE | | | | | | | | | GROWTH (Days) Days/mm | | | INFECTION | | | FIRMNESS | | |
|---|---|---|---|---|---|---|---|---|---|---|---|---|---|---|---|---|---|---|
| | HA | Fucose | Col | Cu | Au | ATP | Fe | Ag | Ach | 1 | 3 | 5 | 1 | 3 | 5 | 1 | 3 | 5 |
| 1 | X | | | | | | | | | 6 | 21 | 23 | + | + | | | | |
| 2 | X | X | | X | | | | | | 25 | 54 | 66 | ++ | ++ | ++ | ++ | ++ | +++ |
| 3 | X | | | | | | | | | 15 | 19 | 23 | +++ | +++ | +++ | | ++++ | +++++ |
| 4 | X | | | | | | X | | | 3 | 9 | 10 | + | + | + | | | + |
| 5 | X | | X | | | | | X | | 6 | 8 | 8 | +++ | +++ | +++ | ++++++ | ++++++ | +++++ |
| 6 | X | | | | X | | | | | 9 | 21 | 29 | ++ | ++ | ++ | ++++ | ++++++ | ++++++ |
| 7 | X | | X | | | | | | | 6 | 10 | 12 | + | + | + | | | |
| 8 | X | | | | | X | | | X | 20 | 14 | 29 | + | ++ | ++ | | | + |
| 9 | X | | | | | | | | X | 26 | 36 | 40 | + | ++ | ++ | | ++ | + |
| 10 | X | X | | | | | | | | 24 | 32 | 36 | +++ | +++ | +++ | ++ | +++ | +++++ |
| 11 | X | X | | X | | X | | | X | 19 | 24 | 26 | +++ | +++ | +++ | ++ | +++ | +++ |
| 12 | X | X | | | | | | | | 10 | 18 | 27 | +++ | ++++ | ++++ | ++++++ | +++++ | ++++++ |
| 13 | X | X | | | | | X | | | 15 | 19 | 24 | ++ | +++ | ++ | +++++ | +++++ | +++++ |
| 14 | X | X | | | | | | X | | 6 | 9 | 12 | +++ | +++ | +++ | +++++ | +++++ | +++++ |
| 15 | X | | | | X | | | | | 20 | 29 | 35 | ++++ | ++++ | ++++ | +++++ | +++++ | ++++++ |
| 16 | X | | X | X | X | X | | | | 24 | 32 | 39 | ++++ | ++++ | +++++ | ++++++ | ++++++ | ++++++ |
| 17 | X | | X | X | X | X | X | | | 30 | 42 | 49 | ++++ | ++++ | ++++ | ++++++ | ++++++ | ++++++ |
| 18 | X | | X | X | X | X | X | X | | 55 | 63 | 76 | ++++ | ++++ | ++++ | +++++ | ++++++ | ++++++ |
| 19 | X | | X | X | X | X | X | X | | 48 | 59 | 65 | ++++ | ++++ | ++++ | +++++ | +++++ | ++++++ |
| 20 | X | X | | | | X | X | X | | 40 | 54 | 68 | ++ | ++ | +++ | +++++ | ++++++ | +++++ |
| 21 | X | X | | | | | X | X | | 61 | 78 | 88 | ++ | ++ | ++++ | +++++ | +++++ | +++++ |
| 22 | X | X | | | | | | | | 1 | 3 | 4 | | | | | | |
| 23 | X | | X | | | | | | | 4 | 7 | 10 | ++ | ++ | +++ | | | |

FIG. 40

ACUTE WOUNDS -
Substrate Alone

*Salts* Only Salt Data*

| FORMULATION | SUBSTANCE ||||||||| GROWTH (D) ||| Days/MM's ||||||
|---|---|---|---|---|---|---|---|---|---|---|---|---|---|---|---|---|---|
| | HA | Fucose | Col | Cu | Au | ATP | Fe | Ag | Ach | 1 | 3 | 5 | \multicolumn{3}{c|}{INCREASED FIRMNESS} | \multicolumn{3}{c|}{INFECTION CONTROL} |

| FORMULATION | HA | Fucose | Col | Cu | Au | ATP | Fe | Ag | Ach | G1 | G3 | G5 | IF Day 1 | IF Day 3 | IF Day 5 | IC Day 1 | IC Day 2 | IC Day 3 |
|---|---|---|---|---|---|---|---|---|---|---|---|---|---|---|---|---|---|---|
| 1 | X | | | | | | | | | | | | | | | | | |
| 2 | X | X | | | | | | | | 14 | 19 | 22 | | | | + | ++ | +++ |
| 3 | X | | | X | | | | | | 4 | 10 | 12 | | | | ++ | +++ | +++++ |
| 4 | X | X | | | | | X | | | 3 | 8 | 10 | + | | +++ | +++++ | +++++ | +++++ |
| 5 | X | X | | | | | | | | 2 | 9 | 16 | | | + | ++ | +++++ | +++++ |
| 6 | X | | | | X | | | | | | | | | | | | | |
| 7 | X | | X | | | | | | | | | | | | | | | + |
| 8 | X | | | | | X | | | | | | | | | | | | + |
| 9 | X | X | | | | | | | X | | | | | | | + | ++ | +++ |
| 10 | X | X | | | | X | | | | | | | | | | + | ++ | +++ |
| 11 | X | X | | | | | | | X | | | | | | | | | |
| 12 | X | X | | X | | | | | | 3 | 7 | 19 | + | ++ | ++ | ++ | +++ | +++++ |
| 13 | X | X | | | | | X | | | | | | | | | +++++ | +++++ | +++++ |
| 14 | X | X | | | | | | | | | | | | | | +++++ | +++++ | +++++ |
| 15 | X | X | | | | | | | | | | | | | | +++++ | +++++ | +++++ |
| 16 | X | | | X | X | | | | | 9 | 20 | 30 | | | | +++++ | +++++ | +++++ |
| 17 | X | | X | X | X | X | | | | 8 | 19 | 42 | | ++ | | +++++ | +++++ | +++++ |
| 18 | X | | X | X | X | X | | | | 13 | 20 | 29 | ++ | ++ | +++ | +++++ | +++++ | +++++ |
| 19 | X | | X | X | X | X | | | | 20 | 32 | 60 | + | + | ++ | +++++ | +++++ | +++++ |
| 20 | X | | X | X | X | X | X | X | | 22 | 40 | 65 | ++ | | ++ | +++++ | +++++ | +++++ |
| 21 | X | X | | X | X | X | X | X | | 29 | 44 | 72 | | | | +++++ | +++++ | +++++ |
| 22 | | X | | | | | | X | | 44 | 59 | 82 | | | | | | |
| 23 | | | X | | | | | | | | | | | | | | | |

FIG. 41

CHRONIC WOUNDS
Substrate Alone

| FORMULATION | SUBSTANCE | | | | | | | | | GROWTH (mm) | | | INCREASED FIRMNESS (%) | | | INFECTION CONTROL | | |
|---|---|---|---|---|---|---|---|---|---|---|---|---|---|---|---|---|---|---|
| | HA | Fucose | Cbl | Cu | Au | ATP | Fe | Ag | ACh | Day 7 | Day 21 | Day 35 | Day 7 | Day 21 | Day 35 | Day 7 | Day 21 | Day 35 |
| 1 | X | | | | | | | | | 1 | 2 | 5 | | | | | | |
| 2 | X | X | | | | | | | | 7 | 15 | 30 | | | | + | ++ | +++ |
| 3 | X | | | X | | | | | | 4 | 10 | 28 | | | | | | + |
| 4 | X | | | | | | X | | | 1 | 2 | 2 | + | ++ | +++ | | | |
| 5 | X | | | | | | | X | | 1 | 3 | 6 | | | | +++++ | +++++ | +++++ |
| 6 | X | | | | X | | | | | 3 | 5 | 20 | | | + | ++ | +++++ | +++++ |
| 7 | X | | X | | | | | | | 2 | 5 | 8 | | | | | | + |
| 8 | X | | | | | X | | | | 2 | 5 | 12 | | | | | | + |
| 9 | X | | | | | | | | X | 1 | 4 | 10 | | | | | | +++ |
| 10 | X | X | | | | X | | | | 7 | 18 | 40 | | | | + | ++ | +++ |
| 11 | X | X | | X | | | | | X | 6 | 10 | 35 | | | | + | ++ | +++ |
| 12 | X | X | | | | | X | | | 20 | 30 | 60 | | | | ++++ | +++++ | +++++ |
| 13 | X | X | | | | | | X | | 4 | 8 | 25 | + | ++ | +++ | ++ | ++ | +++ |
| 14 | X | X | | | | | | | | 5 | 10 | 19 | | | | +++++ | +++++ | +++++ |
| 15 | X | | | | X | | | | | 10 | 25 | 40 | | | | +++++ | +++++ | +++++ |
| 16 | X | | X | X | X | X | | | | 10 | 22 | 52 | | | | +++++ | +++++ | +++++ |
| 17 | X | | X | X | X | X | X | | | 15 | 30 | 59 | | ++ | | +++++ | +++++ | +++++ |
| 18 | X | | X | X | X | X | X | X | | 19 | 40 | 65 | ++ | ++ | +++ | +++++ | +++++ | +++++ |
| 19 | X | | X | X | X | X | X | X | X | 25 | 42 | 70 | + | + | ++ | +++++ | +++++ | +++++ |
| 20 | X | X | | | | | | | | 29 | 46 | 84 | ++ | ++ | +++ | +++++ | +++++ | +++++ |
| 21 | X | X | | | | | | | | 50 | 69 | 119 | | | | +++++ | +++++ | +++++ |
| 22 | | | | | | | | | | 1 | 2 | 4 | | | | | | |
| 23 | | | X | | | | | | | 0 | 0 | 2 | | | | | | |

FIG. 42

CHRONIC WOUNDS
Substrate With Laser

| FORMULATION | SUBSTANCE | | | | | | | | | GROWTH (mm) | | | INCREASED FIRMNESS (%) | | | INFECTION CONTROL | | |
|---|---|---|---|---|---|---|---|---|---|---|---|---|---|---|---|---|---|---|
| | HA | Fucose | Col | Cu | Au | ATP | Fe | Ag | ACh | Day 7 | Day 21 | Day 35 | Day 7 | Day 21 | Day 35 | Day 7 | Day 21 | Day 35 |
| 1 | X | | | | | | | | | 5 | 7 | 10 | | | | | | |
| 2 | X | X | | X | | | | | | 20 | 42 | 76 | +++++ | +++++ | +++++ | + | ++ | +++ |
| 3 | X | | | | | | | | | 25 | 46 | 81 | | | | ++ | ++++ | +++++ |
| 4 | X | | | | | | X | | | 1 | 3 | 4 | | | | | | |
| 5 | X | | | | | | | X | | 2 | 5 | 8 | | | | | | |
| 6 | X | | | | X | | | | | 10 | 29 | 52 | | + | ++ | +++++ | +++++ | +++++ |
| 7 | X | | X | | | | | | | 6 | 12 | 19 | | | | ++ | ++ | ++ |
| 8 | X | | | | | X | | | | 15 | 19 | 27 | | | | ++ | ++ | ++ |
| 9 | X | | | | | | | | X | 13 | 15 | 22 | | | | ++ | ++ | ++ |
| 10 | X | X | | | | | | | | 19 | 28 | 32 | | | | + | ++ | +++ |
| 11 | X | X | | | | | | | X | 16 | 24 | 27 | | | | ++ | ++ | ++ |
| 12 | X | X | | | | | | | | 30 | 44 | 67 | +++++ | +++++ | +++++ | +++++ | +++++ | +++++ |
| 13 | X | | | X | | | | | | 5 | 12 | 15 | +++++ | +++++ | +++++ | +++++ | +++++ | +++++ |
| 14 | X | | | | | | X | X | | 3 | 16 | 22 | +++++ | +++++ | +++++ | +++++ | +++++ | +++++ |
| 15 | X | | | | X | | | | | 14 | 29 | 43 | ++ | +++ | +++ | +++++ | +++++ | +++++ |
| 16 | X | | X | X | X | | | | | 22 | 49 | 62 | +++ | ++++ | ++++ | +++++ | +++++ | +++++ |
| 17 | X | | X | X | X | X | | | | 30 | 52 | 69 | +++++ | +++++ | +++++ | +++++ | +++++ | +++++ |
| 18 | X | | X | X | X | X | X | | | 34 | 58 | 74 | +++++ | +++++ | +++++ | +++++ | +++++ | +++++ |
| 19 | X | | X | X | X | X | X | | | 39 | 64 | 81 | +++++ | +++++++ | +++++ | +++++ | +++++ | +++++ |
| 20 | X | | X | X | X | X | | X | | 46 | 72 | 91 | +++++ | +++++ | +++++ | +++++ | +++++ | +++++ |
| 21 | X | X | | | X | | | X | X | 61 | 83 | 140 | +++++ | +++++ | +++++ | +++++ | +++++ | +++++ |
| 22 | | X | | | | | | | | 2 | 5 | 7 | | | | | | |
| 23 | | | X | | | | | | | 3 | 4 | 10 | | | | | | |

FIG. 43

CHRONIC WOUNDS
Substrate With RF (Audio Frequency)

| FORMULATION | SUBSTANCE | | | | | | | | | INCREASED FIRMNESS (%) | | | CIRCULATION RESTORATION | | |
|---|---|---|---|---|---|---|---|---|---|---|---|---|---|---|---|
| | HA | Fucose | Col | Cu | Au | ATP | Fe | Ag | ACh | Day 7 | Day 21 | Day 35 | Day 7 | Day 21 | Day 35 |
| 1 | X | | | | | | | | | | | | | | |
| 2 | X | X | | | | | | | | | | | + | ++ | ++++ |
| 3 | X | | | X | | | | | | | | | +++++ | +++++ | +++++ |
| 4 | X | | | | | | X | | | +++++ | +++++ | +++++ | | | |
| 5 | X | | | | | | | X | | | | | +++++ | +++++ | +++++ |
| 6 | X | | | | X | | | | | | | + | | | +++++ |
| 7 | X | | X | | | | | | | | | | | | |
| 8 | X | | | | | X | | | | | | | | | |
| 9 | | | | | | | | | X | | | | | | + |
| 10 | X | X | | | | | | | | | | | + | +++ | ++++ |
| 11 | X | X | | | | X | | | X | | | | + | +++ | +++ |
| 12 | X | X | | X | | | X | | | +++++ | +++++ | +++++ | +++++ | +++++ | +++++ |
| 13 | X | X | | | | | | | | | | | ++ | | +++ |
| 14 | | | X | | | | | | | | | | | | |
| 15 | X | X | X | | X | | | | | +++++ | +++++ | | ++++++ | ++++++ | ++++++ |
| 16 | X | | X | X | X | | | | | +++++ | +++++ | | ++++++ | ++++++ | ++++++ |
| 17 | X | | X | X | X | X | | | | +++++ | +++++ | +++++ | ++++++ | ++++++ | ++++++ |
| 18 | X | | X | X | X | X | X | | | +++++ | +++++ | +++++ | ++++++ | ++++++ | ++++++ |
| 19 | X | | X | X | X | X | X | X | | +++++ | +++++ | +++++ | ++++++ | ++++++ | ++++++ |
| 20 | X | | X | X | X | X | X | X | | +++++ | +++++ | +++++ | ++++++ | ++++++ | ++++++ |
| 21 | X | X | | | | | | | | | | | | | |
| 22 | | X | | | | | | | | | | | | | |
| 23 | | | X | | | | | | | | | | | | |

FIG. 44

CHRONIC WOUNDS
Rf (audio) Alone

| GROWTH (mm) | | | INCREASED FIRMNESS (%) | | | INFECTION CONTROL | | | CIRCULATION RESTORATION | | |
|---|---|---|---|---|---|---|---|---|---|---|---|
| Day 7 | Day 21 | Day 35 | Day 7 | Day 21 | Day 35 | Day 7 | Day 21 | Day 35 | Day 7 | Day 21 | Day 35 |
| 0 | 5 | 8 | ++ | +++ | ++++ | + | ++ | ++ | ++ | +++ | ++++ |

FIG. 45

CHRONIC WOUNDS
Substrate, Laser and Rf

| FORMULATION | SUBSTANCE | | | | | | | | |
|---|---|---|---|---|---|---|---|---|---|
| | HA | Fucose | Col | Cu | Au | ATP | Fe | Ag | ACh |
| | X | X | X | X | X | X | X | X | X |

| GROWTH (mm) | | | INCREASED FIRMNESS (%) | | | INFECTION CONTROL | | | CIRCULATION RESTORATION | | |
|---|---|---|---|---|---|---|---|---|---|---|---|
| Day 7 | Day 21 | Day 35 | Day 7 | Day 21 | Day 35 | Day 7 | Day 21 | Day 35 | Day 7 | Day 21 | Day 35 |
| 78 | 82 | 90 | +++ | ++++ | +++++ | +++ | ++++ | ++++ | +++ | ++++ | +++++ |

FIG. 46

Prophylactic Supplement

To Be tested for Antiviral Activity in the following order:
21 20 19 18 17

| FORMULATION | HA | Fucose | Col | Cu | Au | ATP | Fe | Ag | Ach | HCL |
|---|---|---|---|---|---|---|---|---|---|---|
| 1 | X | | | | | | | | | |
| 2 | X | X | | | | | | | | |
| 3 | X | | | X | | | | | | |
| 4 | X | | | | | | X | | | |
| 5 | X | | | | | | | X | | |
| 6 | X | | | | X | | | | | |
| 7 | X | | X | | | | | | | |
| 8 | X | | | | | X | | | | |
| 9 | X | | | | | | | | X | |
| 10 | X | X | | | | | | | | |
| 11 | X | X | | X | | | | | X | |
| 12 | X | X | | | | X | | | | |
| 13 | X | X | | | | | X | X | | |
| 14 | X | | | | X | | | | | |
| 15 | X | | | | X | | | | | |
| 16 | X | | X | X | X | | | | | |
| 17 | X | | X | X | X | X | | | | X |
| 18 | X | | X | X | X | X | X | | | X |
| 19 | X | | X | X | X | X | X | X | | X |
| 20 | X | X | X | X | | X | X | | | X |
| 21 | X | X | X | | | | | X | | X |
| 22 | | X | | | | | | | | |
| 23 | | | X | | | | | | | |

HCL: Only helps ←absorption

*Currently 17-21 is being used as drinkable substrate*
* 17-21 increased HRV (heart rate variability) thus far

FIG. 47

THERAPEUTIC SYSTEMS, DEVICES, AND COMPOSITIONS WITH WOUND HEALING AND TISSUE REGENERATIVE PROPERTIES, USES THEREOF, AND CORRESPONDING METHODS

CROSS-REFERENCE TO RELATED APPLICATIONS

This application is a continuation of U.S. patent application Ser. No. 16/989,808, filed Aug. 10, 2020, which claims priority to U.S. provisional patent application 62/885,761, filed Aug. 12, 2019, and U.S. provisional patent application 62/992,579, filed Mar. 20, 2020, the entire contents of each of which are herein incorporated by reference in their entireties.

FIELD OF THE INVENTION

Therapeutic systems, devices, compositions, and methods are described that can be used for the treatment of damaged tissue, which methods include, in some embodiments, administration of a therapeutic composition, with or without application of additional energy (e.g., laser energy, light from a light emitting diode, radiofrequency (RF) energy, audio frequency energy, etc.), to a damaged tissue.

BACKGROUND

Wound healing systems are known. Typically such systems deliver high energy radiation to tissue to weld the tissue together and/or provide an adhesive configured to join different portions of skin together.

SUMMARY

In certain aspects, provided herein are compositions comprising two or more of: collagen, hyaluronic acid, fucose, copper, and iron. In some embodiments, the compositions here are used to treat wounds or tissue damage.

In some aspects, provided herein are systems for treating wounds or tissue damage. In some embodiments, the systems comprise one or more energy sources and/or devices, one or more of the compositions described herein, an imaging device, and/or other components.

In some aspects, provided herein are methods of treating wounds or tissue damage. In some embodiments, the methods comprise administering a therapeutically effective amount of a composition described herein to the wound or damaged tissue and/or administering a therapeutically effective amount of energy (e.g., laser energy, light from a light emitting diode, radiofrequency (RF) energy, audio frequency energy, etc.) to the wound or damaged tissue.

In some aspects, provided herein are devices configured to generate one or more types of therapeutic energy for provision to tissue. In some embodiments, the devices comprise one or more energy sources configured to generate one or more types of therapeutic energy. The one or more types of therapeutic energy may comprise one or more of laser radiation, radio frequency (RF) waves, audio frequency waves, or light from a light emitting diode (LED).

In some aspects, provided herein are devices for imaging tissue. In some embodiments, the devices comprise one or more light emitting diodes (LED) configured to emit light for illuminating and reflecting the tissue, a camera configured to obtain images of the illuminated tissue, one or more processors configured to analyze the images, and/or other components.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 4 shows bone profile changes of a facial zygomatic arch before and after treatment with a composition comprising hyaluronic acid, iron, and copper gluconate. Cephalometric x-rays were overlaid at different points along the zygomatic arch (A, B, C, D) were measured.

FIG. 24a shows a front perspective view. FIG. 24b shows a right side view. FIG. 24c shows a bottom view.

FIG. 25a-25d show views of the example embodiment of the RF or audio device 200 with and without a laser energy source. FIG. 25a shows an exploded view of the RF or audio device with a laser. FIG. 25b shows a close-up of a housing (e.g., a handpiece) with a laser relative to the housing. FIG. 25c shows an exploded view of an RF or audio device without a laser. FIG. 25d shows a detailed view of a housing for an RF or audio device without a laser.

FIG. 27a shows a top view. FIG. 27b shows a side view. FIG. 27c shows a perspective view of the RF or audio tips. FIG. 27d shows an exploded side perspective view. FIG. 27e shows an alternative side perspective view.

FIG. 35 shows a table of results for the treatment of tooth extraction sites with the substrates (compositions) of formulas 7, 12, 16-18, 22 and 23 alone (without energy (e.g., laser energy, light from a light emitting diode, radiofrequency (RF) energy, audio frequency energy, etc.)).

FIG. 36 shows a table of results for the treatment of tooth extraction sites with the substrates (compositions) of formulas 7, 12, 16-18, 22 and 23 and treatment with energy (e.g., laser energy, light from a light emitting diode, radiofrequency (RF) energy, audio frequency energy, etc.).

FIG. 37 shows a table of results for the treatment of leg wounds with the substrates (compositions) of formulas 7, 12, 16-18, 22 and 23 alone (without energy (e.g., laser energy, light from a light emitting diode, radiofrequency (RF) energy, audio frequency energy, etc.)).

FIG. 38 shows a table of results for the treatment of leg wounds with the substrates (compositions) of formulas 7, 12, 16-18, 22 and 23 and treatment with energy (e.g., laser energy, light from a light emitting diode, radiofrequency (RF) energy, audio frequency energy, etc.).

FIG. 39 shows a table of results for the treatment of tooth extraction sites (Extraction Site) and leg wounds with energy (e.g., laser energy, light from a light emitting diode, radiofrequency (RF) energy, audio frequency energy, etc.) in the absence of a composition (e.g., a substrate).

FIG. 40 shows a table of results for the treatment of acute wounds. Oral surgery acute wounds are demarked by very small changes (e.g., 4, 5, 6, 7, 14, 22 and 23 mm) and all others are leg chronic open wounds demarked by large mm changes with the substrates (compositions) of formulas 1-23 and treatment with energy. For oral surgery: extraction/s were performed, a laser-RF or audio device (described herein) was placed over the extraction site, the unit was turned on, followed by emission through the device for 1-2 minutes. A substrate (composition) was placed into the extraction site. The laser-RF or audio device was placed over the extraction site, turned on, and emission through the device began for 1-2 minutes. The patient was allowed to keep their mouth in an open position for 2-5 minutes until clear carbon begins to form. For a chronic wound—substrate was placed onto the wound. Laser-rf wounds with emission from handpiece for 15 minutes. Optionally repeat several times until the surrounding tissue around the wound and the surface of the wound begins to firm. Wound tape was placed onto the wound. An absorbent pad was placed over the taped wound. The wound site and tissue was immobilized with sports tape.

FIG. 41 shows a table of results for the treatment of acute wounds with the substrates of formulas 1-23 alone (without energy (e.g., laser energy, light from a light emitting diode, radiofrequency (RF) energy, audio frequency energy, etc.)). In this table, the row of formulation 3 is a head wound; the row of formulation 4 is a leg wound; the rows of formulations 5, 6 and 15-18 are extractions; and the rows formulas 13 and 19-21 are oral surgery sites in the mucosa.

FIG. 42 shows a table of results for the treatment of chronic wounds with the substrates of formulas 1-23 alone (without energy (e.g., laser energy, light from a light emitting diode, radiofrequency (RF) energy, audio frequency energy, etc.)). In this table, the rows of formulas 1, 4, 5, 7 and 8 are periodontal wounds. The remaining rows are leg wounds.

FIG. 43 shows a table of results for the treatment of chronic wounds comprising chronic open leg wounds with the substrates of formulas 1-23 and treatment with energy (e.g., laser energy, light from a light emitting diode, radiofrequency (RF) energy, audio frequency energy, etc.). In this example, the energy comprises laser energy. To generate the data in FIG. 43, a substrate (composition) was placed onto wound. Laser energy was applied to the wound with laser emission from a laser device for 15 minutes. This was optionally repeated several times until the surrounding tissue around the wound and the surface of the wound began to firm. Wound tape was placed onto the wound. An absorbent pad was placed over the taped wound. The wound site was immobilized with sports tape.

FIG. 44 shows a table of results for the treatment of chronic wounds.

FIG. 45 shows a table of results for the treatment of a chronic wound comprising a chronic leg wound with RF or audio in the absence of a substrate (composition). To generate the data in the table of FIG. 45, an RF or audio device was placed over the wound with emission from the device for 15 minutes. This was optionally repeated several times until the surrounding tissue around the wound and the surface of wound began to firm. Wound tape was placed onto the wound. An absorbent pad was placed over the taped wound. The wound site and surrounding tissue was immobilized with sports tape.

FIG. 46 shows a table of results for the treatment of a chronic wound such as a chronic leg wound with the substrate (composition) of formula 21 and RF or audio. To generate the data for the table of FIG. 46, an RF or audio device was placed over the wound with emission from the device for 15 minutes. This was optionally repeated several times until the surrounding tissue around the wound and the surface of wound began to firm. Wound tape was placed onto the wound. An absorbent pad was placed over the taped wound. The wound site and surrounding tissue was immobilized with sports tape.

FIG. 47 shows a table of the composition of the substrates of formula 1-23, formulated as a liquid, to be used for prophylactic supplement.

Figure 1:
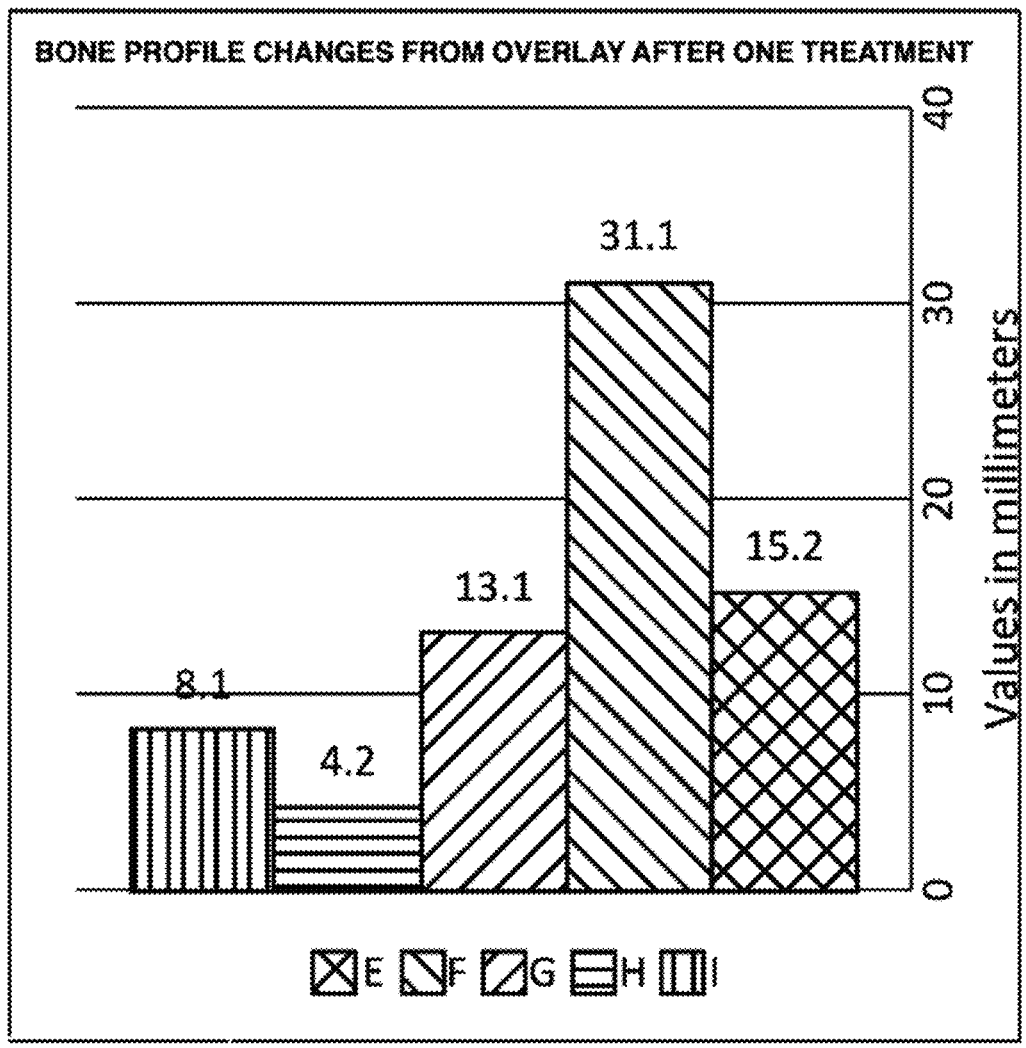
FIG. 1 shows bone profile changes for a zygomatic arch treated with a composition comprising hyaluronic acid, iron, and copper gluconate. Cephalometric x-rays were overlaid at different points along the zygomatic arch (E, F, G, H and I) were measured.
Figure 2:
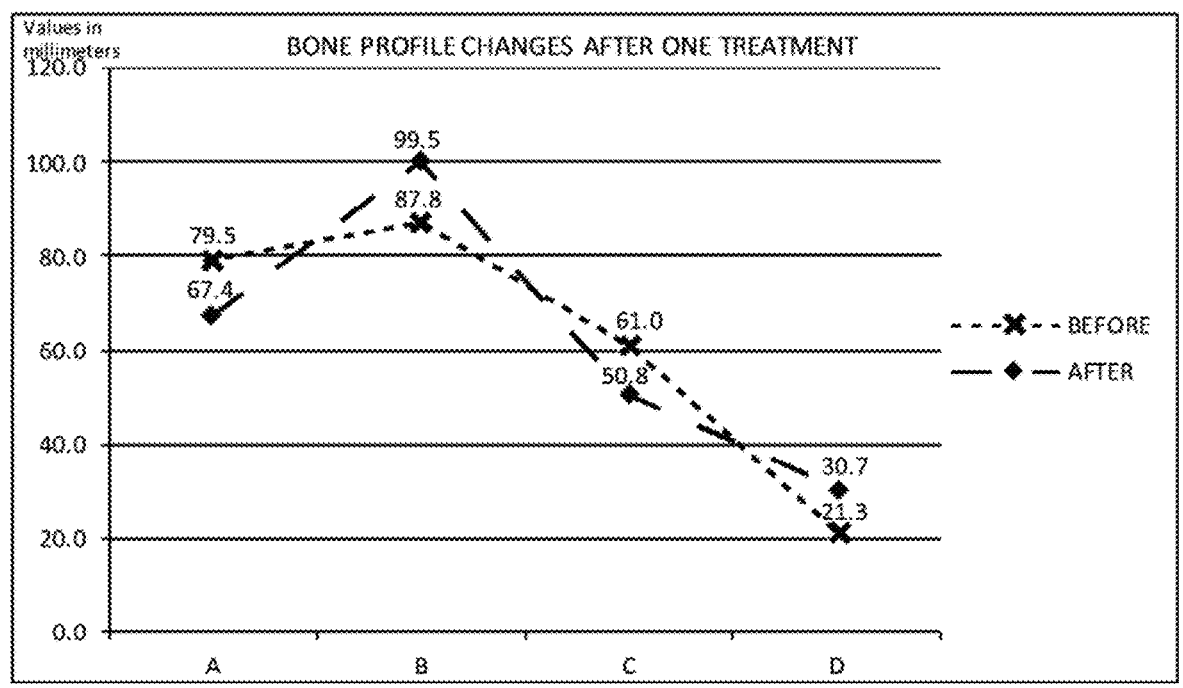
FIG. 2 shows bone profile changes of a facial zygomatic arch before and after treatment with a composition comprising hyaluronic acid, iron, and copper gluconate. Cephalometric x-rays were overlaid at different points along the zygomatic arch (A, B, C, D) were measured.
Figure 3:
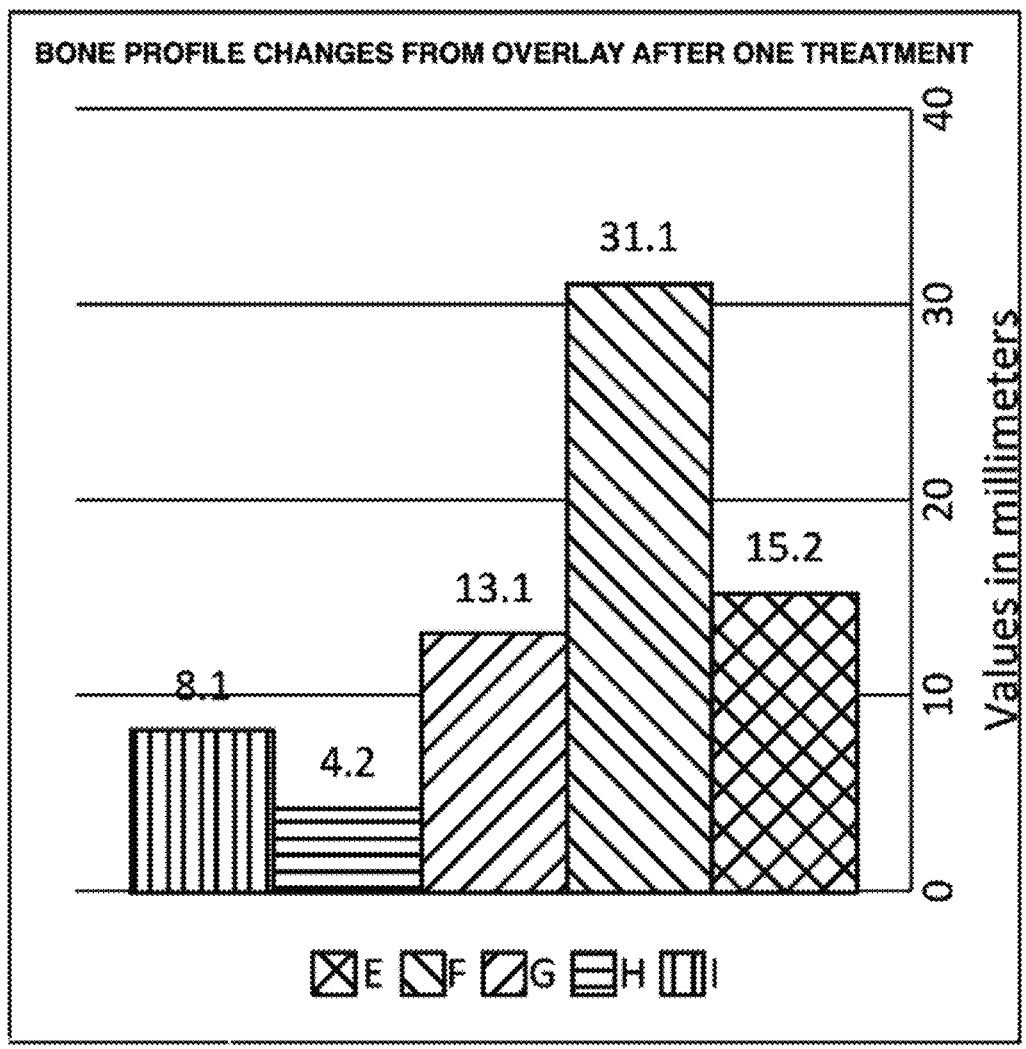
FIG. 3 shows bone profile changes for a zygomatic arch treated with a composition comprising hyaluronic acid, iron, and copper gluconate. Cephalometric x-rays were overlaid at different points along the zygomatic arch (E, F, G, H and I) were measured.
Figure 4:
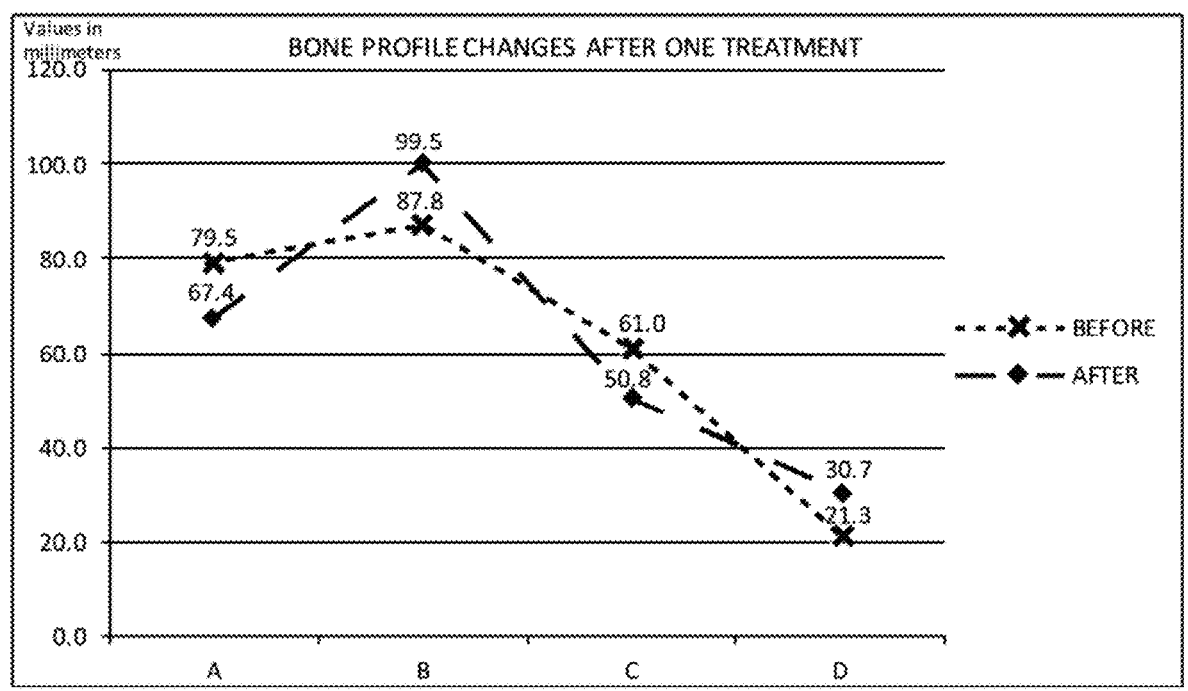
FIG. 4 shows bone profile changes.
Figure 5:
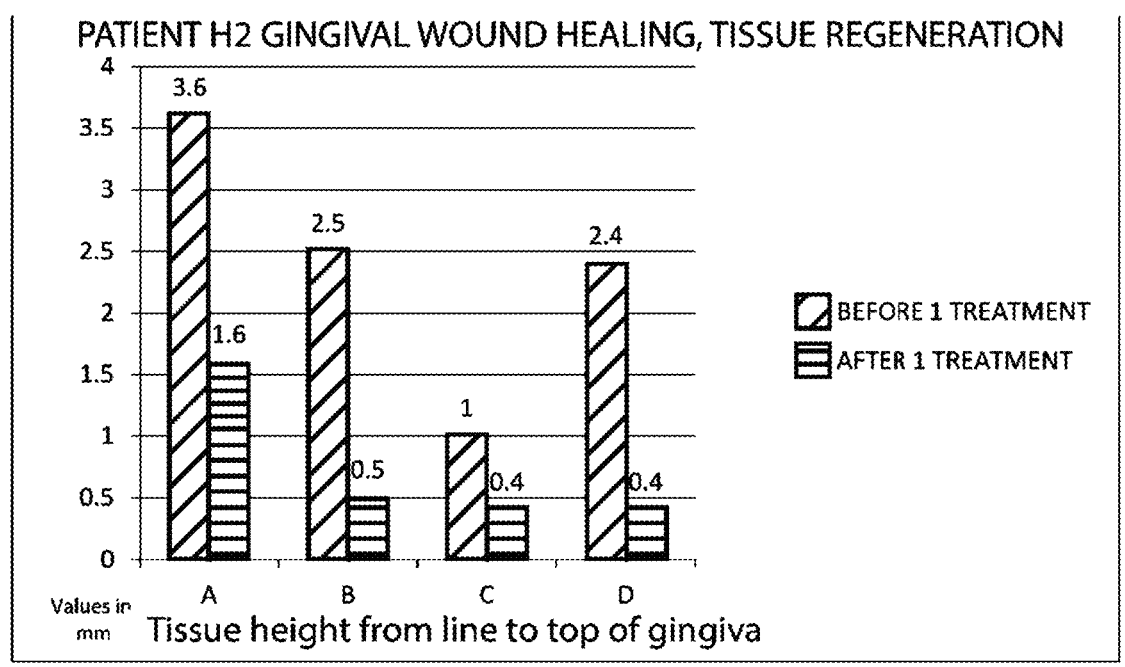
FIG. 5 shows tissue regeneration differences before (left bar of each pair) and after (right bar of each pair) treatment of maxillary anterior gingival with a composition comprising hyaluronic acid, iron, and copper gluconate. Before and after pictures were taken and anterior attached gingiva was measured along 4 points (before and after).
Figure 6:
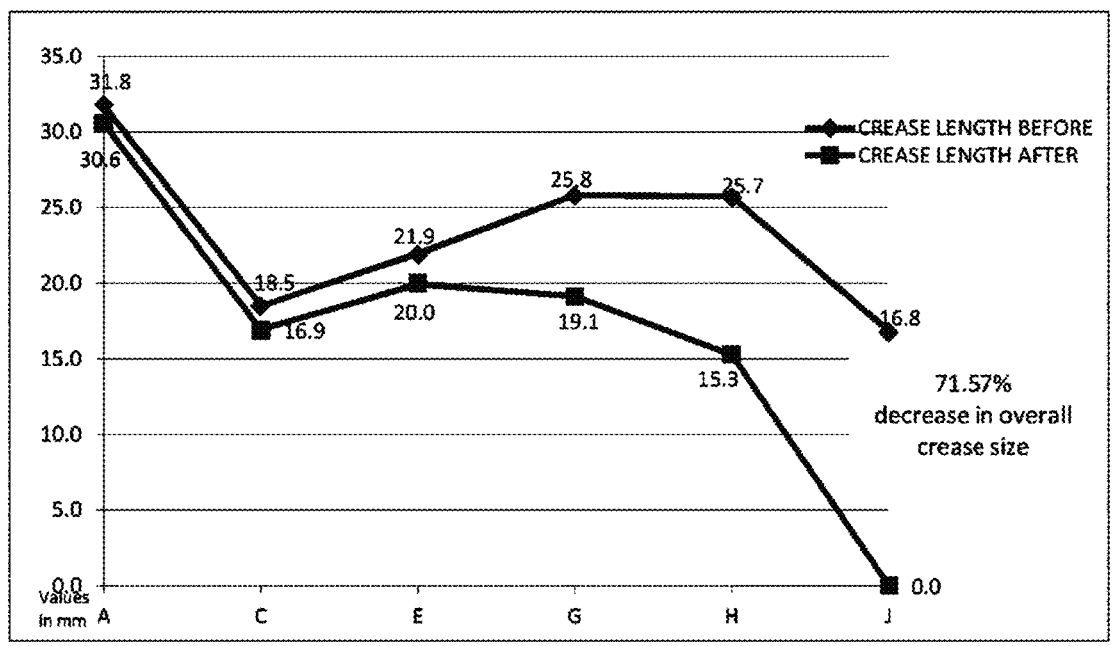
FIG. 6 shows changes in epithelium crease length before and after treatment with a composition comprising hyaluronic acid, iron, and copper gluconate. Pictures were taken of a Leg keloid scar before and after treatment and scar creases were measured along 6 points (before and after).
Figure 7:
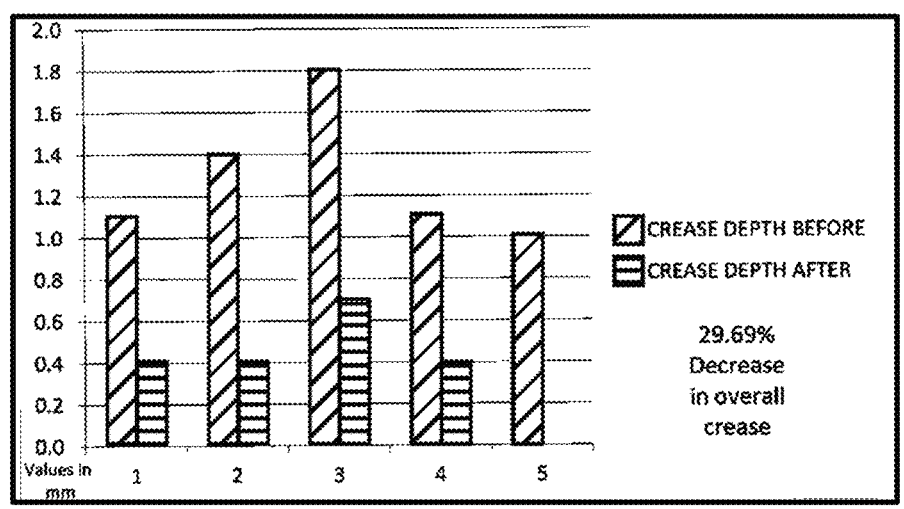
FIG. 7 shows changes in epithelium crease length before (left bar of each pair) and after (right bar of each pair) treatment with a composition comprising hyaluronic acid, iron, and copper gluconate. Pictures were taken of a Leg keloid scar before and after treatment and scar creases were measured along 5 points (before and after).
Figure 8:
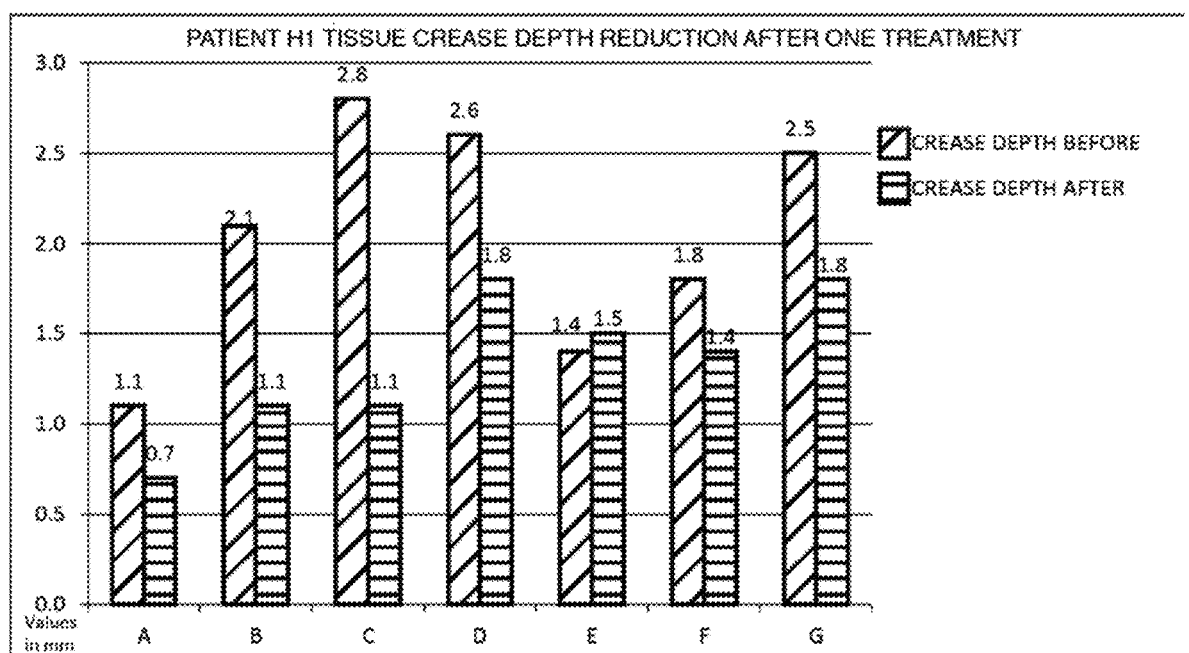
FIG. 8 shows changes in epithelium crease depth before (left bar of each pair) and after (right bar of each pair) treatment with a composition comprising hyaluronic acid, iron, and copper gluconate. Pictures were taken of a Leg keloid scar before and after treatment and scar crease depth was measured along 7 points (before and after).
Figure 9:
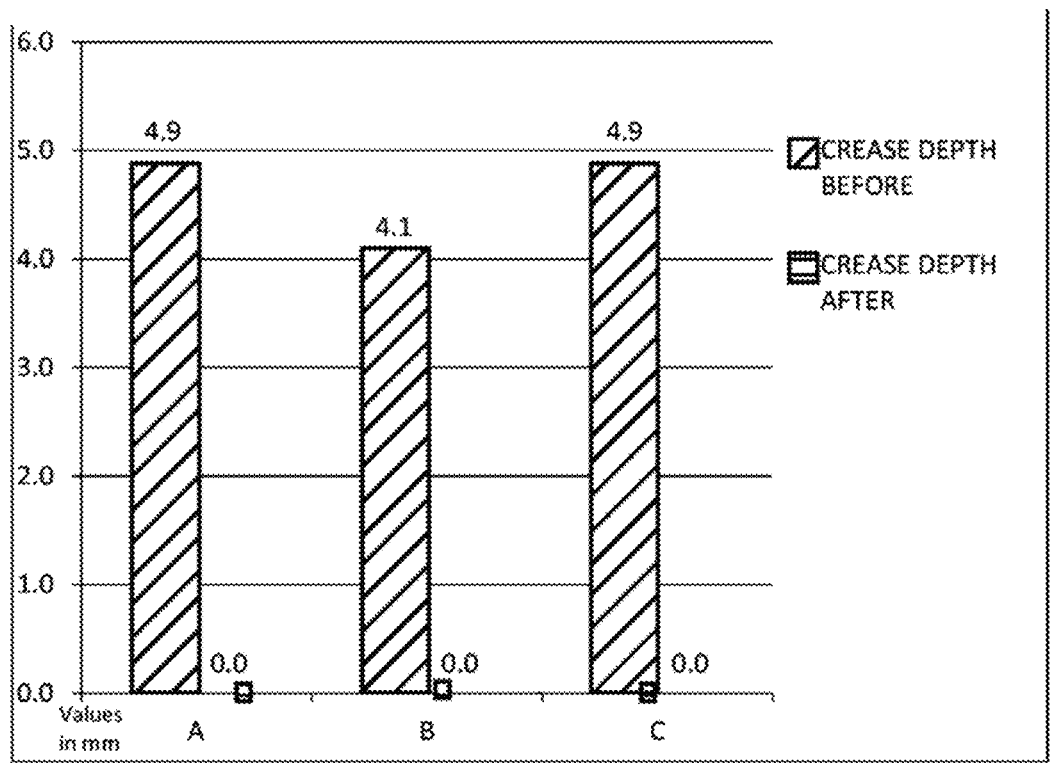
FIG. 9 shows soft tissue repair of a facial scar and shows changes in epithelium crease depth before (left bar of each pair) and after (right bar of each pair) treatment with a composition comprising hyaluronic acid, iron, and copper gluconate. Pictures were taken of the facial scar before and after treatment and scar depths were measured along 3 points (before and after).
Figure 10:
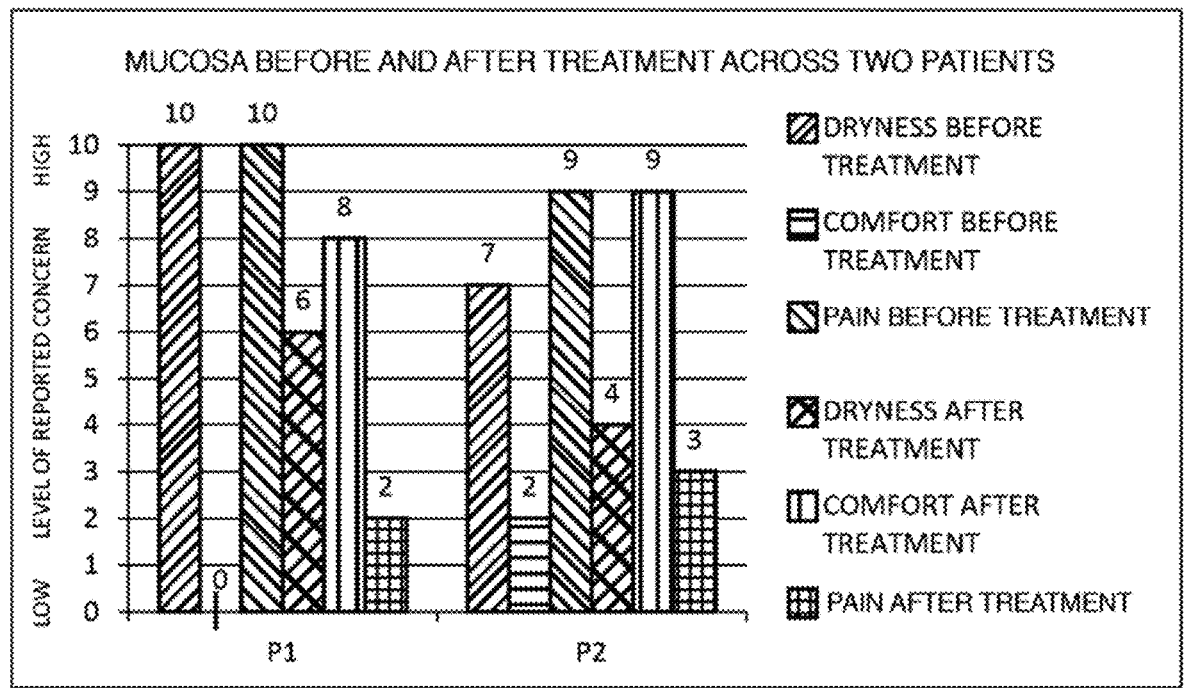
FIG. 10 shows subjective data for mucosal before and after treatment with a composition comprising hyaluronic acid, iron, and copper gluconate. Patients (P1 and P2) were given a questionnaire before (left three bars of each set) and after (right three bars of each set) treatment. The questions related to dryness (bars 1 and 4 of each set, as count from left to right), comfort (bars 2 and 5 of each set, as count from left to right) and pain (bars 3 and 6 of each set, as count from left to right).
Figure 11:
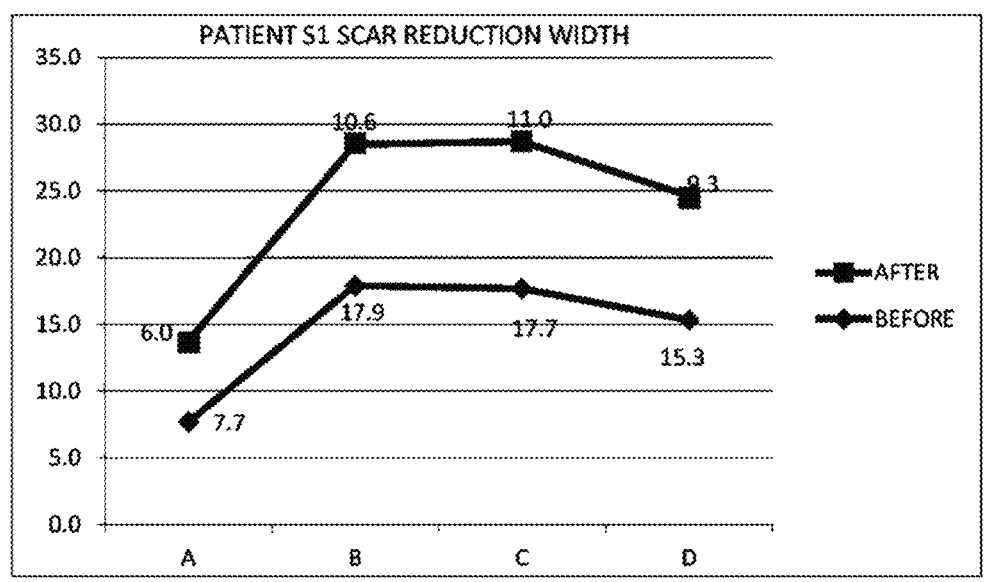
FIG. 11 shows changes in epithelium crease length and depth of a buttock scar before and after treatment with a composition comprising hyaluronic acid, iron, and copper gluconate. Pictures were taken of the buttock scar before and after treatment, and scar crease length and depth were measured along 4 points (before and after).
Figure 12:
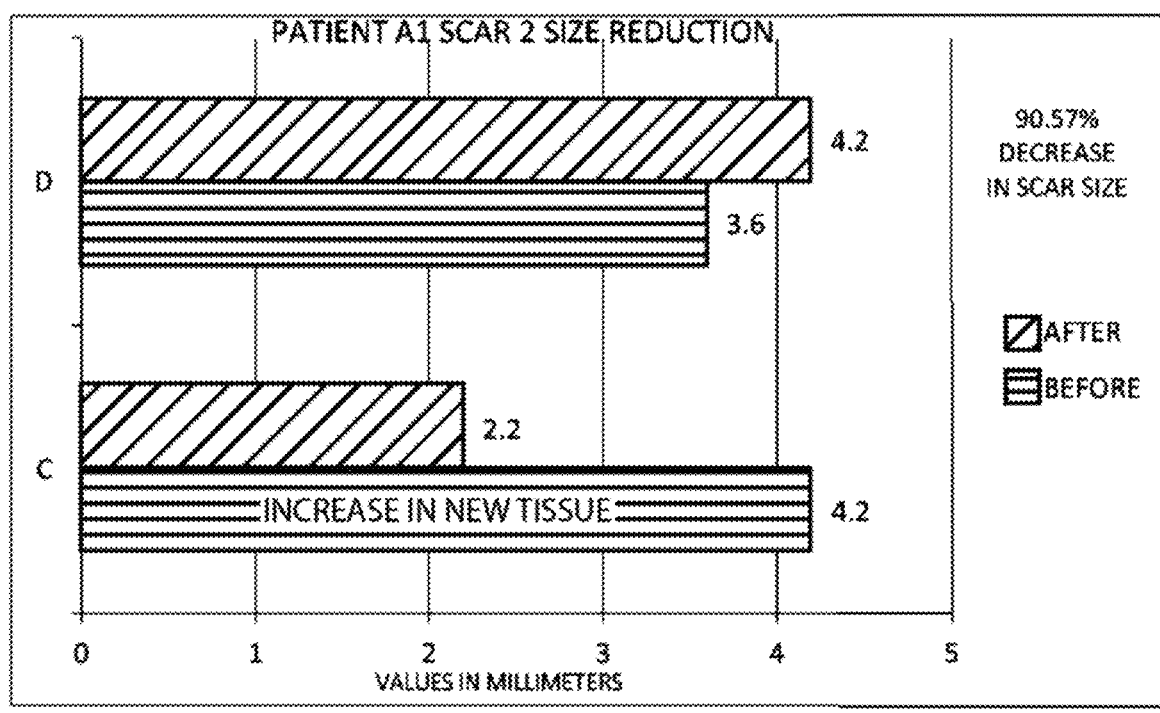
FIG. 12 shows changes in epithelium crease length of an arm scar before (bottom bar of each pair) and after (top bar of each pair) treatment with a composition comprising hyaluronic acid, iron, and copper gluconate. Pictures were taken of the arm scar before and after treatment, and scar crease length was measured along 2 points (before and after).
Figure 13:
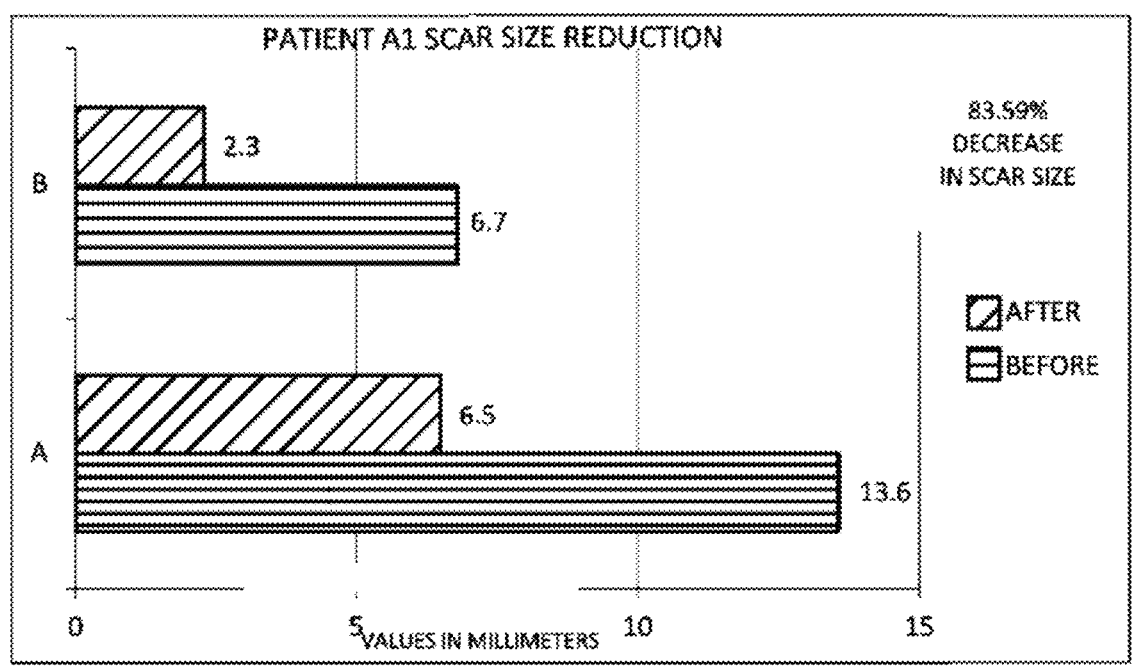
FIG. 13 shows changes in epithelium crease length of a leg scar before (bottom bar of each pair) and after (top bar of each pair) treatment with a composition comprising hyaluronic acid, iron, and copper gluconate. Pictures were taken of the leg scar before and after treatment, and scar crease length was measured along 7 points (before and after).
Figure 14:
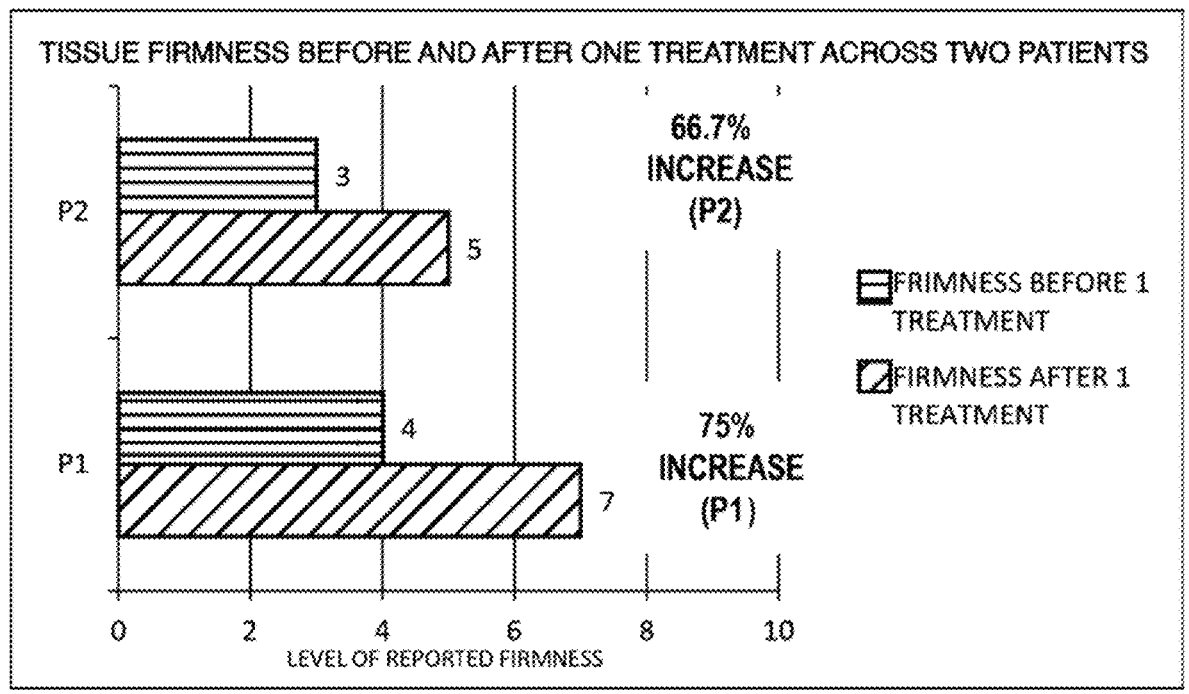
FIG. 14 shows changes in arm pit firmness before (top bar of each pair) and after (bottom bar of each pair) treatment with a composition comprising hyaluronic acid, iron, and copper gluconate. Armpit firmness was assessed by a subjective questionnaire provided before and after treatment for the two data points reported.
Figure 15:
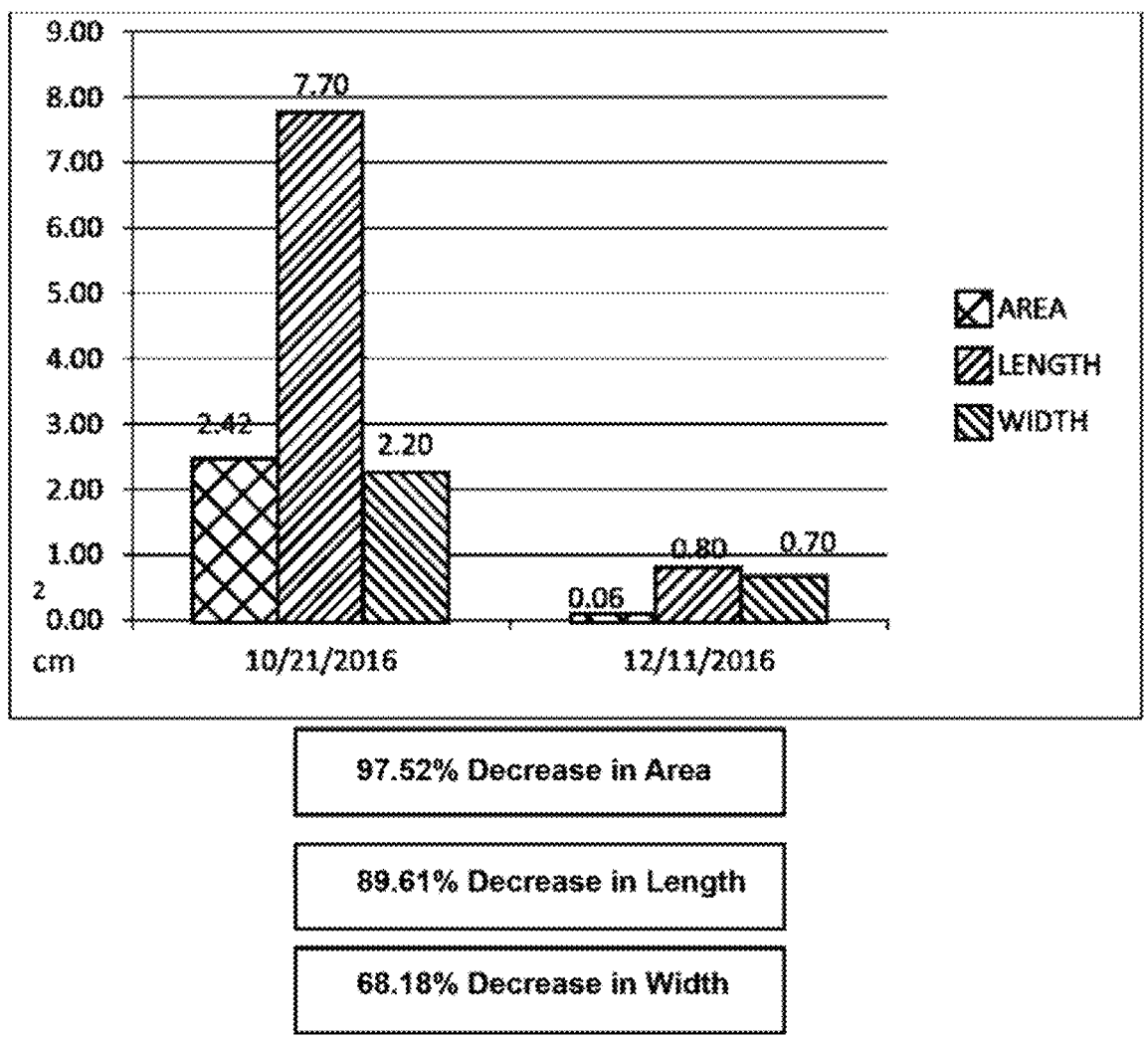
FIG. 15 shows changes in scar area (first bar of each set of three), length (second bar of each set of three) and width (third bar of each set of three) of a stomach scar before (left set of three bars) and after (right set of three bars) treatment with a composition comprising hyaluronic acid, iron, and copper gluconate. Pictures were taken of the stomach scar before and after treatment.
Figure 16:
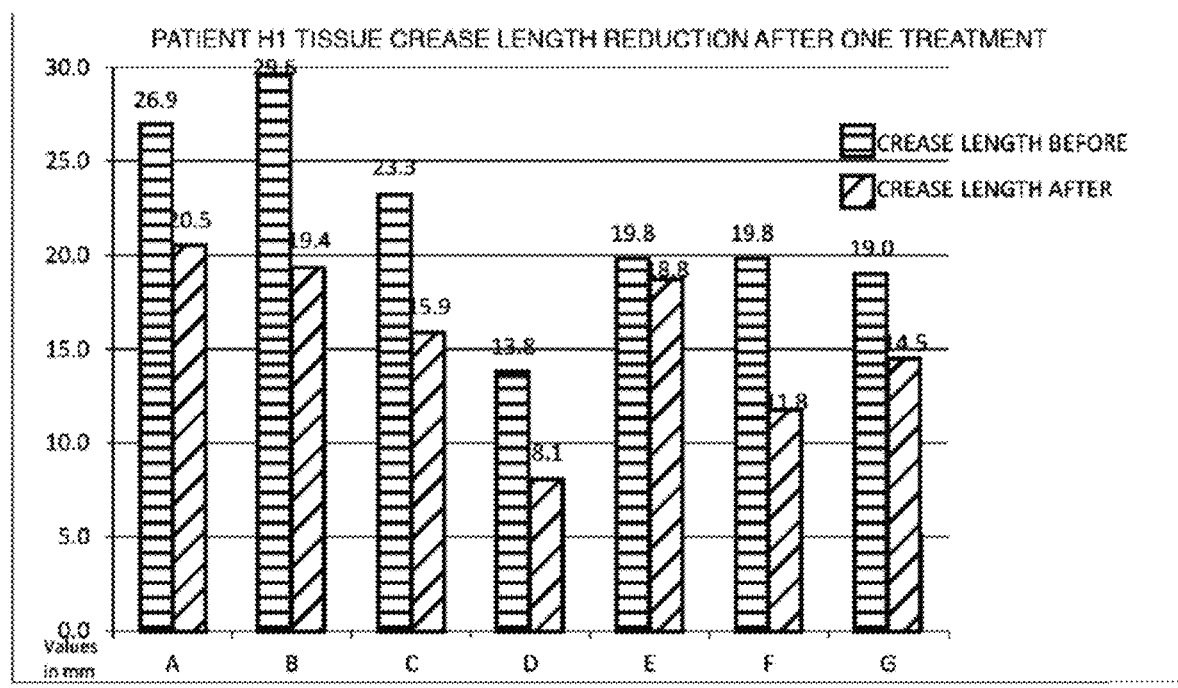
FIG. 16 shows changes in epithelium crease length of a leg keloid scar before (left bar of each pair) and after (right bar of each pair) treatment with a composition comprising hyaluronic acid, iron, and copper gluconate. Pictures were taken of the leg scar before and after treatment, and scar crease length was measured along 7 points (before and after).
Figure 17:
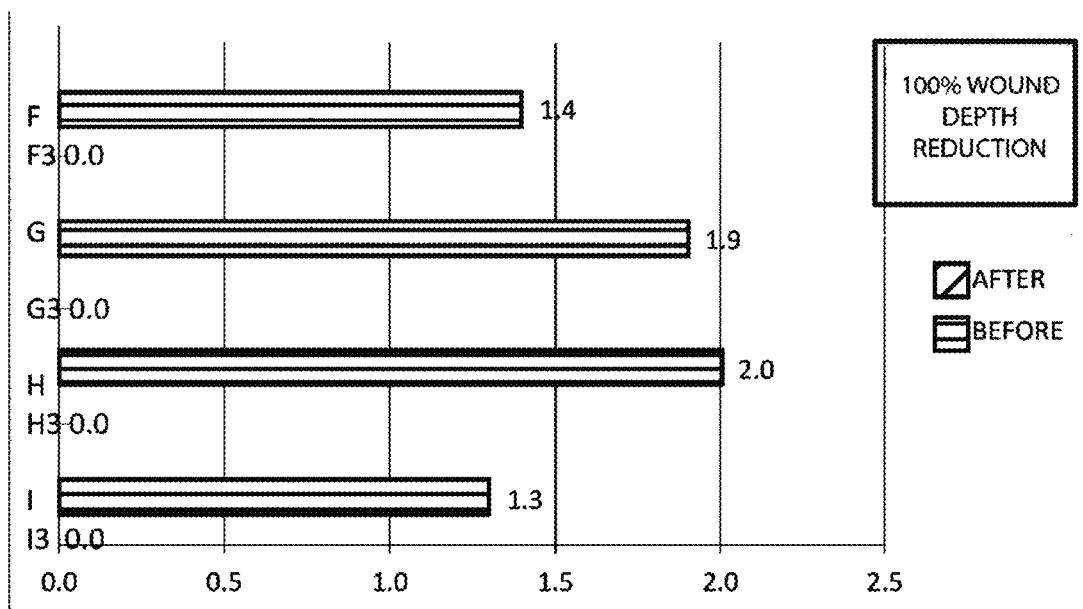
FIG. 17 shows changes in an open leg wound depth before (top bar of each pair) and after (bottom bar of each pair) treatment with a composition comprising hyaluronic acid, iron, and copper gluconate. Pictures were taken of the leg wound before and after treatment and wound depth was measured along 4 points (F, G, H and I, before and after).
Figure 18:
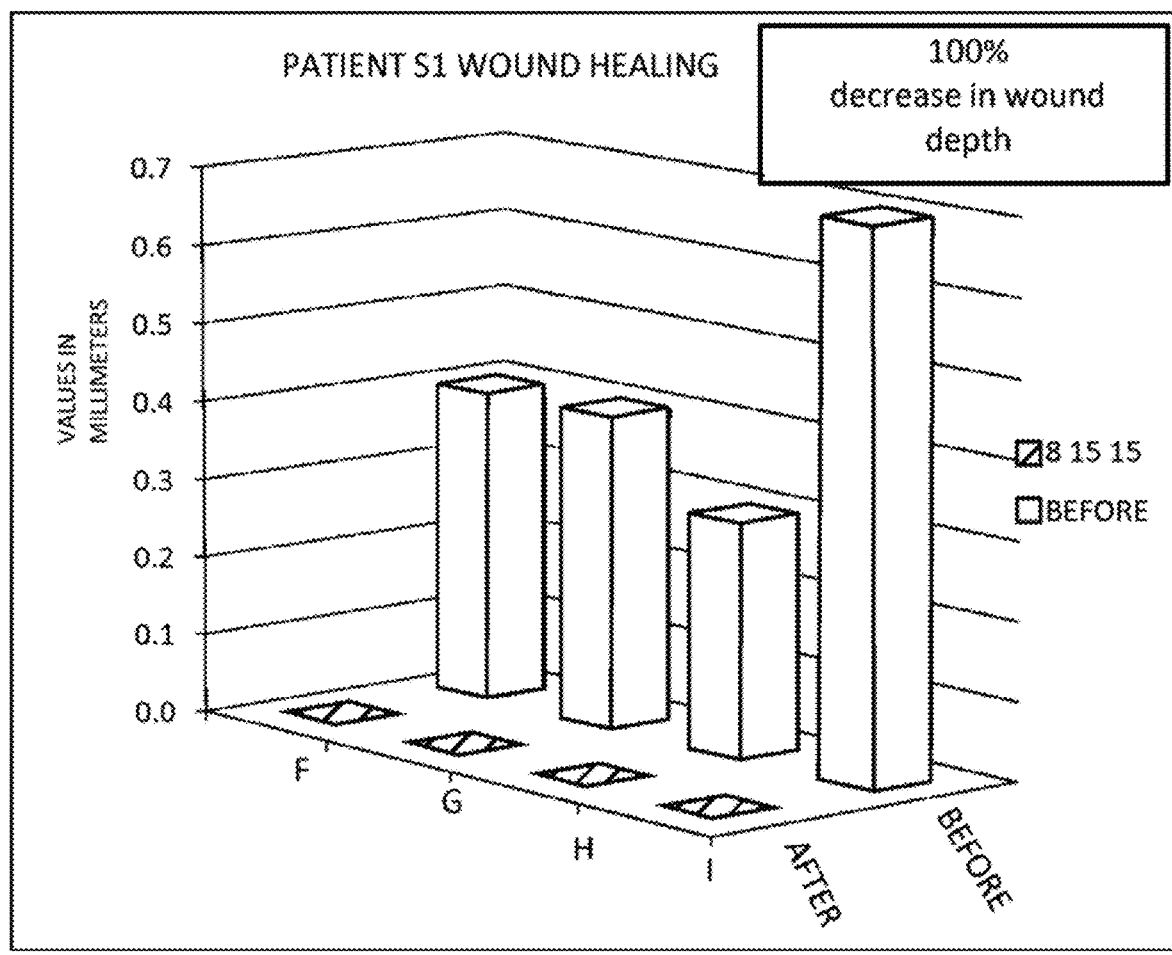
FIG. 18 shows changes in an open leg wound depth before (right back bars) and after (left forward bars) treatment with a composition comprising hyaluronic acid, iron, and copper gluconate. Pictures were taken of the leg wound before and after treatment and wound depth was measured along 4 points (F, G, H and I, before and after).
Figure 19:
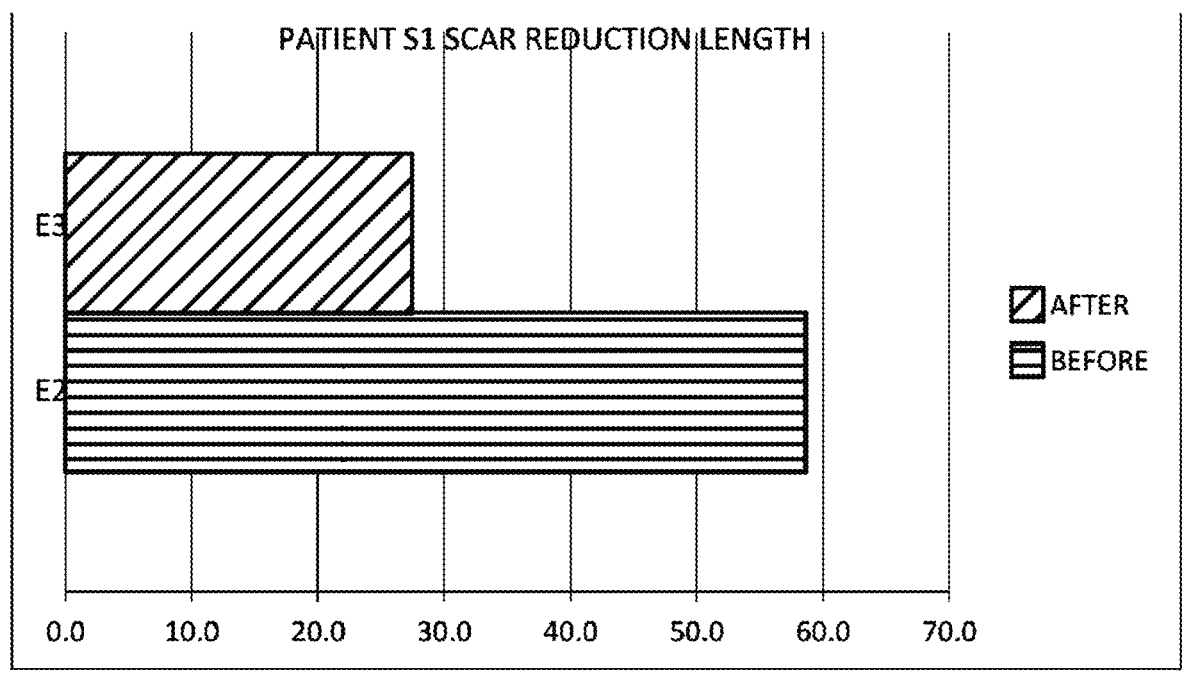
FIG. 19 shows changes in a leg scar length before (bottom bar) and after (top bar) treatment with a composition comprising hyaluronic acid, iron, and copper gluconate. Pictures were taken of the leg scar before and after treatment and scar length was measured along 2 points (before and after).
Figure 20A:
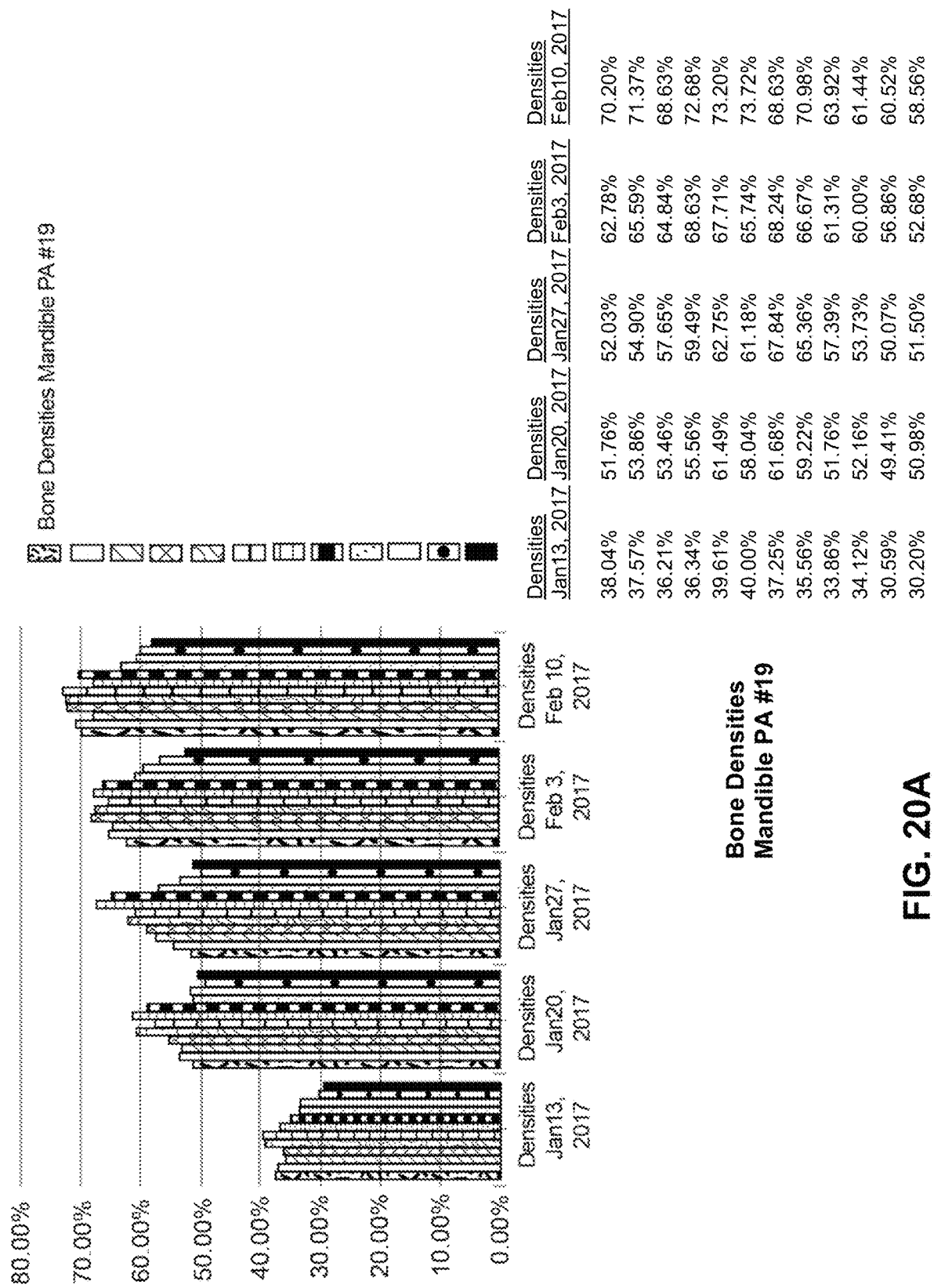
FIG. 20A-D shows bone densities (bone growth) after treatment with a composition comprising collagen, iron, and copper gluconate. All percentages are percentages of opaqueness on an x-ray. All percentages of opaqueness were measured by measuring the same points along each x-ray each month. When bone grows, the dark x-ray turns to opaque. Different dark points measured (no bone present) turned opaque (bone growth) with measured time.
Figure 20B:
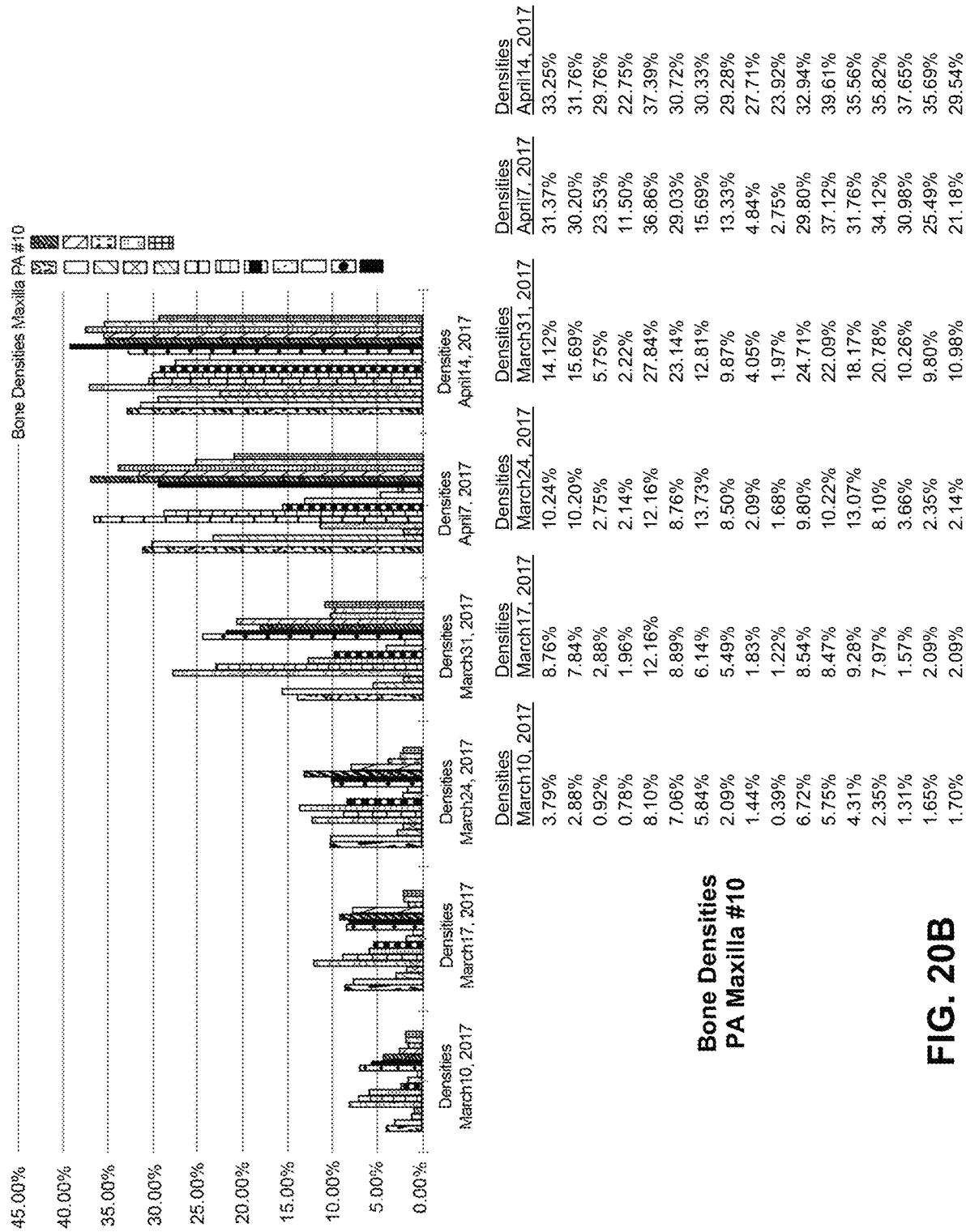
Figure 20C:
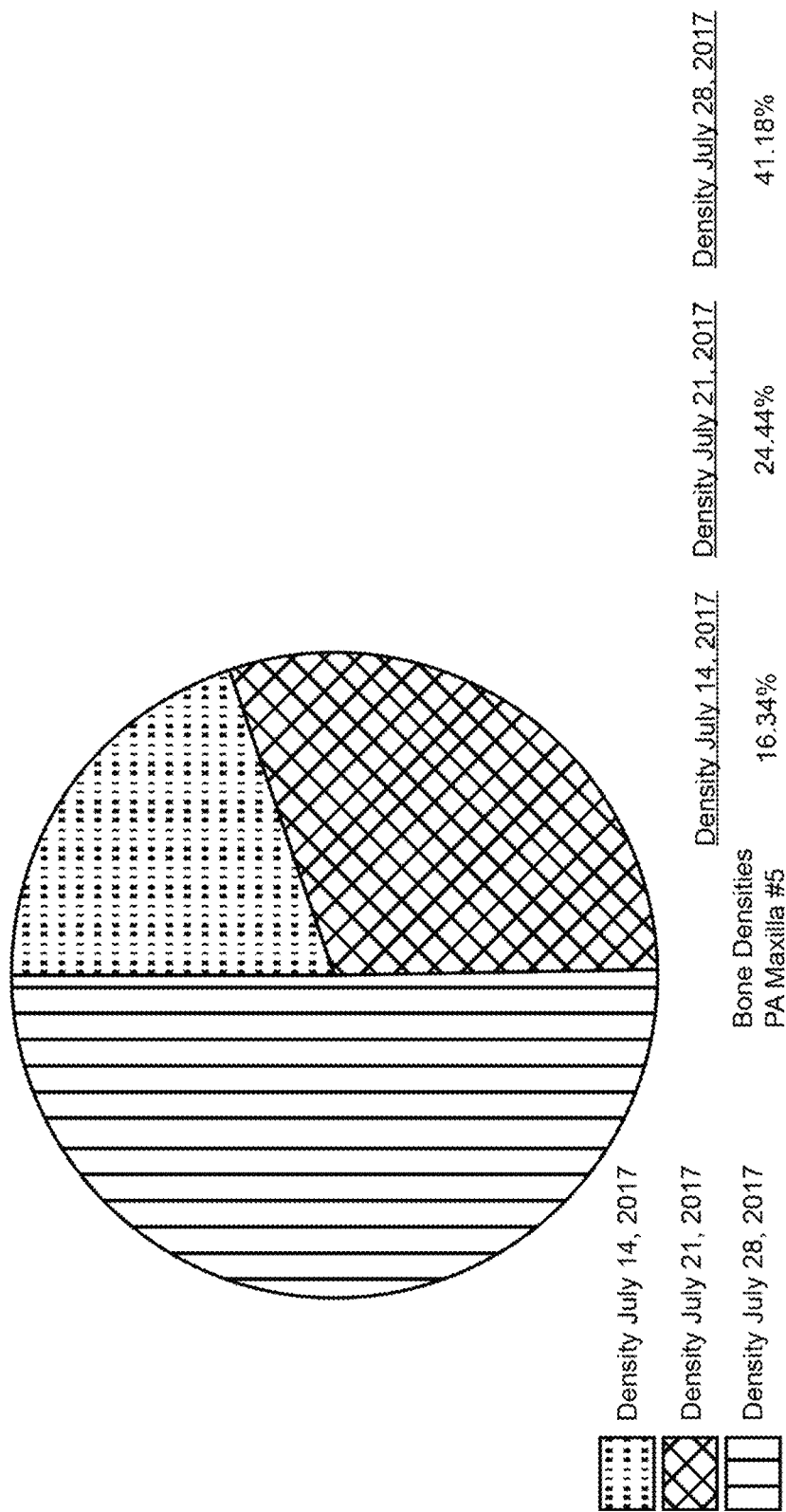
Figure 20D:
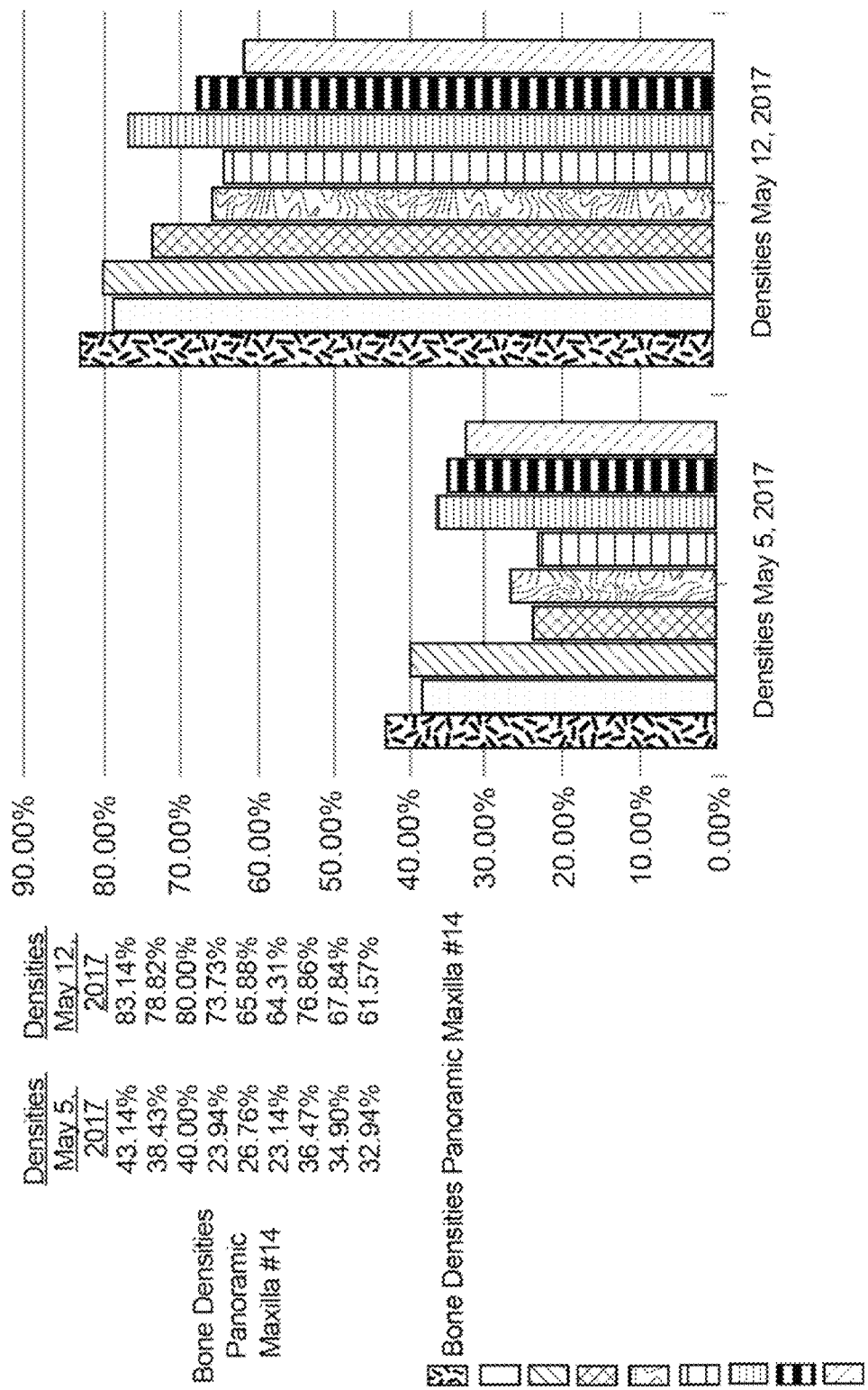

The formulations (compositions) used to generate the data of FIGS. 35-46 were formulated as a gel.

DETAILED DESCRIPTION

Provided herein are systems, compositions, devices, and methods for the treatment of tissue damage and/or to induce tissue regeneration. Compositions disclosed herein may comprise two or more of collagen, hyaluronic acid, fucose, copper, iron, silver, gold, ATP and acetylcholine. In some embodiments, a composition comprises three or more ingredients selected from collagen, hyaluronic acid, fucose, copper, iron, silver, gold, ATP and acetylcholine. In some embodiments, a composition comprises four, five, six, seven, or eight ingredients selected from collagen, hyaluronic acid, fucose, copper, iron, silver, gold, ATP and acetylcholine. In certain embodiments, a composition comprises collagen, hyaluronic acid, fucose, copper, iron, silver, gold, ATP and acetylcholine. A system and/or a device may be and/or form delivery means of one or more substrates (and/or one or more portions of a substrate (e.g., the collagen or Hyaluronic acid) to a wound site. A given system and/or device may be configured such that one or more compositions (and/or portions of compositions) are delivered to cells by means of the energy generated by the device and/or system, and/or by other means.

In some embodiments, a composition comprises collagen and one, two, three, four or more ingredients selected from hyaluronic acid, fucose, copper, iron, silver, gold, ATP and acetylcholine. In some embodiments, a composition comprises hyaluronic acid and one, two, three, four or more ingredients selected from collagen, fucose, copper, iron, silver, gold, ATP and acetylcholine. In some embodiments, a composition comprises hyaluronic acid and one, two, three, four or more ingredients selected from collagen, fucose, copper, iron, silver, gold, ATP and acetylcholine.

Compositions disclosed herein can be used alone or in combination with administration of energy (e.g., laser energy, light from a light emitting diode, radiofrequency (RF) energy, audio frequency energy, etc.) to a damaged tissue to induce wound healing and/or tissue regeneration. Compositions disclosed herein are sometimes referred to herein as "substrates". One or more compositions or substrates as described herein may be included as a component in a system that also includes an energy source or device, and/or other components.

Subjects

The term "subject" refers to a mammal. Any suitable mammal can be treated by a method or composition described herein. Non-limiting examples of mammals include a human, non-human primate (e.g., ape, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a subject is a non-human primate or a human. In some embodiments a subject is a human. A subject can be any age or at any stage of development (e.g., an adult, teen, child, infant, or a mammal in utero). A subject can be male or female.

Damaged Tissue

In some embodiments, a composition or method herein is used to treat damaged tissue. In some embodiments, a damaged tissue is a wound, non-limiting examples of which include a laceration, cut, scrape, abrasion, scratch, puncture, bite (e.g., an insect or animal bite), burn (e.g., a chemical burn, temperature-induced burn (e.g., frost bite, sun burn, a burn by heat or fire)), bruise or contusion, ulcer, cyst, sprain, muscle tear or pull, ligament tear or pull, a bone fracture or break, a surgical incision site, a surgical cut site, a surgical extraction site. In some embodiment, a wound is a tooth extraction site. In certain embodiments, a wound is an acute wound. In certain embodiments, an acute wound is a wet wound. In certain embodiments, a wound is a chronic wound. In certain embodiments, a chronic wound is a dry wound. In some embodiments, a damaged tissue is hypoxic. In some embodiments, a damaged tissue is ischemic, lacks sufficient circulation, and/or is restricted of blood flow. In some embodiments, damaged tissue comprises tissue lacking collagen integrity, structure or form. In some embodiments, damaged tissue comprises tissue that has lost electrons and therefore damaged due to aging. In some embodiments, a damaged tissue comprises a vasculature obstruction.

In some embodiments, a damaged tissue is a necrotic tissue. In some embodiments, a damaged tissue is a scar. A damaged tissue may be cancerous, diseased (e.g., gum disease), aged, aging, damaged, necrotic, infected, mature, immature, normal, abnormal, missing, underdeveloped, developed, clean, dirty, or contaminated. In certain embodiments, a wound is any area of a subject that has lost any amount of original tissue or bone.

In certain embodiments, a wound is an ulcer. In some embodiments, a wound is a diabetic ulcer. In some embodiments, a wound is a non-healing wound, for example a wound on a diabetic subject that is not healing (e.g., a chronic burn wound, or chronic skin ulcer). In some embodiments, a wound is a venous ulcer.

A damaged tissue may be of any size. In some embodiment, a wound has a mean, median, average or absolute diameter of 0.1 mm to 60 cm or more. In some embodiment, a wound has a mean, median, average or absolute diameter of 0.1 mm to 25 mm, 0.1 mm to 15 mm, 0.1 mm to 10 mm, or 0.1 mm to 5 mm. In some embodiment, a wound has a mean, median, average or absolute depth of 0.1 mm to 25 mm, 0.1 mm to 15 mm, 0.1 mm to 10 mm, or 0.1 mm to 5 mm.

A damaged tissue may be of any age. In some embodiment, a wound is new, for example a wound that appears within 1 day, 1-4 days or up to a week. In some embodiment, a wound is about 4 or more, 6 or more, 20 or more or 60 or more days old. In some embodiment, a wound is new, for example a wound that appears within 1 day, 1-4 days or up to a week.

In some embodiments, a chronic wound is an ulcer or bed sore. In some embodiments, a chronic wound is a diabetic ulcer.

In some embodiments, a damaged tissue comprises endothelium, epithelial tissue, connective tissue (e.g., cartilage or bone), muscle tissue (e.g., smooth muscle, skeletal muscle or cardiac muscle tissue), nervous tissue, and/or combinations thereof. In some embodiments, a damaged tissue comprises damaged bone. In some embodiments, a damaged tissue comprises damaged epithelial tissue. In some embodiments, a damaged tissue comprises damaged veins or arteries.

Energy

In some embodiments, a damaged tissue is treated with energy (e.g., laser energy, light from a light emitting diode, radiofrequency (RF) energy, audio frequency energy, etc.). The energy may be and/or include electromagnetic radiation and/or other energy. The radiation may comprise and/or be associated with photons, electrons, audio waves, radio frequency waves, magnetic waves, electricity, and/or other energy. In some embodiments, a damaged tissue is treated with electromagnetic radiation and one or more compositions described herein. Electromagnetic radiation may be produced by one or more suitable energy sources or devices, non-limiting examples of which include a lasers, a laser photon beam, lamps, a bulb, a tube, a diode, a light emitting diode (LED), LED photon beam, broadband photon beam, radiofrequency electron waveforms, audio frequency waveforms, electrical discharge, the like, and combinations thereof.

In some embodiments, electromagnetic radiation that is used for a system and/or method described herein is at a wavelength and/or frequency in the visible spectrum. In some embodiments, electromagnetic radiation that is used for a system and/or a method described herein is at a wavelength and/or frequency in the infrared spectrum. In some embodiments, electromagnetic radiation that is used for a system and/or a method described herein is at a wavelength and/or frequency in the ultraviolet spectrum. In some embodiments, electromagnetic radiation that is used for a system and/or a method described herein is at a wavelength and frequency in the radio frequency (RF) spectrum of electromagnetic radiation. In some embodiments, the energy that is used for a system and/or a method described herein is at a wavelength and frequency in the audio frequency spectrum. In some embodiments, electromagnetic radiation that is used for a system and/or a method described herein is at one or more wavelengths, frequencies, and/or powers described herein, and combinations thereof.

In some embodiments, energy (e.g., laser energy, light from a light emitting diode, radiofrequency (RF) energy, audio frequency energy, etc.) that is used for a system and/or a method described herein comprises a wavelength between about 10 nm and 100 nm, or intermediate ranges therein. In some embodiments, energy (e.g., laser energy, light from a light emitting diode, radiofrequency (RF) energy, audio frequency energy, etc.) that is used for a system and/or a method described herein comprises a wavelength between about 10 nm and 100 nm, or intermediate ranges therein. In some embodiments, energy (e.g., laser energy, light from a light emitting diode, radiofrequency (RF) energy, audio frequency energy, etc.) that is used for a system and/or a method described herein comprises a wavelength between about 10 nm and 1800 nm, between about 100 nm and 1800 nm, between about 200 nm and 1200 nm, between about 200 nm and about 2500 nm, between about 380 nm and 1200 nm, between about 400 nm and 1200 nm or between about 450 nm and 1200 nm. In some embodiments, energy (e.g., laser energy, light from a light emitting diode, radiofrequency (RF) energy, audio frequency energy, etc.) that is used for a system and/or a method described herein comprises a wavelength between about 600-1200 nm, 700-1400 nm, 700-1200 nm, 750-1000 nm, 800-900 nm, 520-570 nm, 620-750 nm or 570-590 nm. In some embodiments, energy (e.g., laser energy, light from a light emitting diode, radiofrequency (RF) energy, audio frequency energy, etc.) that is used for a system and/or a method described herein comprises a wavelength between about 200 nm and 2500 nm. In some embodiments, energy (e.g., laser energy, light from a light emitting diode, radiofrequency (RF) energy, audio frequency energy, etc.) that is used for a system and/or a method described herein comprise about a 1 Hz to about a 2.4 GHz frequency range.

In some embodiments, energy that is used for a system and/or a method described herein comprises a wavelength in the radio frequency (RF) range, for example between about 1 Hz to about 2.4 GHz. In some embodiments, RF frequency that is used for a method herein comprises a wavelength in a range of about 1 Hz to about 2.4 GHz.

In some embodiments, energy that is used for a system and/or a method described herein provides an energy (i.e., a dose) to a region of tissue damage of about 1 Joule/cm$^2$ to about 400 Joule/cm$^2$, about 1 Joule/cm$^2$ to about 150 Joule/cm$^2$, about 1 Joule/cm$^2$ to about 100 Joule/cm$^2$, about 10 Joule/cm$^2$ to about 150 Joule/cm$^2$, or about 20 Joule/cm$^2$ to about 100 Joule/cm$^2$.

In some embodiments, a laser or light source providing electromagnetic radiation (e.g., energy) to a region of tissue damage comprises a power of about 0.0001 W to about 100 W, 0.0001 to about 40 W, about 0.0001 to about 10 W, about 0.0001 to about 5 W, or about 0.001 to about 1 W per waveform, beam or current. In some embodiments, an infrared light source comprises a power of about 0.001 W-5 W. In some embodiments, an RF source comprises a power of about 0.001 W to about 10 W. In some embodiments, an RF source comprises a power of about 10 W or less, 9 W or less, 8 W or less, 6 W or less, or 5 W or less. In some embodiments, an RF source emits at a frequency in a range of 3 Hz to 30 GHz, 0.5 MHz to 24 GHz, 0.1 MHz to 40 MHz, 0.1 MHz to 20 MHz, 0.2-10 MHz, 0.3-5 MHz, or 0.5 KHz to 40 KHz. In some embodiments, an RF source emits at a frequency in a range of 500 KHz or less.

Devices

A therapeutically effective amount of energy (e.g., laser energy, light from a light emitting diode, radiofrequency (RF) energy, audio frequency energy, etc.) can be applied to a damaged tissue using a suitable device. A device may include an energy source configured to produce the energy described here, electronic circuitry, a housing, one or more components configured to direct the energy, and/or other components. In some embodiments, a device that can be used in a system and/or for a method described herein is shown in one or more of FIGS. 21-34. In some embodiments, example devices (e.g., laser, RF, LED, audio frequency, etc.), and/or device components, similar to and/or the same as the devices and/or device components described herein that can be used in a system and/or for a method described herein are described in U.S. patent application Ser. No. 14/937,858 (titled "Laser Assisted Wound Healing Protocol and System" and filed on Nov. 10, 2015); U.S. patent application Ser. No. 15/348,793 (titled "Laser Assisted Wound Healing Protocol and System" and filed on Nov. 10, 2016); and/or U.S. patent application Ser. No. 15/811,651 (titled "Laser Assisted Wound Healing Protocol and System" and filed on Nov. 13, 2017); which are each incorporated by reference in their entirety herein.

In some embodiments a device comprises an energy source capable of emitting a therapeutically effective amount of energy to a damaged tissue. In some embodiments, a device comprises more than one energy source capable of emitting different types of energy (e.g., laser, RF, audio frequency, LED energy, etc.), energy having different wavelengths (e.g., energy comprising dual wavelengths may be produced by a single device), different powers, different doses, and/or other characteristics. In some embodiments, a device comprises one or more of a handpiece (e.g., a housing), an energy source (e.g., laser, LED, lamp, bulb, an RF source, an audio frequency source (e.g., a speaker), etc.), an aperture, one or more lenses, fiber optics, a user interface, a control panel, a control pad, a conduit, and/or other components. In some embodiments, a device may include two or more different energy sources. For example, a device may include an LED, a laser energy source, an RF source, an audio frequency source, some combination of two of those, a combination of any three, or a combination of all four. In some embodiments, a device may include and/or produce one or more individual beams and/or waves (e.g., the terms "beam" and "wave" are not intended to be limiting) of energy of one or more of the different types of energy described herein. These beams and/or waves may be output by a device through one or more fibers, openings in a device housing (e.g., handpiece), and/or by other means.

By way of several non-limiting examples, in some embodiments, a device may have one or more of an energy source, an opening (e.g., for generated energy to leave the device), a hand piece, a fiber, panels, leads and/or a pad which emits electrons and/or photons, such as a radiofrequency waveform, an electron current, laser photons, LED photons, and/or broadband light photons having a waveform length in a portion of the electromagnetic spectrum between 200 nm-2500 nm wavelength. As another example, a device and/or energy source may have an opening, a handpiece, a fiber, panels, leads and/or pad, and be configured to generate a radiofrequency waveform and/or electron current having a wattage of less than 40 W per beam or current, and/or having a total energy in joules of less than 40 J/cm2 per beam. As another example, a device may generate a beam of photons with a wavelength range of between 200 nm and 2500 nm at an emitted power between 0.001 W to 50 W per beam or current, and/or having irradiance between 0.001 W to 10 W/cm2 per beam or current. As another example, a device may generate photons in the wavelength range from about 200 nm to about 2500 nm, at an emitted power between 0.001 W to 50 W, having irradiance between 0.001 W to 10 W/cm2. As another example, a device may generate an RF waveform and/or waveforms, having an emitted power range of between 0.0001 W and 5 W, 8 W or lower, or 6 W or lower; and/or a dose between 1 and 50 J/cm2. As another example, a device may include a laser, LED, and/or broadband energy source configured to produce a beam and/or beams of photons having a wavelength from about 200 nm to about 2500 nm, and/or a beam and/or beams of photons having a wavelength in the red and IR wavelength range (630 nm-1064 nm) at a power of 0.001 to 2 W per beam, and/or having an irradiance of 1 to 300 mW/cm2.

A device may include one or more fiber optic components (or fibers). A fiber optic component may be placed in and/or proximate to treated tissue, for example. In some embodiments, the one or more fiber optic components may comprise one or more individual fibers (e.g., conduits). Individual fibers may conduct energy having the same or different characteristics. For example, individual fibers may conduct energy having different wavelengths, and/or different powers (or average powers). As another example, one fiber may conduct LED light, while another fiber may conduct a different type of energy.

Lasers

In some embodiments, laser energy comprises a laser a beam of light having a wavelength in the green wavelength range (520-570 nm), red wavelength range (620-750 nm), or yellow wavelength range (570-590 nm), having an alternative wattage of 0.001 W to 5 W and/or 0.002 W to 4 W, and/or 0.003 W to 3 W, and/or 0.005 W to 2 W per beam. In some embodiments, the laser light utilizes the IR wavelength range (700 nm-1400 nm) at a laser power of 0.001 W to 5 W per beam to treat tissue. In some embodiments, a device may include a single laser that is used, with or without multiple individual fibers, with or without a handpiece, with or without a lens. In some embodiments, multiple lasers are used in a single device, with or without multiple individual fibers, with or without multiple lenses, with or without a handpiece or handpieces (e.g., a housing). In some embodiments, a device may include one or more lasers comprising one or more fibers (e.g., as further described below and shown in a figure). The one or more fibers may comprise conduits configured to conduct laser light (energy) from a source to an output port or opening in a housing of a device. One or more beams may be separated into and/or otherwise conducted by one or more fibers, for example. In some embodiments, one or more individual fibers may be configured to conduct the laser radiation, where the laser radiation has a power of about 0.1 to 5 W per fiber. A device may be configured such that different fibers may conduct energy having different characteristics (e.g., different wavelengths, powers, frequencies, etc.). Such fibers may be used in one or more of the other devices described herein. For example, one or more such fibers may be used in conjunction with an imaging device described herein.

In some embodiments, fibers may be assembled in a line or in a cross, multi-cross or a geometric form. Precise control of what is coming out each fiber without system loss over time may be achieved with a closed device. In some embodiments, a sapphire lens may be used at the distal end of a fiber handpiece to close off the device. A given fiber may be enclosed in a tubing that does not bend at a high degree. Other lenses can be used such as quartz or even plastic. This closed device does not enter the body. Another type of fiber device may be configured to enter the body. Such a device may have disposable fibers. The attachment of a disposable tip would be a system loss. One way to avoid that is to increase the reflectivity in the tube (fiber or handpiece/housing) to compensate for probable loss.

By way of a non-limiting example, a specific embodiment of a laser that may be used in a device may have some or all of the following characteristics. The example laser may comprise a red or infrared fiber laser with varying degrees of collimation of the beam, with a maximum output power of 12 mW-250 mW at 635 nm-808 nm (+/−5 nm), having a fiber core diameter of 200 um/0.37 NA, with a low operating current of less than 480 mA or less than 70 mM, a low operating voltage of 5V DC, it may be a class Ma laser, it may be CDRH/ROHS compatible, it may be stat, surge, and reverse polarity protected, it may be configured with an auto constant current, have an operating temperature of −10 C to 50 C, and able to operate at up to 90% humidity. It may have a spectral width of about 1 nm, with a wavelength shift of about 0.2 nm. Fiber characteristics may include a 14 (Diameter)×50 (Length) mm shape, with a fiber core diameter of 200 um, a 3 mm cladding diameter, a 0.37 NA, and an SMA connector.

LED

In some embodiments, a device may include one or more LED's. In some embodiments, an LED is configured to utilize the IR wavelength range. In some embodiments, an LED is configured to utilize one or more wavelength ranges that are part of the visible light spectrum (e.g., the green wavelength range, the red wavelength range, the blue wavelength range, etc.) In some embodiments, a device may include a plurality of LED's. The plurality of LED's may be arranged in a pattern, for example. The plurality of LED's may be included in a LED board, and/or other components. For example, the plurality of LED's may include enough LED's to substantially cover a board of a given size (e.g., a 12 inch×12 inch board, a 7 inch×12 inch board, etc.) In some embodiments, LED's may be arranged in a symmetrical array (e.g., a 2×2 array, a 3×3 array, a 4×4 array, a 5×5 array, a 6×6 array, a 7×7 array, an 8×8 array, a 9×9 array, a 10×10 array, an 11×11 array, a 12×12 array, etc.), in non-symmetrical arrays (e.g., 1×2, 3×5, 4×5, etc.), and/or have other arrangements. In some embodiments, an LED board may be configured to be held by a user (e.g., so that the energy from the LED's can be directed toward tissue), self-supporting (e.g., an LED board can form a stand that can be placed next to tissue and stand up right), and/or have other configurations. These examples are not intended to be limiting.

RF/Audio

In some embodiments, RF or audio frequency energy may have a power of up to 10 W or 80 Vpp per wave (volts peak to peak per wave). An RF carrier wave frequency may be in the range of 0.1 MHz to 20 MHz, while a non-sinusoidal waveform may be in the range of 0.5 to 40 KHz, or from 0.5 to 24 GHz. In some embodiments, the carrier wave frequency is in the range of 0.2 MHz to 10 MHz, and/or 0.3 MHz to 5 MHz. In some embodiments, a 0.001 W to 10 W range RF or audio frequency energy, and/or a 0.001 W to 3 W range, is utilized in the hertz range of 40 Hz to 24 GHz. In some embodiments, RF or audio frequency comprises more than one sinusoidal or non-sinusoidal wave wherein the more than one wave may demonstrate a pattern, such as but not limited to a harmonics pattern. Each wave in the pattern may have the power parameters described herein, for example.

In some embodiments, RF or audio frequency may have a power of up to 10 W per opening and be comprised of a carrier wave have a frequency in the range of 0.1 MHz to 20 MHz and a non-sinusoidal waveform in the range of 0.5 to 40 KHz. In some embodiments, the carrier wave frequency is in the range of 0.2 MHz to 10 MHz, and/or 0.3 MHz to 5 MHz. In some embodiments, a 0.001-10 W range RF or audio frequency, and/or a 0.001 W to 3 W range, is utilized in the hertz range of 40 Hz to 24 GHz. In some embodiments, the RF or audio frequency comprises more than one wave wherein at least one wave demonstrates a harmonics pattern. In some embodiments, the at least one non-sinusoidal waveform may be in the range of the above parameters as single or multiple waveforms in the presence or absence of a carrier wave.

In some embodiments, audio energy may be generated by the same components/device that generate the RF energy. Audio waves are just lower frequency waves compared to the RF waves. Audio frequency waves may be generated by a similar device having a handpiece, a pad, a lead, a bar, a probe, and/or other components configured to generate sound (audio waves/energy.)

In some embodiments, RF and/or audio energy may be generated and/or controlled at least in part using a raspberry pi computing module and/or other devices. An example of such a device may be sold by Digi-Key Electronics (https://www.digikey.com/en/product-highlight/r/raspberry-pi/raspberry-pi-4-model b?utm_adgroup=xGeneral&utm_source=google&utm_medium=cpc&utm_campaign=Dynamic%20Search&utm_term=&utm_content=xGeneral&gclid=CjwKCAjwjqT5BRAPEiwAJ1BuBVHEruloeGpds10LIV6-a7vQaZezuiiL9NDJfi2N_WSa7bG63w9OoBoCysYQAvD_BwE) and/or other providers. Such a device may be a single board computer with a 64 bit quad core processor, dual display support, HDMI ports, 8 GB of RAM, dual band 2.4/5.0 GHz wire LAN components, Bluetooth components, and/or other components. In some embodiments, such a device may be user programmed to generate energy having the characteristics described herein.

Imaging

In some embodiments, an imaging device may be included in one or more of the present systems and/or used in one or more of the present methods. An imaging device may be configured to obtain and/or analyze images of tissue and vascular structures at or beneath the epithelium and/or other tissue. The imaging device may or may not have a handle (e.g., embodiments may include a stand and/or other supporting components). In some embodiments, an image device head (which is coupled to the handle) includes a camera, one or more LED's and/or other components. In some embodiments, the one or more LED's that are included in an imaging device may operate at the same or similar wavelengths, powers, frequencies, etc. described herein for the various types of energy. An imaging device may include a display screen, a user entry device (e.g., a keyboard), one or more processors configured to analyze images obtained by the camera and/or other information, and/or other components. In some embodiments, the handle and the head may be configured to be moved back and forth over an area of tissue that is being illuminated by the LED's (e.g., producing visible light in the green wavelength range) and/or imaged by the camera. The camera may acquire a plurality of images during this movement. The one or more processors may analyze and combine the images to produce a three dimensional image of the tissue and/or features within the tissue. The one or more processors may be configured to "stack" the images, for example.

In some embodiments, an imaging device may facilitate finding veins in tissues. The imaging device may produce at least one output indicating the location of veins for the application of tissue analysis in wound treatment. The tissue may be illuminated by an optical probe (e.g., including the components described above). Reflected light is captured by the camera (e.g., having sensors sensitive to different wavelengths of light), which is connected to a computer (e.g., including the one or more processors). In some embodiments, the optical probe may be configured to illuminate the tissue with infrared and/or green lights. In some embodiments, the image stacking and/or other analysis by the one or more processors may facilitate 3d image visualization, machine learning or deep learning algorithm vein detection, edge detection, and/or other operations. In some embodiments, the one or more processors may be, may be included in, and/or may form a raspberry pi computing module (e.g., as described above).

The following figures illustrate several non-limiting examples of the devices and/or device components described above.

Figure 21:
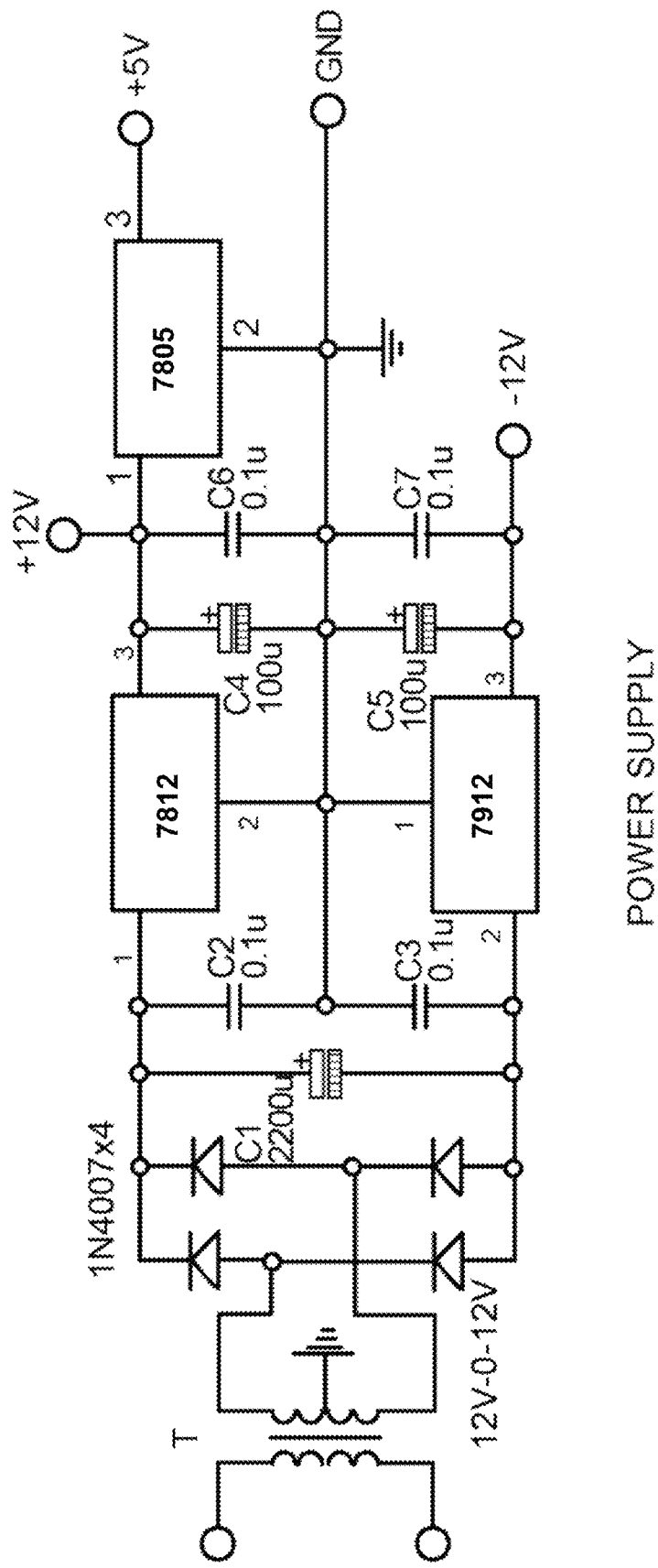
FIG. 21 is an electrical drawing of a possible example of a function generator which generates audio and/or radiofrequency Hz signals.
Figure 22:
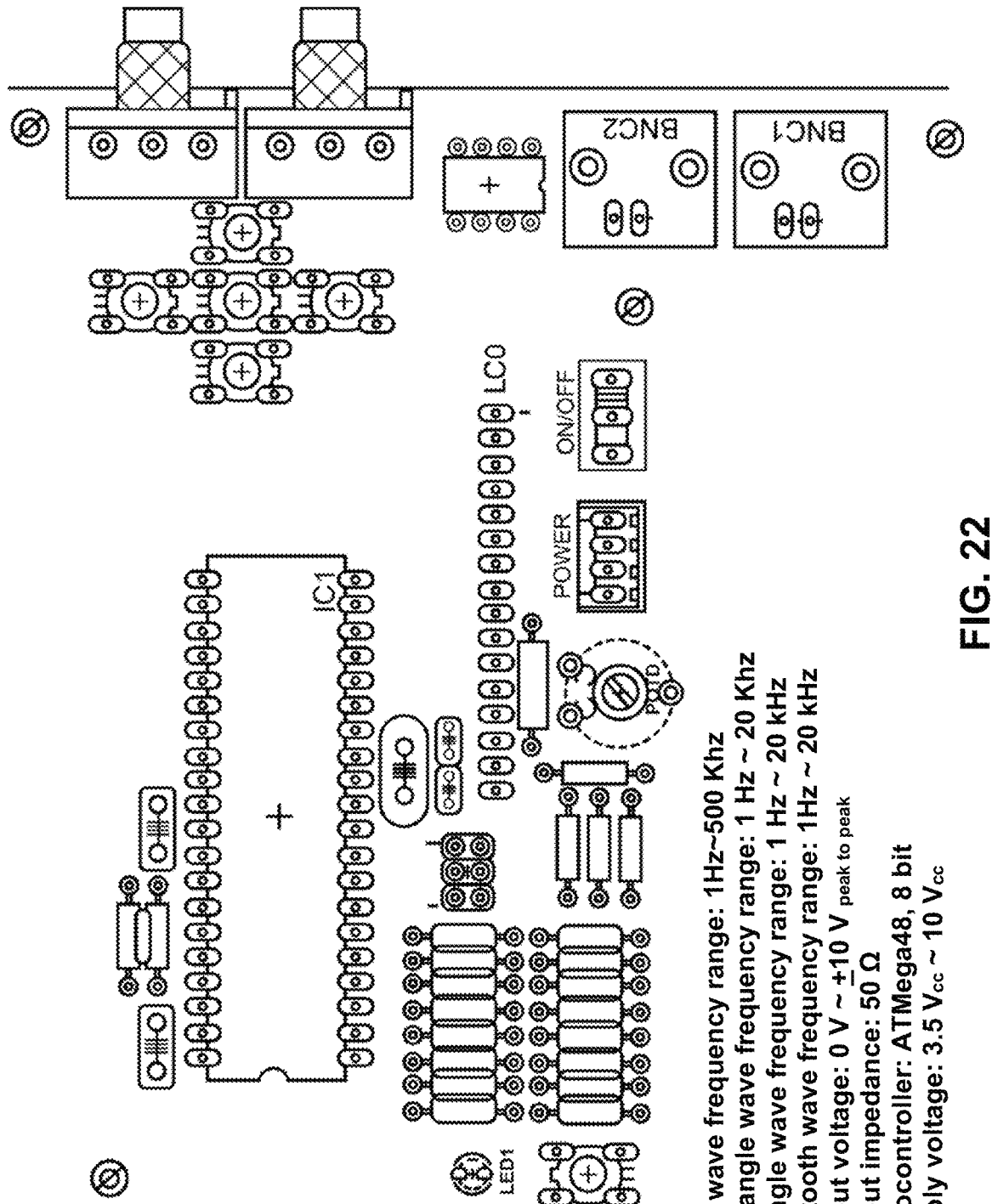
FIG. 22 is a mechanical drawing of a possible example of a function generator which generates audio and/or radiofrequency signals.

FIG. 21 is an electrical drawing of an example of a function generator that may be configured to generate audio and/or radiofrequency signals as described herein. FIG. 22 is a mechanical drawing of an example of a function generator configured to generate audio and/or radiofrequency signals. The function generator may be considered an energy source, for example. As shown in FIG. 21, the function generator includes various resistors, grounds, capacitors, and other components arranged as shown. In some embodiments, as described above, the audio and/or radiofrequency energy (e.g., the audio and/or radiofrequency waves/signals) may be generated by a programmed raspberry pi computing module (e.g., formed by and/or including one or more processors). The components of the audio and/or radio frequency energy source (e.g., a function generator, a raspberry pi computing module, etc.) may be selected and/or arranged to produce an audio or RF wave with a sine wave frequency range of about 1 Hz-500 kHz, a rectangle wave frequency range of about 1 Hz-20 kHz, a triangle wave frequency range of about 1 Hz-20 kHz, or a sawtooth wave frequency range of about 1 Hz-20 kHz, for example. The components of the function generator may be selected and/or arranged such that the function generator has an output voltage of about 0V to +/−10V peak to peak, with an output impedance of about 50 ohms, for example. The components of the function generator may include a microcontroller such as an ATMega48, 8 bit microcontroller, and/or be associated with a supply voltage of about 3.5V DC-10V DC, a supply current of about 300 mA, and/or other characteristics.

Figure 23:
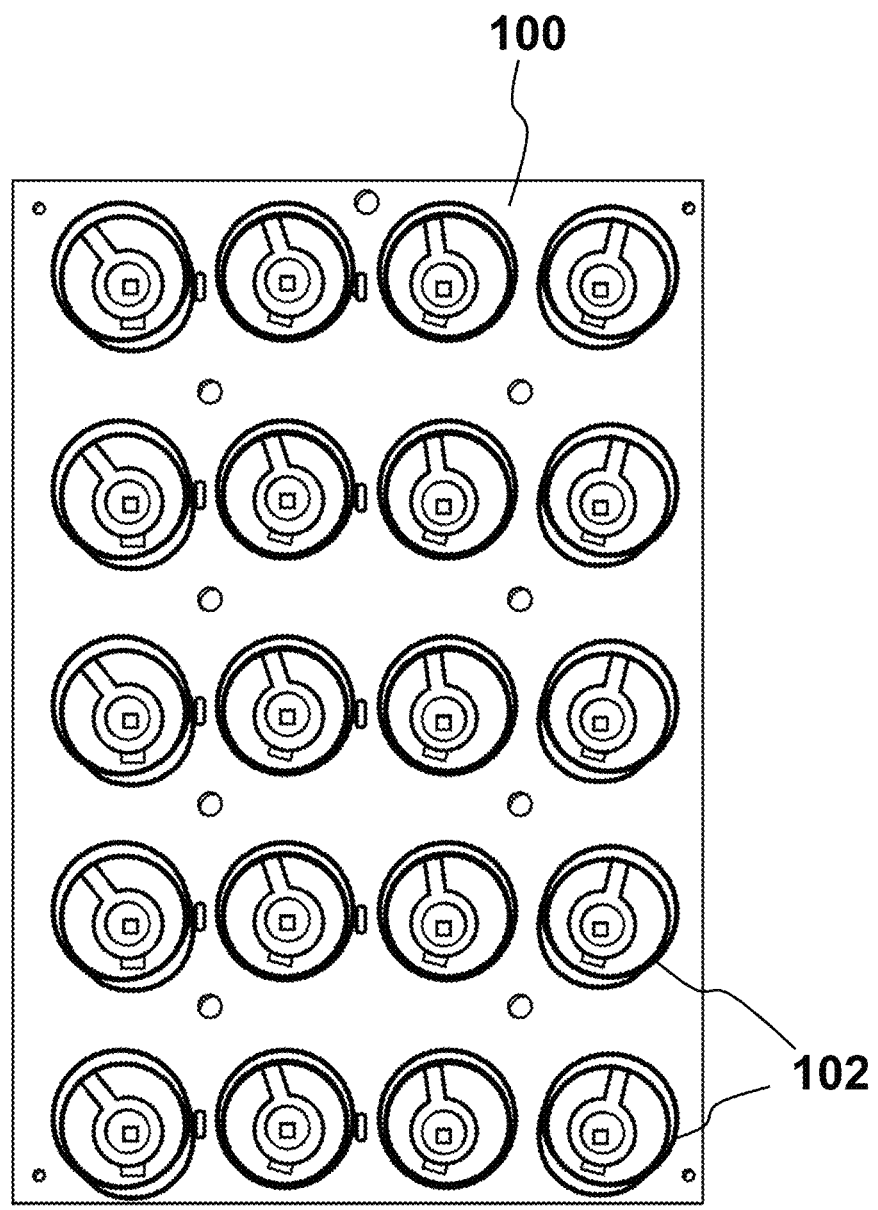
FIG. 23 illustrates a possible example of an LED board that includes a plurality of LEDs that can be used to treat and/or image tissue.

FIG. 23 illustrates an example LED board 100 that includes a plurality of LEDs 102 that can be used to treat and/or image tissue, and/or be used for other purposes. In some embodiments, LED board 100 and/or LED's 102 can be included in one or more devices and/or be used for one or more methods described herein. In the example shown in FIG. 23, LED's 102 are arranged in a non-symmetric 4×5 array. This is just one possible example of such an arrangement. In addition, board 100 may have any dimensions that allow a device comprising LED's 102 to function as described herein (e.g., to therapeutically treat and/or image tissue).

Figure 24A:
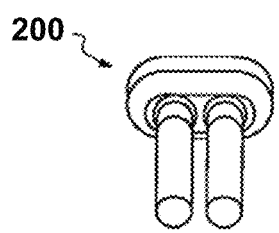
FIG. 24a-24c show various views of an example embodiment of a device configured to generate radiofrequency energy.
Figure 24B:
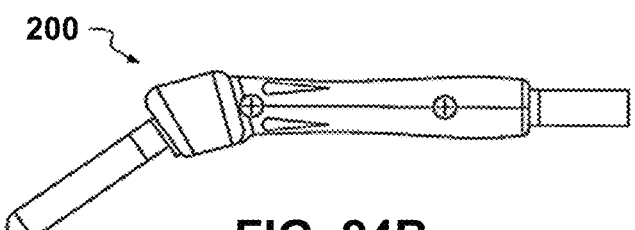
Figure 24C:
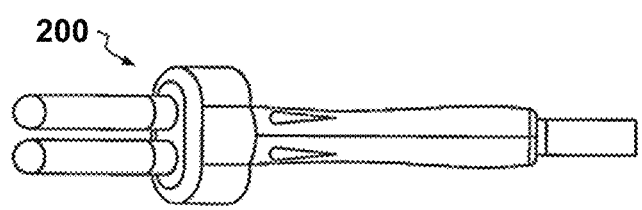

FIG. 24a-24c show various views of a possible embodiment of a device 200 configured to generate radiofrequency and/or audio frequency energy. FIG. 24a shows a front perspective view. FIG. 24b shows a right side view. FIG. 24c shows a bottom view. FIG. 25a-25d show views of the RF or audio frequency device 200 with and without a laser energy source. FIG. 25a shows an exploded view of RF or audio frequency device with laser. FIG. 25b shows a close-up of the handpiece with laser relative to housing. FIG. 25c shows an exploded view of RF or audio frequency device 200 without laser. FIG. 25d shows a detailed view of a housing for an RF or audio frequency device without a laser. Device 200 may be comprised of wire grommet 201 integrally connected to handle 209, handle 209 further comprised of heat sink 202. Housing 203 securely connects to heat sink 202 thereby creating a cavity between the housing 203 and heat sink 202. Laser 204 is positioned within the cavity between housing 203 and heat sink 202. Male connectors 205 connect RF source 208 to housing 203 wherein threaded inserts 206 cover the connection there between. FIG. 25b shows a detailed view of laser 204 and housing 203 in relation to each other.

Figure 26:
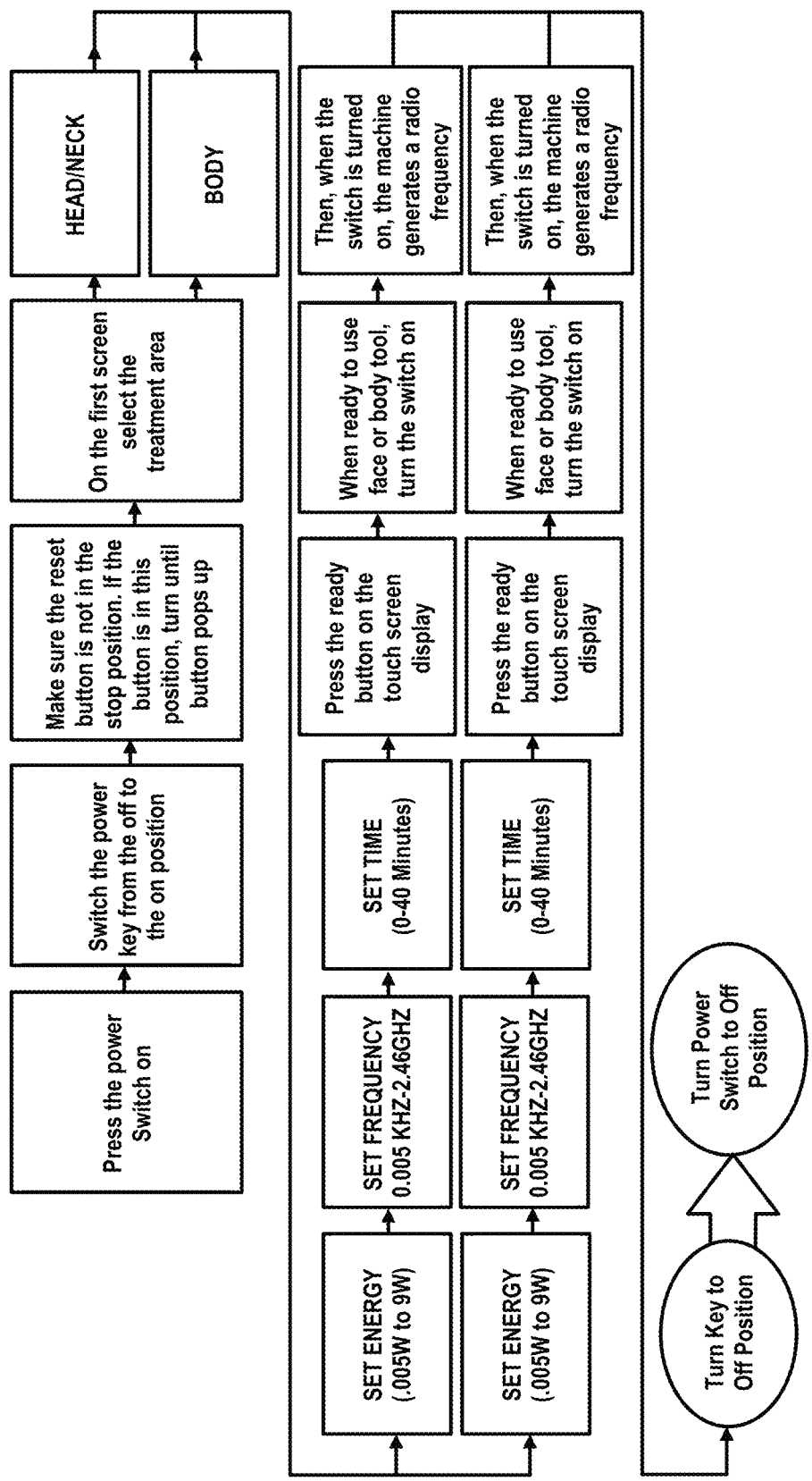
FIG. 26 illustrates a flow chart for an example method for using an RF or audio device.

FIG. 26 illustrates a flow chart for an example method for using an RF or audio frequency device (e.g., device 500 and/or 200 described above).

Figure 27A:
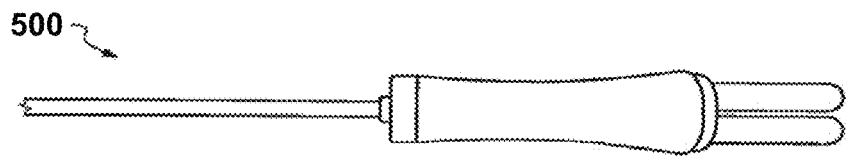
FIGS. 27a-27e show various views of another example embodiment of an RF or audio device.
Figure 27B:
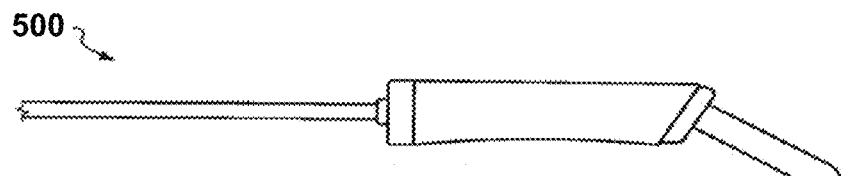
Figure 27C:
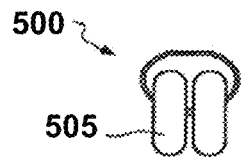
Figure 27D:
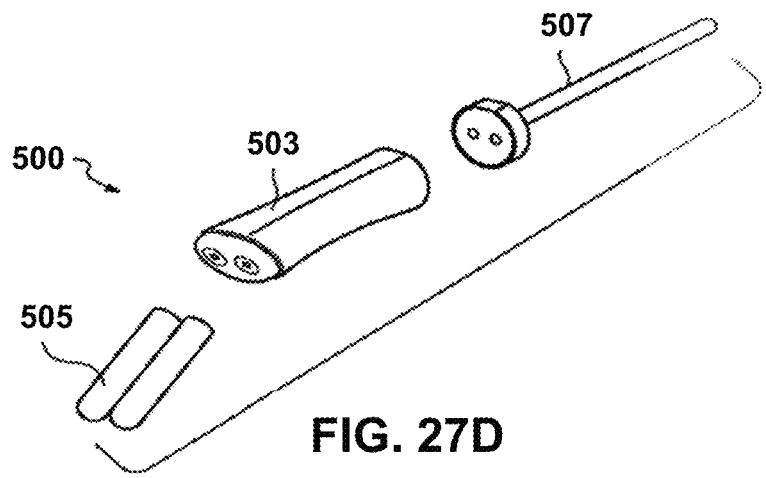
Figure 27E:
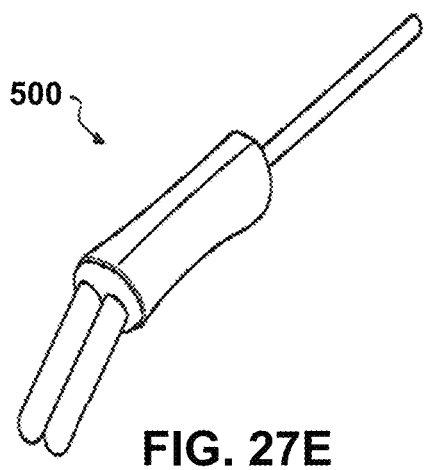

FIGS. 27a-27e show various views of another example embodiment of an RF or audio frequency device. FIG. 27a shows a top view. FIG. 27b shows a side view. FIG. 27c shows a perspective view of the RF or audio frequency tips. FIG. 27d shows an exploded side perspective view. FIG. 27e shows an alternative side perspective view. A device 500 for use in conjunction with the systems, compositions, and methods of the present invention is shown. FIG. 27a shows a top view of the device 500. FIG. 27b shows a side view and FIG. 27c shows a close-up of the tip of device 500. Specifically, FIG. 27d illustrates an exploded view of the device 500 comprised of housing 503, tips 505 and energy source 507. Energy source 507 provides RF or audio frequency in this example. FIG. 27e shows a side perspective view of the assembled device 500.

Figure 28:
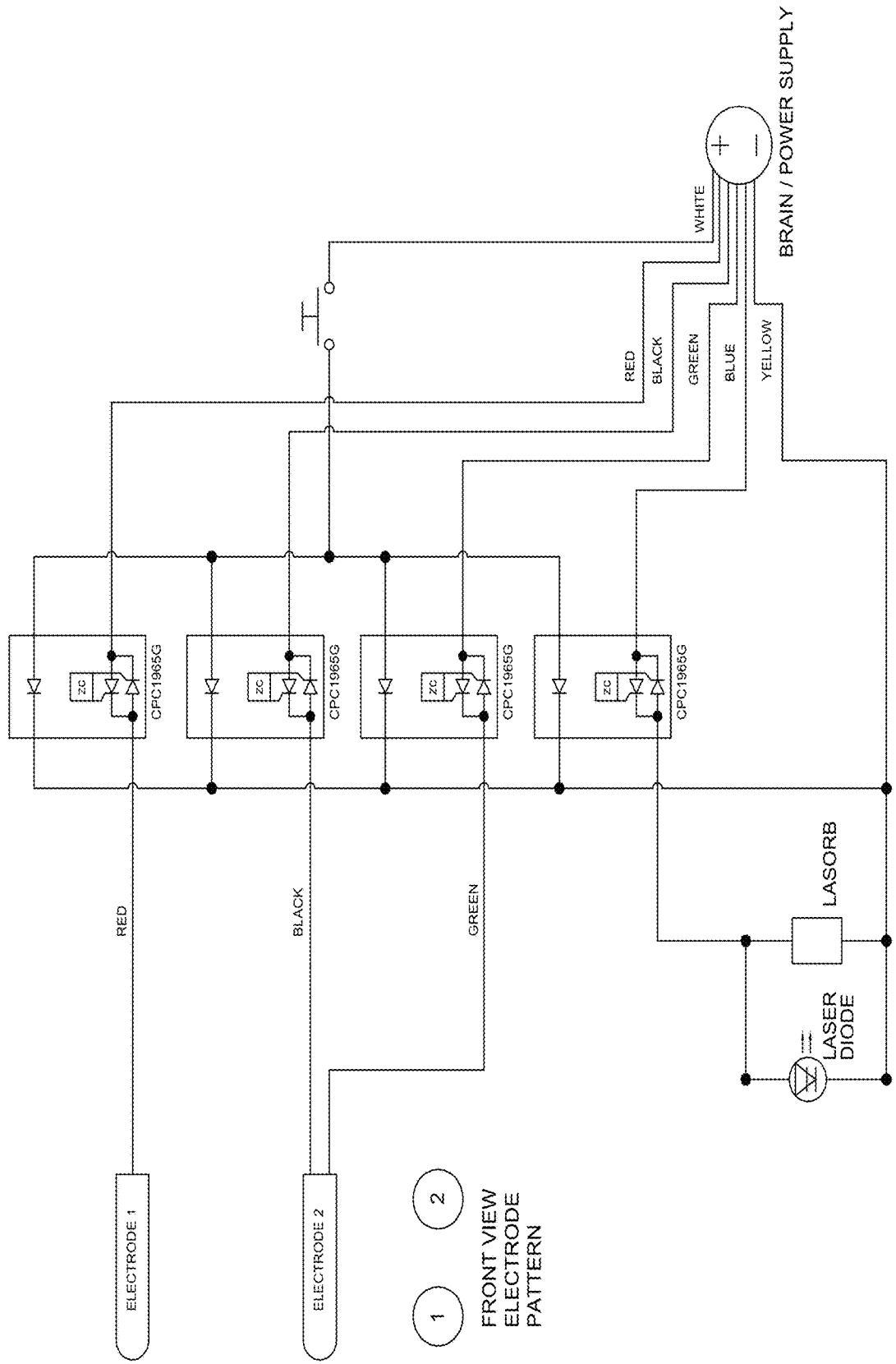
FIG. 28 is an electrical drawing of a possible example of circuitry that may be included in a device described herein.

FIG. 28 is an electrical drawing of example circuitry that may be included in a device such as device 200 and/or 500 described above. For example, the circuitry may include a power source, various wires (e.g., labeled by colors), a laser diode, electrodes (e.g., for outputting RF and/or audio energy), and/or other components.

Figure 29:
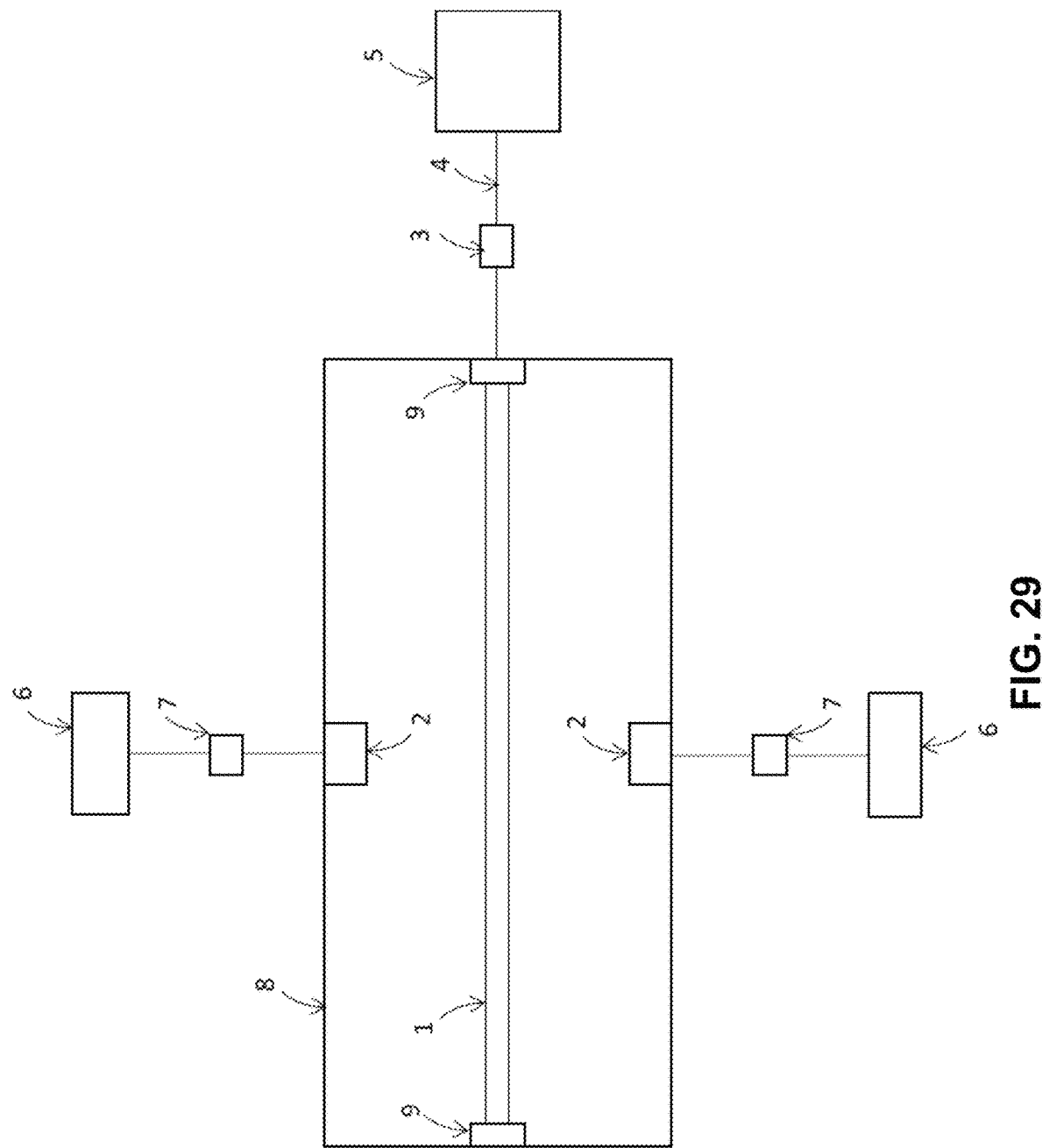
FIG. 29 is a schematic illustration of an example of a possible device that uses laser energy for treatment of tissue.

FIG. 29 is a schematic illustration of an example device that uses laser energy for treatment of tissue. The example device includes a light pipe 1, laser emitting diodes 2 for pumping, a laser delivery means adapter 3 (e.g., any sort of part or component than can be used to couple the laser delivery means (described next), such as a flexible, adjustable, and/or otherwise moveable portion of a housing and/or a component that can be coupled to a housing, etc.), a laser delivery means 4 (e.g., a fiber and/or other conduits), an optics instrument 5 configured for interaction with a patient (e.g., a quartz lens, a sapphire lens, a housing, etc.), a feedback controlled substantially constant current source 6, a plug in 7 to connect a laser to a driver, a cylindrical waveguide with a mirror coating 8 (e.g., see the fiber in the next figure), cavity mirrors 9, and/or other components. In some embodiments, a device that uses laser energy may include more, less, or different components than those shown in FIG. 29. FIG. 29 is an illustration of a single laser. In some embodiments, a single laser is used in a device, with or without a fiber (described below), with or without a handpiece (e.g., a housing or handle), with or without a lens. In some embodiments, multiple lasers are used in a single device, with or without multiple fibers, with or without multiple lenses, with or without a handpiece or handpieces.

Figure 30:
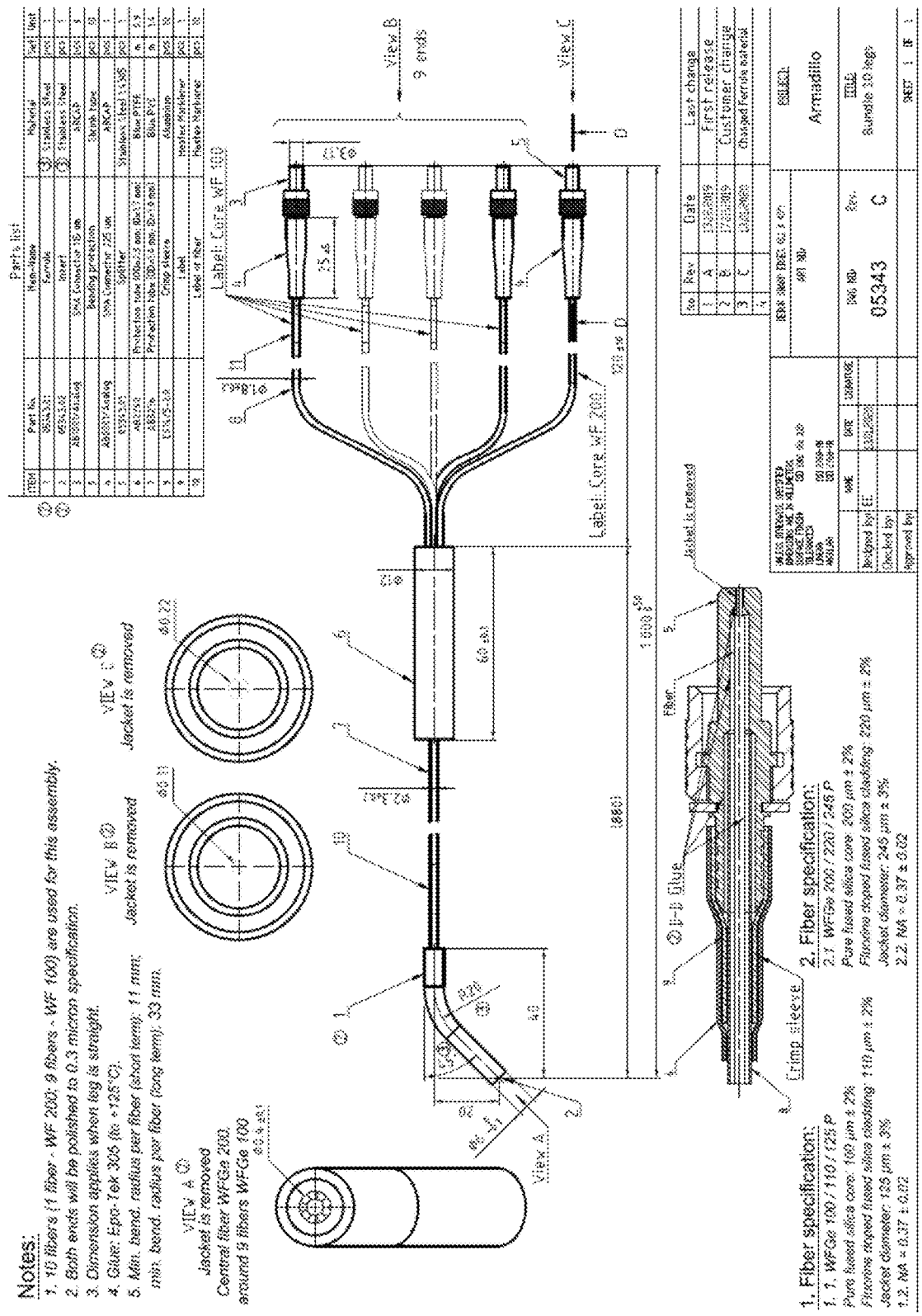
FIG. 30 illustrates an example of laser fibers (e.g., conduits) that may be included in a device that uses laser energy for treatment of tissue.

FIG. 30 illustrates an example of laser fibers (e.g., conduits, fiber optic components) 110 that may be included in a device that uses laser energy for treatment of tissue. Possible components and/or dimensions associated with such fibers are listed in FIG. 30. These possible components and/or dimensions are examples only, and may be varied from what is shown in FIG. 30, provided laser fibers 110 still allow the one or more devices describe herein to function as intended. In some embodiments, a given fiber may comprise a (e.g., pure) fused silica core, fluorine doped fused silica cladding, a jacket, and/or other components. A given fiber may be configured to conduct laser energy from a laser energy source so that it can be directed at tissue for treatment. In some embodiments, a laser fiber as shown in FIG. 30 may form one or more of the components shown in FIG. 29.

Figure 31:
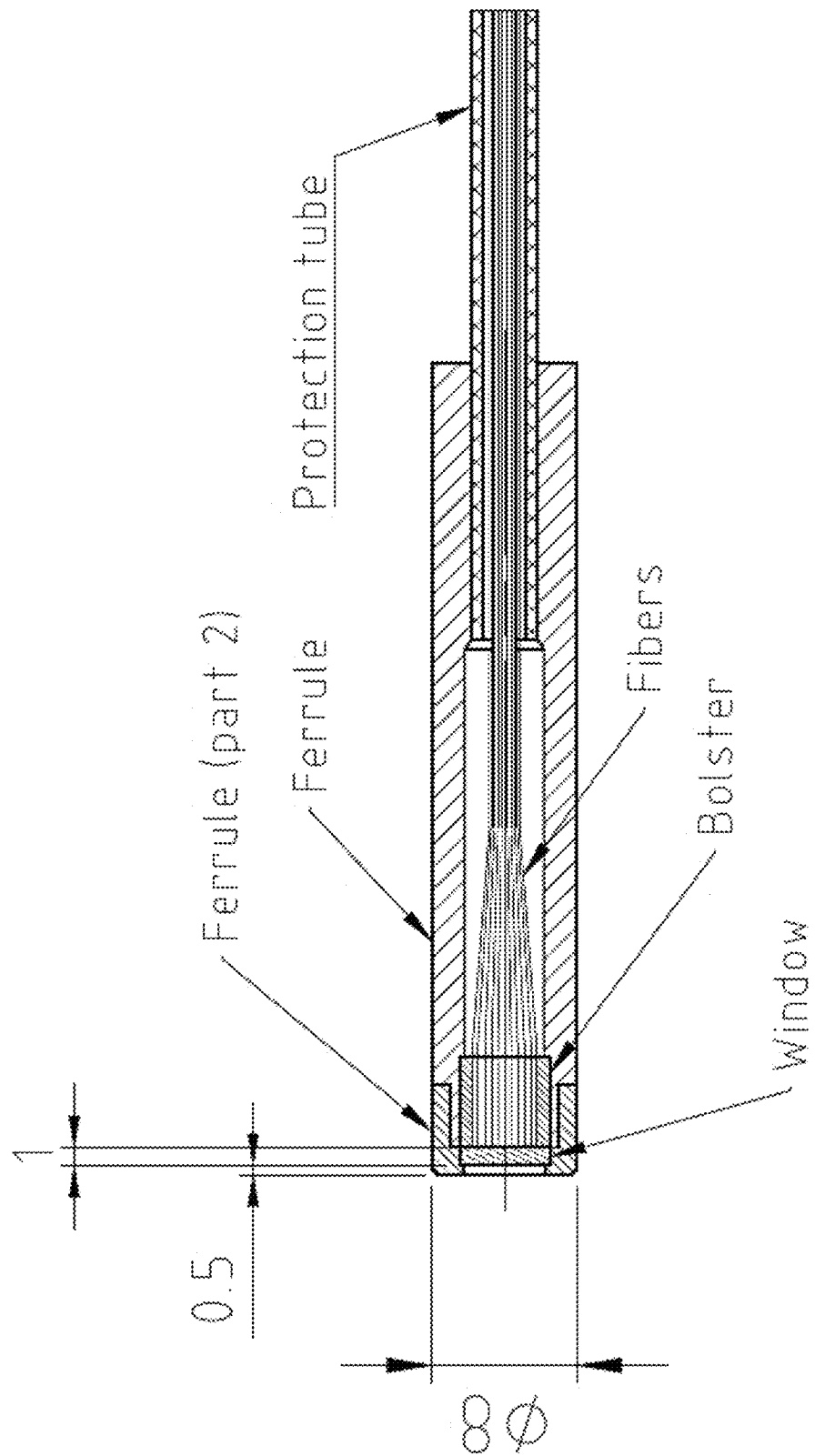
FIG. 31 illustrates combining individual laser fibers for a device that uses laser energy for treatment of tissue.

FIG. 31 illustrates combining individual laser fibers for a device that uses laser energy for treatment of tissue. FIG. 31 is an enlarged view of a ferrule shown in FIG. 30. As shown in FIG. 31, multiple individual laser fibers may be surrounded by a ferrule (having two parts in this example). The individual fibers extend from a window, through a bolster, and are collected so that they can pass through a protection tube. In some embodiments, the window may be silica for example. In some embodiments, one or more fibers may be configured and/or use such that a force and/or effect of light and/or other energy is not diminished by distribution of the light along a line or pattern. If a longer beam was used, the force would be diminished at the distal ends of the beam, for example. Also the patterns seen in the tissue can be matched by using specific patterns of fibers with specific arrangements, orientations, etc.

Figure 32:
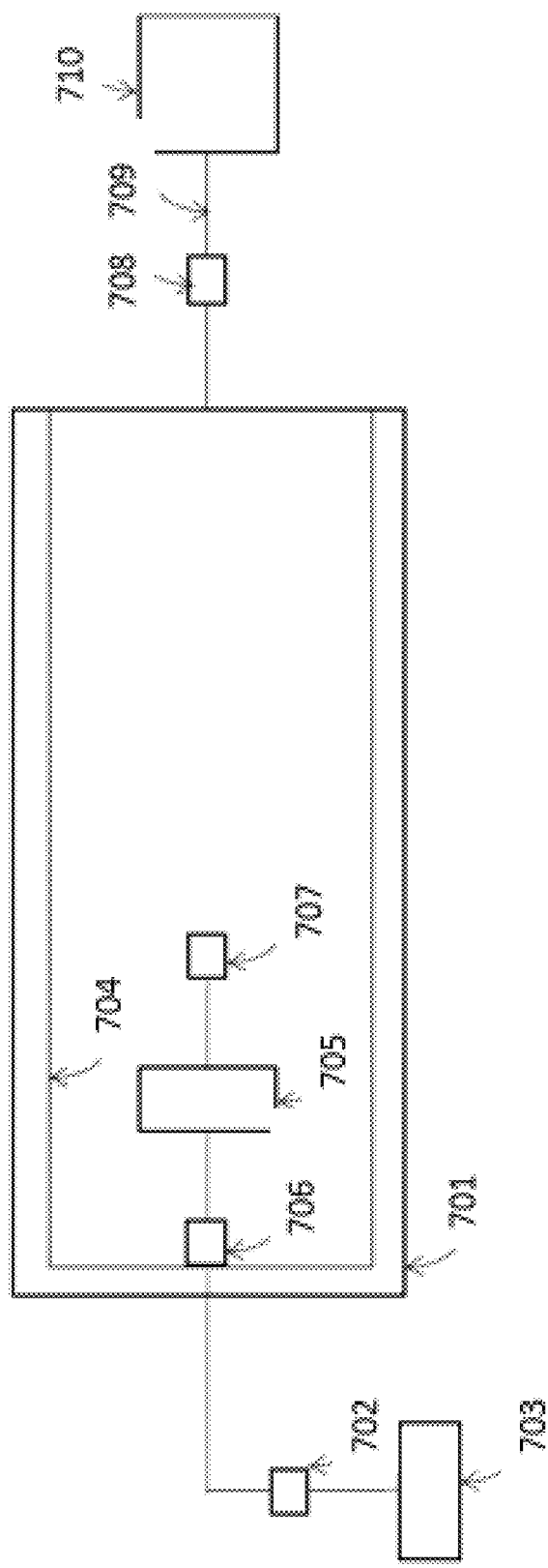
FIG. 32 illustrates an example of components of a possible embodiment of an LED device that may be included in a present system and/or used in a present method.

FIG. 32 illustrates an example of components of a possible embodiment of an LED device that may be included in a present system and/or used in a present method. For example, FIG. 32 illustrates an LED waveguide 701, a plug in 702 configured to connect the LED to a driver, a feedback controlled substantially constant current source 703, cavity mirrors 704, multi-layer semiconductor materials 705, wire bonding means 706, a wavelength filter 707 (e.g., a sapphire or silica lens), an LED to delivery means adaptor 708, LED delivery means 709, an optics instrument 710 configured to facilitate interaction with a patient, and/or other components. In some embodiments, cavity mirrors 704, wavelength filter 707, LED to delivery means adaptor 708, LED delivery means 709, and optics instrument 710 are optional components. In some embodiments, multiple LED's (e.g., including the components shown in FIG. 32) may be used in a single device.

Figure 33:
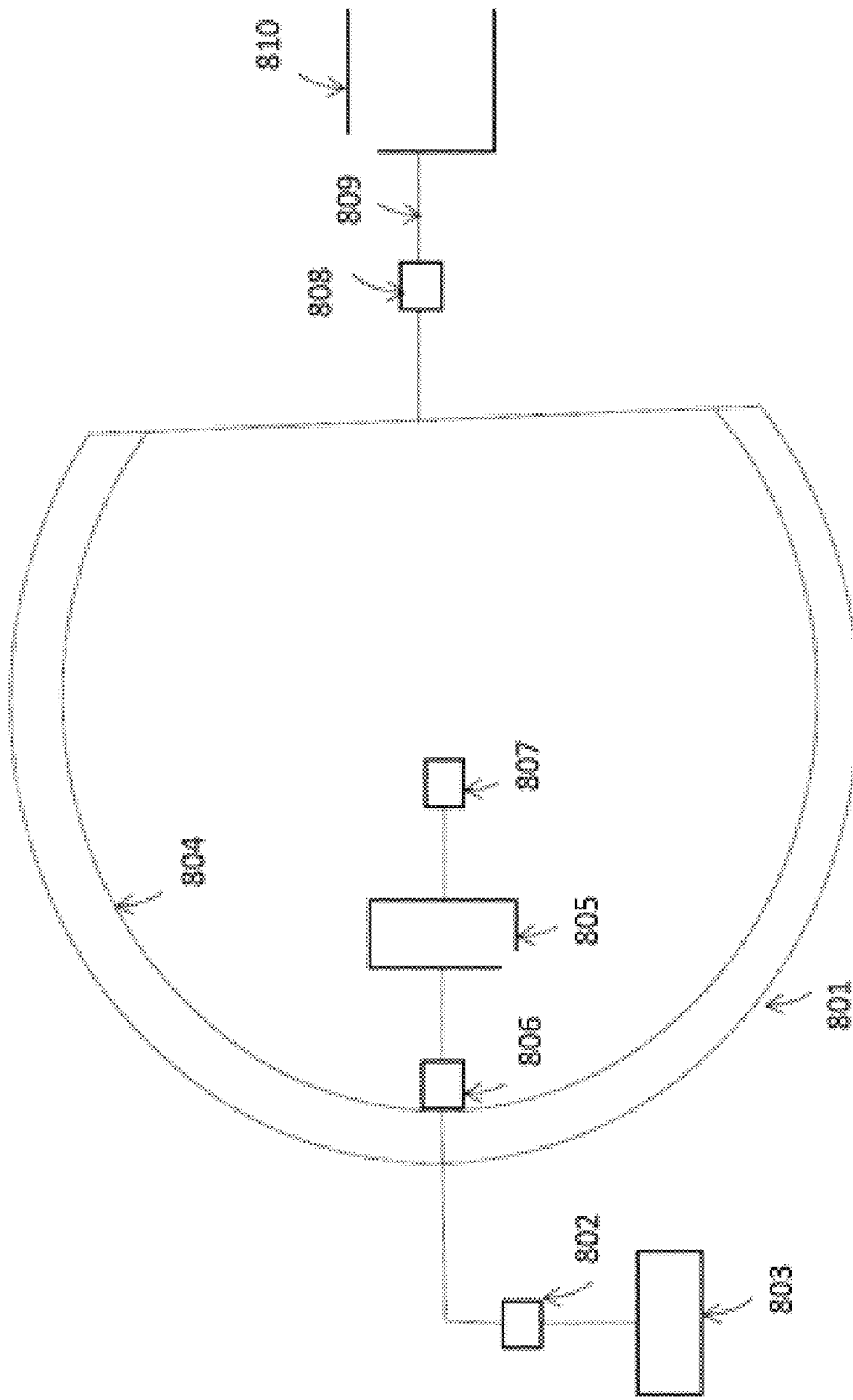
FIG. 33 illustrates another example of components of a possible embodiment of an LED device that may be included in a present system and/or used in a present method.

FIG. 33 illustrates another example of components of a possible embodiment of an LED device that may be included in a present system and/or used in a present method. For example, FIG. 33 illustrates an LED waveguide 801, a plug in 802 configured to connect the LED to a driver, a feedback controlled substantially constant current source 803, cavity mirrors 804, multi-layer semiconductor materials 805, wire bonding means 806, a wavelength filter 807 (e.g., a sapphire or silica lens), an LED to delivery means adaptor 808, LED delivery means 809, an optics instrument 810 configured to facilitate interaction with a patient, and/or other components. In some embodiments, cavity mirrors 804, wavelength filter 807, LED to delivery means adaptor 808, LED delivery means 809, and optics instrument 810 are optional components. In some embodiments, multiple LED's (e.g., including the components shown in FIG. 33) may be used in a single device.

Figure 34:
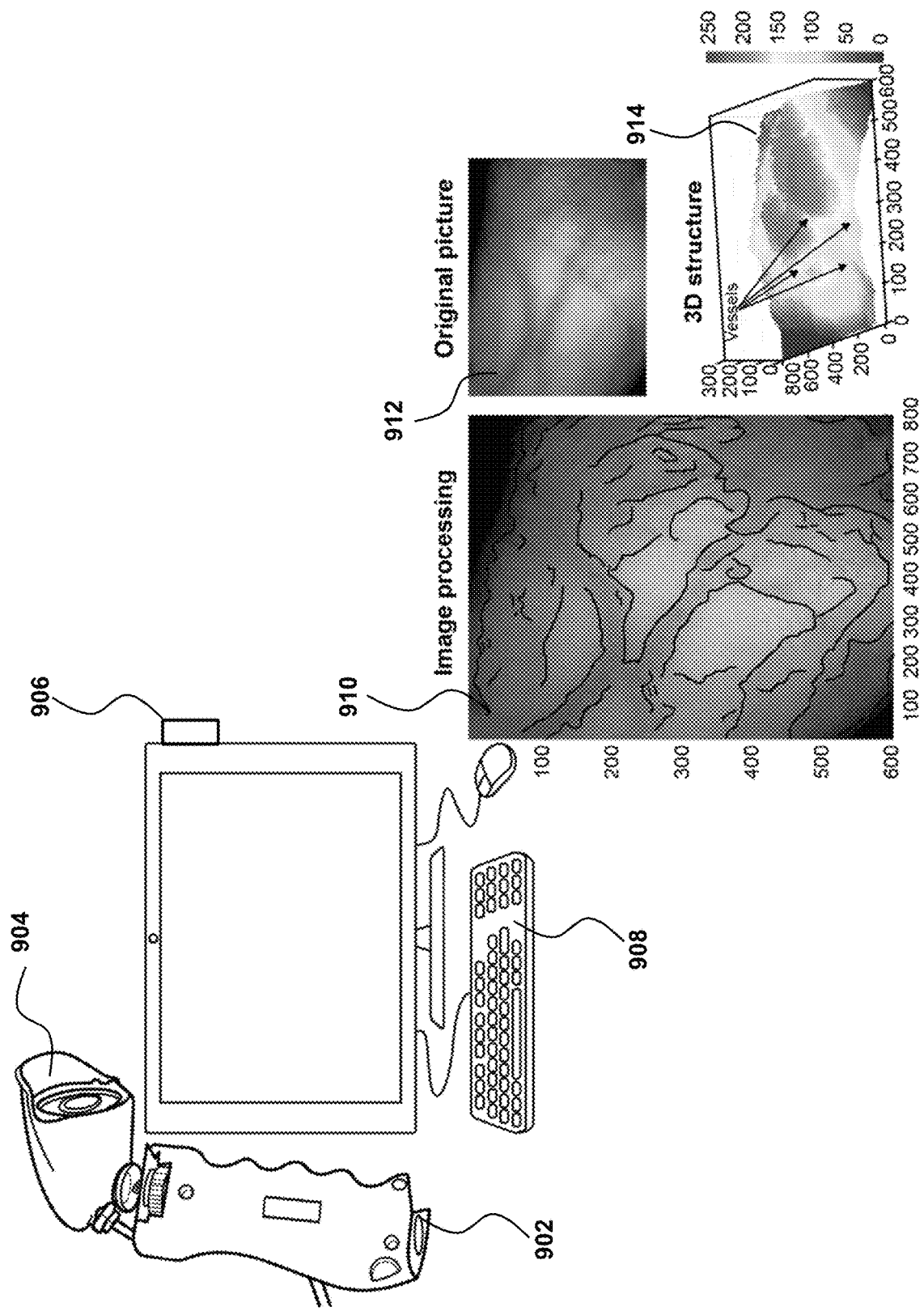
FIG. 34 illustrates an example of components of an imaging device that may be included in a present system and/or used in a present method.

FIG. 34 illustrates an example of components of an imaging device that may be included in a present system and/or used in a present method. FIG. 34 illustrates an imaging device having a handle 902 (e.g., some embodiments may include a stand and/or other supporting components). In some embodiments, an image device head 904 (which is coupled to handle 902) includes a camera, one or more LED's and/or other components. An imaging device may include a display screen 906, a user entry device 908 (e.g., a keyboard), one or more processors configured to analyze 910 images 912 obtained by the camera and/or other information, and/or other components. In some embodiments, the handle and the head may be configured to be moved back and forth over an area of tissue that is being illuminated by the LED's and/or imaged by the camera. The camera may acquire a plurality of images during this movement. The one or more processors may analyze and combine the images to produce a three dimensional image 914 of the tissue and/or features within the tissue. In this example, the images and/or the analysis may be used to detect circulation blockages, circulation loss, tissue density changes, and/or other conditions.

In some embodiments, the one or more processors may be programmed with Python, C++, and/or other programming code. The one or more processors may be configured to determine how far tissue is from a focal point associated with a vein, and provide visualization of the distance on a display. The one or more processors may be configured to cause the camera to take multiple images when the tissue distance becomes close to the focal point, and cause the display to indicate when images are taken. The one or more processors may be configured to store data electronically according to a specific protocol, communicate data (e.g., to a doctor) also with a specific protocol, and/or cause display of the data on a remote computing device (e.g., a doctor's computer) such that the data may be visualized. In some embodiments, the one or more processors are configured to execute machine learning algorithms to extract data from the images.

The terms "power" and "average power" may be used interchangeably herein, with "power" referring to continuous power applied to lasers, LEDs broadband light, radiofrequency, audio or current devices, while "average power" refers to pulsed power applied to lasers, LEDs, broadband light, radiofrequency or current devices of a device or power source.

Similarly, as used herein, the terms "photons" and "photonic electrons" are considered synonymous. The terms "electrons" and "photonic electrons" are considered synonymous. The terms "lines" and "pathways" are considered synonymous. The terms "protocol" and "method" are considered synonymous. The terms "waveform length" and "wavelength" are considered synonymous. The terms, "electron current" and "electric current" are considered synonymous.

Compositions

In some embodiments, provided herein are compositions for use in conducting a method disclosed herein. Compositions are sometimes referred to herein as substrates. A composition as described herein may be a liquid, gel, paste, or powder, for example. In some embodiments, a composition is substantially dry (e.g., in a fibrous or powdered form). In certain embodiments, a dry composition comprises a water content of less than 5%, less than 2%, less than 1%, less than 0.5% or less than 0.1%. In certain embodiments, a dry composition comprises an alcohol or organic solvent content of less than 5%, less than 2%, less than 1%, less than 0.5% or less than 0.1%.

Collagen

In some embodiments, a composition comprises collagen. In certain embodiments, collagen comprises collagen fibers. In some embodiments, collagen is partially or completely hydrolyzed collagen. In some embodiments, collagen is an acid treated collagen. In some embodiments, collagen comprises a limed collagen or collagen subjected to a liming process. In some embodiments, collagen is provided as a collagen composition comprising collagen and tricalcium phosphate. In certain embodiments, a collagen composition comprises collagen and porous tricalcium phosphate crystals. Porous tricalcium phosphate crystals may comprise a single size of crystals or different sizes of crystals non limiting examples of which include tricalcium phosphate crystals having a mean, average or absolute diameter in a range of 4 μm to 6 mm, 4-50 μm, 50-150 μm, 100-300 μm, 500-1000 μm, 1-3 mm, 3-6 mm, or intermediate ranges thereof.

In some embodiments, a composition comprises collagen in an amount in a range of 0.1-70% wt/wt (wt of collagen/total wt of composition). In some embodiments, a composition comprises collagen in an amount in a range of 0.1-70% (wt/dry wt) (wt of collagen/total dry wt of composition). In some embodiments, a composition comprises collagen in an amount in a range of 30-70%, 40-65% or 50-60% (wt/wt). In some embodiments, a composition comprises collagen in an amount of about 50-60% (wt/wt) or 50-60% (wt/dry wt). In some embodiments, a composition comprises pure collagen.

In some embodiments, a composition comprises collagen in an amount in a range of 0.01-10%, 0.01-5%, 0.01-1%, 0.05-0.5% or 0.05-0.12% (wt/wt). In some embodiments, a composition comprises collagen in an amount of about 0.1% (wt/wt). In some embodiments, a composition disclosed herein does not comprise collagen.

Hyaluronic Acid

In some embodiments, a composition comprises a suitable hyaluronic acid (HA). In some embodiments, a composition comprises HA in an amount in a range of 10% to 80%, 20% to 40%, 25% to 35%, or 26% to 30% (wt/wt). In some embodiments, a composition comprises HA in an amount in a range of 10% to 40%, 20% to 40%, 25% to 35%, or 26% to 30% (wt/dry wt). In some embodiments, a composition comprises HA in an amount of 27-30% (wt/dry wt).

In some embodiments, a composition comprises HA in an amount in a range of 0.01%-10%, 0.1% to 5%, 0.1% to 1%, 0.2% to 0.9%, or 0.3% to 0.8% (wt/wt) or (wt/vol). In some embodiments, a composition comprises HA in an amount in a range of 0.5%-0.6 (wt/wt).

In some embodiments, a composition disclosed herein does not comprise hyaluronic acid.

Sugars

In some embodiments, a composition comprises one or more sugars, non-limiting examples of which include mannose, galactose, N-acetylglactosamine, N-acetylglucosamine, N-acetylneuraminic acid, fucose, xylose and combination thereof. In some embodiments, a composition comprises a sugar in an amount in a range of 0.001%-35%. In some embodiments, a composition comprises a sugar in an amount in a range of about 0.001% to 5%, about 0.005% to 5%, about 0.01% to 0.5% or about 0.05-0.2% (wt/vol). In some embodiments, a composition comprises a sugar in an amount in a range of about 5%-35%, 10%-30%, 15%-30% or 20-25% (wt/wt) or (wt/dry wt).

In some embodiments, a composition comprises fucose. In some embodiments, a composition comprises fucose in an amount in a range of 0.01%-25%, 0.05%-15%, 0.05% to 2% or 8-15% (wt/wt), or intermediate ranges thereof.

Metals

In some embodiments, a composition comprises a metal, or a salt thereof, non-limiting examples of which include copper (Cu), gold (Au), silver (Ag), platinum (Pt), iron (Fe), zinc, selenium, manganese, cobalt, chromium, boron, molybdenum, silicon, nickel, vanadium and combinations thereof. In some embodiments, a composition comprises one or more metals, or a suitable salt thereof, in an amount in a range of 0.00001-10%, 0.0001-10%, 0.0001-5%, 0.001-5%, 0.01-5%, 0.5%-15%, 1%-10%, 1%-5%, 2%-3% (wt/wt) or intermediate ranges thereof. In some embodiments, a composition comprises one or more metals, or salts thereof, each at a concentration in a range of about 1% to 15%, about 2% to 10%, or about 5% to 10% (wt/dry wt). In some embodiments, one or more of these may be in ionic form.

In some embodiments, a composition comprises one or more metals, each at a concentration in a range of about 0.001% to 1%, about 0.01% to 1%, or about 0.01% to 0.1% (wt/wt). In some embodiments, a composition is a wet composition (e.g., a paste, gel or liquid) and comprises one or more metals, each at a concentration in a range of about 0.001% to 1%, about 0.01% to 1%, or about 0.01% to 0.1% (wt/vol). In some embodiments, a metal, or salt thereof, is present in a composition in the form of a particle or nanoparticle. In some embodiments, a composition comprises copper (Cu), gold (Au), silver (Ag), platinum (Pt) and/or, iron (Fe).

In some embodiments, a suitable salt of Cu is selected from CuCl, $CuCl_2$ and $CuCl_3$. In some embodiments, a composition comprises Cu, or a suitable salt thereof, in an amount in a range of 0.001-15%, 0.001%-10%, 0.001%-5%, 0.001%-0.1%, 0.01-1%, 0.5%-15%, 1%-10%, 1%-5%, 2%-3%, or intermediate ranges thereof. In some embodiments, a composition comprises Cu, or a suitable salt thereof, in an amount in a range of 0.01-1%.

In some embodiments, a suitable salt of Au is selected from AuCl, $AuCl_2$, $AuCl_3$ and $Au_2O_3$. In some embodiments, a composition comprises Au, or a suitable salt thereof, in an amount in a range of 0.001-15%, 0.001%-10%, 0.001%-5%, 0.001%-0.1%, 0.01-1%, 0.5%-15%, 1%-10%, 1%-5%, 2%-3%, 4%-10% (wt/wt) or (wt/dry wt), or intermediate ranges thereof.

In some embodiments, a suitable salt of silver (Ag) is selected from AgCl, $AgCl_2$ and $AgNO_3$. In some embodiments, a composition comprises Ag, or a suitable salt thereof, in an amount in a range of 0.001-15%, 0.001%-10%, 0.001%-5%, 0.001%-0.1%, 0.01-1%, 0.5%-15%, 1%-10%, 1%-5%, 2%-3%, 4%-10% (wt/wt) or (wt/dry wt), or intermediate ranges thereof.

In some embodiments, a suitable salt of platinum (Pt) is selected from $PtCl_2$, $PtCl_4$, $PtBr_2$ and $PtI_2$. In some embodiments, a composition comprises Pt, or a suitable salt thereof, in an amount in a range of 0.001-15%, 0.001%-10%, 0.001%-5%, 0.001%-0.1%, 0.01-1%, 0.5%-15%, 1%-10%, 1%-5%, 2%-3%, 4%-10% (wt/wt) or (wt/dry wt), or intermediate ranges thereof.

In some embodiments, a suitable salt of iron (Fe) is selected from $FeCl_3$ or $FeCl_2$. In some embodiments, a composition comprises Fe, or a suitable salt thereof, in an amount in a range of 0.001-15%, 0.001%-10%, 0.001%-5%, 0.001%-0.1%, 0.01-1%, 0.5%-15%, 1%-10%, 1%-5%, 2%-3%, 4%-10% (wt/wt) or (wt/dry wt), or intermediate ranges thereof.

Salts & Electrolytes

In some embodiments, a composition comprises one or more salts or electrolytes, non-limiting examples of which include calcium chloride, choline chloride, magnesium sulfate, potassium chloride, potassium phosphate (monobasic), sodium bicarbonate, sodium chloride, sodium iodide, the like or combinations thereof.

Nucleotides

In some embodiments, a composition comprises one or more nucleotides, non-limiting examples of which include ADP, ATP, cAMP, CTP, TTP, GTP, pppGpp, the like and combinations thereof. In some embodiments, a composition comprises ATP. In some embodiments, a composition comprises a nucleotide in an amount in a range of 0.001-35% (wt/wt or wt/dry wt).

In some embodiments, a composition comprises a nucleotide in an amount in a range of 0.001%-10%, 0.001%-1%, 0.01%-1%, 0.05-0.3% or 0.05-0.15% (wt/wt) or intermediate ranges thereof. In some embodiments, a composition is a wet composition (e.g., a paste, gel or liquid) and comprises a nucleotide in an amount in a range of 0.001%-10%, 0.001%-1%, 0.01%-1%, 0.05-0.3% or 0.05-0.15% (wt/vol) or intermediate ranges thereof. In some embodiments, a composition comprises a nucleotide in an amount in a range of 5%-35%, 10%-30%, 15%-30% or 20-25% (wt/dry wt). In some embodiments, a composition is a dry composition (e.g., powder, a fibrous mass) and comprises a nucleotide in an amount in a range of 5%-35%, 10%-30%, 15%-30% or 20-25% (wt/dry wt).

In some embodiments, a composition comprises ATP in an amount in a range of 0.001%-10%, 0.001%-1%, 0.01%-1%, 0.05-0.3% or 0.05-0.15% (wt/wt) or in an amount in a range of 5%-35%, 10%-30%, 15%-30% or 20-25% (wt/dry wt).

In some embodiments, a composition comprises one or more free bases, non-limiting examples of which include adenosine, uridine, guanosine, iridine and cytidine. In some embodiments, a composition comprises one or more free bases each in an amount in a range of 0.001-35% (wt/wt or wt/dry wt).

Acetylcholine

In some embodiments, a composition comprises acetylcholine (ACh). In some embodiments, a composition comprises ACh in an amount in a range of 0.001%-10%, 0.001%-1%, 0.01%-1%, 0.05-0.3% or 0.05-0.15% (wt/wt) or intermediate ranges thereof. In some embodiments, a composition is a wet composition (e.g., a paste, gel or liquid) and comprises ACh in an amount in a range of 0.001%-10%, 0.001%-1%, 0.01%-1%, 0.05-0.3% or 0.05-0.15% (wt/vol) or intermediate ranges thereof. In some embodiments, a composition comprises ACh in an amount in a range of 5%-35%, 10%-30%, 15%-30% or 20-25% (wt/dry wt). In some embodiments, a composition is a dry composition (e.g., powder, a fibrous mass) and comprises ACh in an amount in a range of 5%-35%, 10%-30%, 15%-30% or 20-25% (wt/dry wt).

Acids

In some embodiments, a composition comprises an acid. In some embodiments, a composition comprises hydrochloric acid (HCl) or glycine-HCL in an amount in a range of 0.0001-60%, 0.0001%-10%, 0.0001%-5%, 0.0001%-1%, 0.0001%-0.1%, 0.0005%-0.1%, 0.001-0.1%, 5%-15%, 1%-10%, 1%-5%, 2%-3% (wt/wt) or intermediate ranges thereof. In some embodiments, a composition comprises hydrochloric acid (HCl) or glycine-HCL in an amount in a range of 0.0001-1.0%, 0.0001-0.75%, 0.0005-0.75%, or 0.0005-0.5% (wt/wt).

In some embodiments, a composition comprises a pH in a range of 2 to 8, 3 to 7, 3.5-7 or 4 to 6. In some embodiments, a composition comprises a pH in a range of 2-7, 2-6, 2-5, 2-4, 2-3 or 2.5-4. In some embodiments, a composition is a dry composition (e.g., a powder or fibrous mass) and comprises a pH in a range of 1-4, 1.5-3.5 or 2-3. In some embodiments, a composition is a wet composition (e.g., a slurry, gel, paste or liquid) and comprises a pH in a range of 1-8, 2-8 or 3-7.

In some embodiments, a composition comprises benzoic acid. In some embodiments, a composition comprises benzoic acid in an amount in a range of 0.001-25%, 0.001%-10%, 0.001%-5%, 0.001%-0.1%, 0.01-1%, 0.5%-15%, 1%-10%, 1%-5%, 2%-3% (wt/wt) or intermediate ranges thereof.

Water

In some embodiments, a composition comprises a water content in a range of 0%-90%, 0% to 20%, or 0% to 10%, or 0% to 5% (wt/wt). In some embodiments, a composition is substantially dry (e.g., a powder, granules, a fibrous mass) and comprises a water content in a range of less than 5%, less than 2%, less than 1%, less than 0.5% or less than 0.1%. In certain embodiments, a composition is substantially dry (e.g., a powder, granules, a fibrous mass) and comprises an alcohol or organic solvent content of less than 5%, less than 2%, less than 1%, less than 0.5% or less than 0.1%.

Hydroxyapatite

In some embodiments, a composition comprises hydroxyapatite. Hydroxyapatite may be of a suitable size and a suitable form. In some embodiments, a composition comprises hydroxyapatite in the form of crystals which may be dense or porous.

Amino Acids

In some embodiments, a composition comprises one or more amino acids. In some embodiments, a composition comprises one or more essential amino acids. In some embodiments, a composition comprises lysine, proline, isoleucine, leucine, methionine, phenylalanine, threonine, tryptophan, valine and/or histidine. In some embodiments, a composition comprises one or more non-essential amino acids, non-limiting examples of which include alanine, arginine, aspartate, glutamate, glycine, serine and proline.

Fatty Acids

In some embodiments, a composition comprises one or more fatty acids, non-limiting examples of which include linoleic acid (LA) and/or alpha-linolenic acid (ALA).

Vitamins

In some embodiments, a composition comprises one or more vitamins, non-limiting examples of which include vitamin A, vitamin $D_2$, vitamin $D_3$, vitamin E, vitamin $K_1$, vitamin $K_2$, vitamin B1, vitamin B2, vitamin B3, vitamin B5, vitamin B6, vitamin B7, vitamin B9, vitamin C and vitamin $B_{12}$ (methylcobalamin, hydroxocobalamin).

Other Supplements

In some embodiments, a composition comprises cholesterol, diacylglycerol (DAG), diglycerol, and/or pantothenic acid.

Exemplary Compositions

In some embodiments, a composition comprises one or more ingredients selected from collagen, hyaluronic acid, a metal or salt thereof, a sugar (e.g., fucose), a nucleotide (e.g., ATP), ACh, water, an acid, fucose, an amino acid, a vitamin, a fatty acid, hydroxyapatite, and an electrolyte. In some embodiments, a composition comprises HA, and one or more of collagen, fucose, copper, and iron. In some embodiments, a composition comprises HA, and one or more of collagen, fucose, copper, and iron.

In some embodiments, a composition comprises a formulation shown in any one of FIGS. 35-47. In some embodiments, a composition comprises hyaluronic acid (HA)(Formula 1). In some embodiments, a composition comprises hyaluronic acid (HA) and fucose (Formula 2). In some embodiments, a composition comprises hyaluronic acid (HA) and copper (Formula 3). In some embodiments, a composition comprises hyaluronic acid (HA) and iron (Formula 4). In some embodiments, a composition comprises hyaluronic acid (HA) and silver (Formula 5). In some embodiments, a composition comprises hyaluronic acid (HA) and gold (Formula 6). In some embodiments, a composition comprises HA and collagen (Formula 7). In some embodiments, a composition comprises HA and ATP (Formula 8). In some embodiments, a composition comprises HA and ACh (Formula 9). In some embodiments, a composition comprises HA, fucose and ATP (Formula 10). In some embodiments, a composition comprises HA, fucose and ACh (Formula 11). In some embodiments, a composition comprises HA, fucose and copper (Formula 12). In some embodiments, a composition comprises HA, fucose and iron (Formula 13). In some embodiments, a composition comprises HA, fucose and silver (Formula 14). In some embodiments, a composition comprises HA, fucose and gold (Formula 15). In some embodiments, a composition comprises HA, copper and gold (Formula 16). In some embodiments, a composition comprises HA, collagen, copper and gold (Formula 17). In some embodiments, a composition comprises HA, collagen, copper, gold and ATP (Formula 18). In some embodiments, a composition comprises HA, collagen, copper, gold, ATP and iron (Formula 19). In some embodiments, a composition comprises HA, collagen, copper, gold, ATP, iron and silver (Formula 20). In some embodiments, a composition comprises HA, fucose, collagen, copper, gold, ATP, iron and silver (Formula 21). In some embodiments, a composition comprises fucose (Formula 22). In some embodiments, a composition comprises collagen (Formula 23).

In some embodiments, a composition comprises HA in an amount of 0.3-1.2% (wt/vol); optionally collagen in an amount of 0.05-0.2% (wt/vol); iron or a salt thereof in an amount of 0.015-0.06% (wt/vol) and copper or a salt thereof in an amount of 0.015-0.06% (wt/vol). In some embodiments, a composition is a wet composition formulated for topical or local administration and comprises HA in an amount of 0.3-1.2% (wt/vol); optionally collagen in an amount of 0.05-0.2% (wt/vol); iron or a salt thereof in an amount of 0.015-0.06% (wt/vol) and copper or a salt thereof in an amount of 0.015-0.06% (wt/vol).

In some embodiments, a composition comprises collagen in an amount of 50-70% (wt/wt); optionally HA in an amount of 25-35% (wt/wt); iron or a salt thereof in an amount of 4.5-10% (wt/wt) and copper or a salt thereof in an amount of 4.5-10% (wt/wt). In some embodiments, a composition is a substantially dry composition formulated for topical or local administration and comprises collagen in an amount of 50-70% (wt/wt); optionally HA in an amount of 25-35% (wt/wt); iron or a salt thereof in an amount of 4.5-10% (wt/wt) and copper or a salt thereof in an amount of 4.5-10% (wt/wt).

In some embodiments, a composition does not comprise collagen. In some embodiments, a composition does not comprise HA. In some embodiments, a composition does not comprise fucose. In some embodiments, a composition does not comprise copper. In some embodiments, a composition does not comprise silver. In some embodiments, a composition does not comprise iron. In some embodiments, a composition does not comprise gold. In some embodiments, a composition does not comprise ATP. In some embodiments, a composition does not comprise ACh.

Pharmaceutical Compositions & Formulations

In some embodiments, a pharmaceutical composition comprises a therapeutically effective amount of a composition disclosed herein. In some embodiments provided herein is a pharmaceutical composition use in conducting a method described herein. In some embodiments, a pharmaceutical composition comprises a pharmaceutically acceptable excipient, diluent, additive or carrier.

A pharmaceutical composition can be formulated for a suitable route of administration. In some embodiments a pharmaceutical composition is formulated for oral, subcutaneous (s.c.), intradermal, intramuscular, intraperitoneal and/or intravenous (i.v.) administration. In certain embodiments, a pharmaceutical composition contains formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants. In particular, a pharmaceutical composition can comprise any suitable carrier, formulation, or ingredient, the like or combinations thereof as listed in "Remington: The Science And Practice Of Pharmacy" Mack Publishing Co., Easton, PA, 19$^{th}$ Edition, (1995)(hereafter, Remington '95), or "Remington: The Science And Practice Of Pharmacy", Pharmaceutical Press, Easton, PA, 22$^{nd}$ Edition, (2013)(hereafter, Remington 2013), the contents of which are incorporated herein by reference in their entirety.

In certain embodiments, a pharmaceutical composition comprises a suitable excipient, non-limiting examples of which include anti-adherents (e.g., magnesium stearate), a binder, fillers, monosaccharides, disaccharides, other carbohydrates (e.g., glucose, mannose or dextrin), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapol), stability enhancing agents (such as sucrose or sorbitol), and tonicity enhancing agents (such as alkali metal halides, sodium or potassium chloride, mannitol, sorbitol), and/or any excipient disclosed in Remington '95 or Remington 2013. The term "binder" as used herein refers to a compound or ingredient that helps keeps a pharmaceutical mixture combined. Suitable binders for making pharmaceutical formulations and are often used in the preparation of pharmaceutical tablets, capsules and granules are known to those skilled in the art.

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agent include those having a sulfhydryl group (e.g., a thiol) such as N-acetylcysteine, N-acetyl homocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutyl hydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non-limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide derivative, such as chlorohexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE®. A preservative can comprise polyglycol-polyamine condensation resins, such as known and commercially available under the trade name POLYQUART® from Henkel KGaA. A preservative can comprise stabilized hydrogen peroxide. A preservative can be benzalkonium chloride. In some embodiments a pharmaceutical composition is free of preservatives.

In some embodiments a pharmaceutical composition is substantially free of contaminants (e.g., blood cells, platelets, polypeptides, minerals, blood-borne compounds or chemicals, virus, bacteria, other pathogens, toxin, and the like). In some embodiments a pharmaceutical composition is substantially free of serum and serum contaminants (e.g., serum proteins, serum lipids, serum carbohydrates, serum antigens and the like). In some embodiments a pharmaceutical composition is substantially free of a pathogen (e.g., a virus, parasite or bacteria). In some embodiments a pharmaceutical composition is substantially free of endotoxin. In some embodiments a pharmaceutical composition is sterile.

The pharmaceutical compositions described herein may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parenteral administration may contain one or more excipients. In some embodiments a pharmaceutical composition is lyophilized to a dry powder form. In some embodiments a pharmaceutical composition is lyophilized to a dry powder form, which is suitable for reconstitution with a suitable pharmaceutical solvent (e.g., water, saline, an isotonic buffer solution (e.g., PBS), DMSO, combinations thereof and the like). In certain embodiments, reconstituted forms of a lyophilized pharmaceutical composition are suitable for parenteral administration (e.g., intravenous administration) to a mammal.

In certain embodiments, a pharmaceutical composition is configured for oral administration and may be formulated as a tablet, microtablet, minitablets, micropellets, powder, granules, capsules (e.g., capsules filled with microtablets, micropellets, powders or granules), emulsions, solutions, the like or combinations thereof. Pharmaceutical compositions configured for oral administration may comprise suitable coatings to delay or sustain release of the active ingredient, non-limiting examples of which include enteric coatings such as fatty acids, waxes, shellac, plastics, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, cellulose acetate trimellitate, sodium alginate, zein, plant fibers, the like and combinations thereof.

In some embodiments a pharmaceutical compositions described herein may be configured for topical administration and may include one or more of a binding and/or lubricating agent, polymeric glycols, gelatins, cocoa-butter or other suitable waxes or fats. In some embodiments a pharmaceutical composition described herein is incorporated into a topical formulation containing a topical carrier that is generally suited to topical drug administration and comprising any suitable material known to those skilled in the art. In certain embodiments, a topical formulation of a pharmaceutical composition is formulated for administration using a topical patch. A pharmaceutical composition, in some embodiments, is a foam, paste or gel.

In certain embodiments, an optimal pharmaceutical composition is determined by one skilled in the art depending upon, for example, on the intended route of administration, delivery format and desired dosage (see e.g., Remington '95 or Remington 2013, supra). A pharmaceutical composition can be manufactured by any suitable manner, including, e.g., by means of conventional mixing, dissolving, granulating, dragee-making, levigating, emulsifying, encapsulating, entrapping or tableting processes (e.g., see methods described in Remington '95 or Remington 2013).

Route of Administration

Any suitable method of administering a composition or pharmaceutical composition disclosed herein to a subject can be used. Any suitable formulation and/or route of administration can be used for administration of a composition disclosed herein (e.g., see Fingl et al. 1975, in "The Pharmacological Basis of Therapeutics", which is incorporated herein by reference in its entirety). A suitable formulation and/or route of administration can be chosen by a medical professional (e.g., a physician) in view of, for example, a subject's risk, age, and/or condition. Non-limiting examples of routes of administration include topical or local (e.g., transdermal or cutaneous, (e.g., on the skin or epidermis), in or on the eye, intranasally, transmucosal, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like or combinations thereof.

In some embodiments a pharmaceutical composition described herein is administered to the lungs, bronchial passages, trachea, esophagus, sinuses, or nasal passages using a suitable method, non-limiting examples of which include intranasal administration, intratracheal instillation, and oral inhalative administration (e.g., by use of an inhaler, e.g., single/-multiple dose dry powder inhalers, nebulizers, and the like).

Compositions for use according to the methods of the invention can be, in some embodiments, aerosolized compositions. The aerosolized composition can be formulated such that the composition has increased solubility and/or diffusivity. Solutions to be aerosolized can be prepared in any suitable form, for example, either as liquid solutions or suspensions, as emulsions, or in solid forms suitable for dissolution or suspension in liquid prior to aerosol production and inhalation. For administration by inhalation, the compositions described herein can conveniently be delivered in the form of an aerosol (e.g., through liquid nebulization, dry powder dispersion or meter-dose administration. The aerosol can be delivered from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of a composition described herein and a suitable powder base such as lactose or starch.

For aqueous and other non-pressurized liquid systems, a variety of nebulizers (including small volume nebulizers) can be used to aerosolize the formulations. Compressor-driven nebulizers can utilize jet technology and can use compressed air to generate the liquid aerosol. Such devices are commercially available from, for example, Healthdyne Technologies, Inc.; Invacare, Inc.; Mountain Medical Equipment, Inc.; Pari Respiratory, Inc.; Mada Medical, Inc.; Puritan-Bennet; Schuco, Inc., DeVilbiss Health Care, Inc.; and Hospitak, Inc. Ultrasonic nebulizers generally rely on mechanical energy in the form of vibration of a piezoelectric crystal to generate respirable liquid droplets and are commercially available from, for example, Omron Healthcare, Inc. and DeVilbiss Health Care, Inc. Vibrating mesh nebulizers rely upon either piezoelectric or mechanical pulses to generate respirable liquid droplets. Commercial examples of nebulizers that could be used in certain embodiments include RESPIRGARD II®, AERONEB®, AERONEB® PRO, and AERONEB® GO produced by Aerogen; AERX® and AERX ESSENCE™ produced by Aradigm; PORTA-NEB®, FREEWAY FREEDOM™, Sidestream, Ventstream and I-neb produced by Respironics, Inc.; and PARI LC-PLUS®, PARI LC-STAR®, and e-Flow7m produced by PARI, GmbH. By further non-limiting example, U.S. Pat. No. 6,196,219 is hereby incorporated by reference in its entirety.

In some embodiments a composition or a pharmaceutical composition disclosed herein is provided to a subject. For example, a composition that is provided to a subject is sometimes provided to a subject for self-administration or for administration to a subject by another (e.g., a non-medical professional). As another example, a composition can be provided as an instruction written by a medical practitioner that authorizes a patient to be provided a composition or treatment described herein (e.g., a prescription). In yet another example, a composition can be provided to a subject where the subject self-administers a composition orally, intravenously or by way of an inhaler, for example.

Alternately, one can administer a composition disclosed herein in a local rather than a systemic manner, for example, via direct application to a wound, skin, mucous membrane or region of interest for treating, including using a depot or sustained release formulation.

In certain embodiments a composition or pharmaceutical composition disclosed herein is administered alone, or is administered in combination with one or more additional active ingredients (AI) or active pharmaceutical ingredient (API).

Dose and Therapeutically Effective Amount

In some embodiments, an amount of a composition disclosed herein (e.g., in a pharmaceutical composition) is a therapeutically effective amount. In certain embodiments, a pharmaceutical composition comprises a therapeutically effective amount of a composition disclosed herein. In some embodiments, a therapeutically effective amount of a composition disclosed herein is administered to a subject. In some embodiments, a therapeutically effective amount of a composition disclosed herein is an amount needed to obtain an effective therapeutic outcome. In certain embodiments, a therapeutically effective amount of a composition disclosed herein is an amount sufficient to treat a wound. Determination of a therapeutically effective amount is well within the capability of those skilled in the art, especially in light of the detailed disclosure provided herein.

In certain embodiments, a therapeutically effective amount is an amount high enough to provide an effective therapeutic effect (e.g., a beneficial therapeutic effect) and an amount low enough to minimize unwanted adverse reactions. Accordingly, in certain embodiments, a therapeutically effective amount of a composition disclosed herein may vary from subject to subject, often depending on age, weight, general health condition of a subject and severity of a condition being treated. Thus, in some embodiments, a therapeutically effective amount is determined empirically. Accordingly, a therapeutically effective amount of a composition that is administered to a subject can be determined by one of ordinary skill in the art based on amounts found effective in animal or clinical studies, a physician's experience, and suggested dose ranges or dosing guidelines, for example.

In certain embodiments, a therapeutically effective amount of a composition disclosed herein is administered at a suitable dose (e.g., at a suitable volume, frequency and/or concentration, which often depends on a subject's weight, age and/or condition) intended to obtain an acceptable therapeutic outcome. In certain embodiments, a therapeutically effective amount of a composition comprises one or more doses selected from at least 0.01 mg/kg (e.g., mg of a composition per kg body weight of a subject), at least 0.1 mg/kg, at least 0.5 mg/kg, at least 1 mg/kg, at least 10 mg/kg or at least 100 mg/kg. In certain embodiments, a therapeutically effective amount of a composition is selected from one or more doses of about 0.001 mg/kg (e.g., mg of a composition per kg body weight of a subject) to about 5000 mg/kg, 0.01 mg/kg to 1000 mg/kg, 0.01 mg/kg to 500 mg/kg, 0.1 mg/kg to 1000 mg/kg, 1 mg/kg to 1000 mg/kg, 10 mg/kg to 1000 mg/kg, 100 mg/kg to 1000 mg/kg, 0.1 mg/kg to 500 mg/kg, 0.1 mg/kg to 250 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg, 0.5 mg/kg to 5 mg/kg, intervening amounts and combinations thereof. In some aspects a therapeutically effective amount of a composition administered to a subject comprises one or more doses of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 50 mg/kg, 100 mg/kg, 500 mg/kg, and intervening amounts and combinations thereof. In some embodiments a therapeutically effective amount of a composition disclosed herein is between about 0.1 mg/kg and about 50 mg/kg.

In certain embodiments, a therapeutically effective amount of a composition disclosed herein is administered at a suitable volume intended to obtain an acceptable therapeutic outcome. For example, in some embodiments, a composition herein is administered directly and/or topically to a damaged tissue. Accordingly, in some embodiments, a therapeutically effective amount of a composition comprises 0.01 ml to 50 ml/cm$^2$, or about 0.1 ml to 10 ml/cm$^2$ (ml of composition/surface area of damaged tissue).

In some embodiments administering a therapeutically effective amount of a composition comprises administering a suitable dose at a frequency or interval as needed to obtain an effective therapeutic outcome. In some embodiments administering a therapeutically effective amount of a composition disclosed herein comprises administering a suitable dose hourly, every two hours, every 4 hours, every 6 hours, three times a day, twice a day, once a day, six times a week, five times a week, four times a week, three times a week, twice a week, weekly, at combinations thereof, and/or at regular or irregular intervals thereof, and/or simply at a frequency or interval as needed or recommended by a medical professional. In some embodiments, a therapeutically effective amount of a composition is administered continuously by, for example by intravenous administration.

In some embodiments a therapeutically effective amount of a composition is administered to a subject prior to, during and/or after a subject receives a thrombolytic, anti-coagulant or endovascular intervention therapy. In some embodiments a therapeutically effective amount of a composition is administered to a subject up to 3 days prior to, up to 2 days prior to, up to 1 day prior to, up to 20 hours prior to, up to 15 hours prior to, up to 10 hours prior to, up to 5 hours prior to, up to 2 hours prior to or up to 1 hour prior to administration of a thrombolytic, anti-coagulant or endovascular intervention therapy. In some embodiments a therapeutically effective amount of a composition is administered to a subject 0 to 72 hours, 0 and 48 hours, 0 to 24 hours, 0 to 12 hours, 0 to 6 hours, 0 to 4 hours, or 0 to 2 hours before administration of a thrombolytic, anti-coagulant or endovascular intervention therapy. In some embodiments a therapeutically effective amount of a composition is administered during administration of a thrombolytic, anti-coagulant or endovascular intervention therapy. In some embodiments a therapeutically effective amount of a composition is administered intermittently or continuously for up to 1 hour after, 2 hours after, 4 hours after, 6 hours after, 12 hours after, 24 hours after, 2 days after, 3 days after, a week after, 1 month after, 3 months after, 6 months after, 12 months after, 18 months after, 24 months after or up to 36 months administration of a thrombolytic, anti-coagulant or endovascular intervention therapy.

In some embodiments, a therapeutically effective amount of energy (e.g., laser energy, light from a light emitting diode, radiofrequency (RF) energy, audio frequency energy, etc.) is administered to a damaged tissue, with or without a composition disclosed herein. In some embodiments, a therapeutically effective amount of energy comprises a dose of about 1 Joule/cm$^2$ to about 400 Joule/cm$^2$, about 1 Joule/cm$^2$ to about 150 Joule/cm$^2$, about 1 Joule/cm$^2$ to about 100 Joule/cm$^2$, about 10 Joule/cm$^2$ to about 150 Joule/cm$^2$, or about 20 Joule/cm$^2$ to about 100 Joule/cm$^2$ (energy of electromagnetic radiation per surface area of damaged tissue).

Systems

In some embodiments, one or more present systems may include one or more of the energy sources and/or devices described herein, one or more of the compositions described herein, an imaging device, and/or other components. By way of a non-limiting example, a system may include an LED, a laser, an audio, and/or an RF or audio source (e.g., any one of those by itself, any combination of two of those, a combination of three, or a combination of all four), and/or one or more (e.g., one, two, three, or more) of the compositions described herein, an imaging device, and/or other components.

The present systems may be configured to provide relatively low level energy therapy compared to prior systems. The present systems may be configured such that therapeutic light (photonic electrons and/or other electrons), RF, audio, and/or other electromagnetic energy is absorbed by, but not limited to, chromophores found in units of matter such as, but not limited to atoms, cells, and/or tissue of wounded, cancerous, diseased, aged, aging, damaged, infected, mature, immature, normal, abnormal, undersized, missing and/or contaminated atoms, cells, and/or tissue, to trigger biological reactions that result in beneficial therapeutic outcomes. In some embodiments, the present systems may be configured such that one or more compositions included in a given system are configured to accept photonic electrons, electrons, and/or other energy and to serve as a reservoir of building blocks to assist in new cell organization and to generate new tissue. The present system(s) are configured to increase chromophore activity and thus increase cell proliferation, cell migration and generate units of matter such as, but not limited to tissue. This may assist protein synthesis to regenerate and/or biostimulate units of matter such as, but not limited to tissue, while exhibiting effects such as but not limited to decreasing pain at or surrounding the treatment site and/or decontaminating the tissue at or surrounding the treatment site.

In a natural in vivo state, a chromophore such as but not limited to, cytochrome c oxidase exists within the mitochondria of cells and exhibits chromophore activity which may lead to reactions, such as, but not limited to biological reactions. Increased chromophore activity is exhibited via utilization of excited photons (photonic electrons) and/or electrons following their delivery to, but not limited to, chromophores and other units of matter such as, but not limited to atoms, cells, and/or tissue of wounded, cancerous, diseased, aged, aging, damaged, infected, mature, immature, normal, abnormal, undersized, missing and/or contaminated atoms, cells, and/or tissue. The utilization of excited photons (photonic electrons), other electrons, and/or other energy leads causes atomic, cellular, and/or tissue generation and/or repair. The energy delivered to units of matter such as, but not limited to tissue, is conserved.

The delivery of photons (photonic electrons), electrons, and/or other energy and the consequent downstream effect comprises photochemistry and if the energy of the photonic electrons and/or electrons delivered is bio-cell friendly by using specific bio-cell friendly parameters, covalent bonds are not broken and the delivered energy is conserved within the biological system. Additionally, if the energy delivered is not only conserved, but is additionally sufficient for a first excited singlet state to be formed, the absorbed electrons can undergo intersystem crossing until the electrons reach the long-lived triplet state within the chromophore. This long life allows an increased amount of reactions to occur once photonic electrons and/or electrons are delivered into units of matter such as, but not limited to, tissue.

These electron transfer reactions are relevant in the mitochondrial respiratory chain as follows: the inner mitochondrial membrane contains five membrane protein complexes: NADH dehydrogenase (Complex I), succinate dehydrogenase (Complex II), cytochrome c reductase (Complex III), cytochrome c oxidase (Complex IV), ATP synthase (Complex V), and two molecules that freely diffuse, ubiquinone and cytochrome c. The freely diffusible molecules shuttle photonic electrons and/or electrons from one complex to the next. Insertion of photonic electrons (photons), electrons, and/or other energy into the outer orbital of an atom increases the shuttling rate of electrons between and among the complexes.

For example, the respiratory chain accomplishes the stepwise transfer of photonic electrons and/or electrons from NADH and FADH2 (produced in the citric acid cycle also known as the Krebs cycle) to oxygen molecules to form water molecules. These newly formed water molecules, now harnessing this electron transfer energy, release this energy and transfer it to the pumping of protons (H+) from the matrix to the intermembrane space. The gradient of protons formed in the mitochondria across the inner membrane by this process of active transport of photonic electrons and/or electrons forms a miniature battery. Protons are able to flow back down this gradient, re-entering the matrix, through another protein complex of the inner membrane, the ATP synthase complex. The example shows that energy is unlikely to escape once in the mitochondrial system, and is thus conserved for usage by the living system.

Furthermore, the absorption of photonic electrons (photons) and/or electrons (and/or other radiation and/or energy from an energy source device as described herein) by molecules such as chromophore molecules leads to electronically excited states, and consequently leads to an acceleration of electron transfer reactions. The more reduced an initial cell's state, the higher the potential to respond to electron transfer. Notably, cells at the optimal redox state respond weakly or do not respond.

Units of matter such as, but not limited to, atoms, cells, and/or tissue of wounded, cancerous, diseased, aged, aging, damaged, infected, mature, immature, normal, abnormal, undersized, missing and/or contaminated atoms, cells, and/or tissue having reduced ATP production to no ATP production, commonly exist in a reduced, severely reduced or completely reduced state, thereby significantly exhibit an increased affinity of varying degrees of accepting electron transfers. Cytochromes (enzymes) within mitochondria of units of matter such as, but not limited to atoms, cells, and/or tissue of wounded, cancerous, diseased, aged, aging, damaged, infected, mature, immature, normal, abnormal, undersized, missing and/or contaminated atoms, cells, and/or tissue have a high affinity to absorb energy (photonic electrons and/or electrons). Enzymes are catalysts and are able to process thousands of substrate molecules. Energized enzymes, ones that have absorbed electrons, provide an amplified tissue response of varying degrees.

By placing at least one composition (substrate) and/or portions thereof into an excited or soon to be excited mitochondrial "manufacturing" plant, (one that has absorbed or will soon be treated and/or otherwise irradiated to absorb energy from an energy source device described herein,) the energy-chemical chromophore activity may become further increased and/or accelerated by varying degrees. Providing at least one composition and/or portions thereof, and/or energy (e.g., radiation) as described herein, and/or a combination of the two, to units of matter such as, but not limited to atoms, cells, and/or tissue of wounded, cancerous, diseased, aged, aging, damaged, infected, mature, immature, normal, abnormal, undersized, missing and/or contaminated atoms, cells, and/or tissue, enables the host units of matter such as, but not limited to atoms, cells or tissues, to partially or fully rebuild the particular atom, cell and/or tissue and/or tissue segment; depending on the length of treatment with the energy and/or the composition used, and/or the optional method of a treatment cycle.

As described herein, the present systems may be considered relatively low energy compared to prior systems. If a high energy system is used, the body's circuitry quickly begins to have a backflow of electrons, not allowing further electron deposition. This backflow (back-up) of electrons may burn or melt tissue by denaturing proteins. By keeping the system a low energy system, as described herein, the system is not limited to a certain, brief, therapeutic treatment in order to avoid unwanted tissue burning and melting. The therapeutic energy (e.g., at a certain therapeutic threshold) can be maintained for a longer period of time. Other advantages are contemplated.

The present system(s) are configured for treating units of matter such as, but not limited to atoms, cells, and/or tissue of wounded, cancerous, diseased, aged, aging, damaged, infected, mature, immature, normal, abnormal, undersized, missing and/or contaminated atoms, cells, and/or tissue, by using one or more energy sources such as but not limited to a laser photon beam, an LED photon beam, a broadband photon beam, a radiofrequency electron waveform, an electron current, an audio frequency electron waveform, and/or at least one composition and/or portions thereof.

The system(s) may be used to deliver photonic electrons and/or electrons, RF waves, audio waves, and/or other forms of energy into units of matter such as, but not limited to atoms, cells, and/or tissue of wounded, cancerous, diseased, aged, aging, damaged, infected, mature, immature, normal, abnormal, undersized, missing and/or contaminated atoms, cells, and/or tissue by using photonic electrons and/or electrons such as but not limited to a laser photon beam, and/or LED photon beam and/or broadband photon beam and/or radiofrequency electron waveform/s and/or electron current and/or at least one substrate and/or portions thereof in order to generate units of matter such as, but not limited to: tissue by using a principle such as, but not limited to, transduction and/or transference.

The system(s) also relate to the novel observation of transfection and/or transference of units of matter such as, but not limited to electrons, protons and/or proteins, into tissue that is able to accept electrons, protons and/or proteins, such as but not limited to wounded, cancerous, diseased, aged, aging, damaged, infected, mature, immature, normal, abnormal, and/or contaminated units of matter such as, but not limited to: tissue. Tissue may include vasculature, skin, muscle, nerve, bone origin that may be from ectodermal, endodermal and/or mesodermal origin, lines and/or pathways, and/or other tissue. The electrons and/or other energy may be generated by an energy source device (e.g., as described herein) configured to generate a laser photon beam, an LED photon beam, a broadband photon beam, a radiofrequency waveforms, electron current. The system may be used to add or insert photonic electrons and/or electrons into tissue that is able to accept electrons, such as but not limited to wounded, cancerous, diseased, aged, aging, damaged, infected, mature, immature, normal, abnormal, and/or contaminated units of matter such as, but not limited to tissue. In some embodiments, at least one composition and/or portion thereof may be included in the system and an associated method (described herein) may be used to generate units of matter such as, but not limited to: tissue through a process such as, but not limited to, transfection and/or transference.

In some embodiments, the system comprises a transfection and/or transference system wherein a source of energy emits photonic electrons and/or electrons that absorb into outer orbitals of atoms and subsequently produce ATP, further wherein the source of energy originates from one or more of laser photons, LED photons, broadband photons, radiofrequency electron waveforms, electron current, and/or other energy sources. Additionally, the present system may include at least one composition (substrate) and/or portions thereof. The system may be used to treat tissue such as, but not limited to wounded, cancerous, diseased, aged, aging, damaged, infected, mature, immature, normal, abnormal, and/or contaminated units of matter such as, but not limited to tissue. In some embodiments, the presents system is configured to facilitate tissue growth of such tissue by delivering the energy as described. In some embodiments, one or more of the present systems may provide for treating deeper and surrounding units of matter such as, but not limited to: tissue, by using the principle of transfection and/or transference.

In some embodiments, one or more of the systems described herein may be useful for treating tissue, imaging tissue, facilitating tissue generation, identifying biomarkers that are common between wound healing and cancer, and/or other uses. For example, a present system can be used to generate tissue by maintaining a therapeutic energy threshold while depositing electrons into outer orbitals, such that ATP is constantly pumped through cells. In the cytoplasm, the ATP is used to assemble proteins. By allowing the system to therapeutically maintain the ATP formation for duration of specific times, the present system is guides the body's cells to maintain protein assembly until tissue is formed. As another example, the stroma in solid tumors contains a variety of cellular phenotypes and signaling pathways associated with wound healing, leading to the concept that a tumor behaves as a wound that does not heal. Similarities between tumors and healing wounds include fibroblast recruitment and activation, extracellular matrix (ECM) component deposition, infiltration of immune cells, neovascularization, and cellular lineage plasticity. However, unlike a wound that heals, the edges of a tumor are constantly expanding (https://www.ncbi.nlm.nih.gov/pmc/articles/PMC6237224/). In some embodiments, a present system may be used to stop the expansion by re-establishing healthy circulation in throughout and surrounding a tumor, as the system is configured to do with other tissue. When circulation and its balanced vascular endothelial growth factor is re-established, blood vessels grow following a normal course of arteriogenesis and venogenesis, reestablishing normal patterns of growth.

In some embodiments, one or more of the devices, systems, and/or methods described herein may be used for lung imaging (e.g., for treating Covid-19 patients). For example, a Ti-sapphire laser may be configured to penetrate energy through skin to the lung tissue. Reflected, transmitted, or scattered light can be captured by a photomultiplier tube (PMT) followed by a high dynamic range oscilloscope. A laser may have a sufficient diameter for treatment of lungs to treat a two centimeter cubed area or more, a ten centimeter cubed area or more, or an entire lung or lungs, for example. In some embodiments, these areas may be covered by more than one laser. Such a laser (or lasers) may have a custom housing unit sufficient enough in size for one or more lasers. The imaging devices and/or systems may include a time stretch dispersive Fourier transform system for real-time spectral measurement. Depth of penetration, reflection, transmission, or scattering on lung tissue may be determined using PMT, a high dynamic range oscilloscope and a time stretch dispersive Fourier transform system, for example. In some embodiments, the imaging devices and/or systems may include an optical coherence tomography system. Software may provide for 3D volumetric visualization.

Methods

In some embodiments, a method comprises treating a wound or damaged tissue of a subject, which method comprises administering a therapeutically effective amount of a composition disclosed herein to the wound or damaged tissue, and/or administering a therapeutically effective amount of energy (e.g., laser energy, light from a light emitting diode, radiofrequency (RF) energy, audio frequency energy, etc.), as described herein, to the wound or damaged tissue. In some embodiments, the energy (e.g., laser energy, light from a light emitting diode, radiofrequency (RF) energy, audio frequency energy, etc.) is administered before, during and/or after administration of the composition to the wound or damaged tissue. In some embodiments, a composition is administered topically or locally. In some embodiments, a composition is administered orally.

In some embodiments, the energy (e.g., laser energy, light from a light emitting diode, radiofrequency (RF) energy, audio frequency energy, etc.) administered comprises a wavelength in a range of 200 nm to 2500 nm. In some embodiments, the energy administered comprises a wavelength in a range of 700-900 nm. In some embodiments, the energy administered comprises a wavelength in the RF range, for example a frequency in a range of between about 1 dm and 1 km. In some embodiments, a therapeutically effective amount energy administered comprises a dose of 1 to 400 joules/cm$^2$ or 10 to 100 joules/cm$^2$. In some embodiments, a therapeutically effective amount of energy that is administered to a wound or damaged tissue is administered for about 0.1 to 30 minutes. In some embodiments, a therapeutically effective amount of energy that is administered to a wound or damaged tissue is administered for about 1 to 30 min., 1 to 15 min., or for about 1 to 5 min. In some embodiments, a therapeutically effective amount of energy that is administered to a wound or damaged tissue comprises a dose of 10 to 100 joules/cm$^2$ administered for about 1 to 15 minutes at a wavelength in a range of 700-900 nm. A treatment may comprise administering one, or multiple doses of energy.

In some embodiments, a method comprises administering a therapeutically effective amount of the composition by local or systemic administration. In certain embodiments, a therapeutically effective amount of the composition is administered topically or directly to the wound or damaged tissue. In certain embodiments, a therapeutically effective amount of a composition comprises a volume in a range of 0.01 to 20 ml/cm$^2$. Accordingly, in some embodiments, a wound or damaged tissue is treated by administering 0.01 to 20 ml/cm$^2$ of a composition directly to the wound or damaged tissue and administering a therapeutic amount of energy (e.g., laser energy, light from a light emitting diode, radiofrequency (RF) energy, audio frequency energy, etc.) to the wound or damaged tissue that comprises the composition, or a portion thereof.

In certain embodiments, a therapeutically effective amount of a composition comprises a dose of about 0.1 mg/cm$^2$ to 10 gram/cm$^2$ (weight of composition/surface area of damaged tissue). Accordingly, in some embodiments, a wound or damaged tissue is treated by administering 0.1 mg/cm$^2$ to 10 gram/cm$^2$ of a composition directly to the wound or damaged tissue and administering a therapeutic amount of energy (e.g., laser energy, light from a light emitting diode, radiofrequency (RF) energy, audio frequency energy, etc.) to the wound or damaged tissue that comprises the composition, or a portion thereof. The energy acts as a delivery system of the composition and when treatment repeated, another dose is dispensed to be used on a wound or damaged tissue.

In certain embodiments, a therapeutically effective amount of a composition is administered systemically (e.g., orally or by parenteral administration) at a dose of 0.1 to 50 mg/kg (weight of composition/body weight of the subject). Accordingly, in some embodiments, a wound or damaged tissue is treated by administering a dose of 0.1 to 50 mg/kg of a composition to a subject by systemic administration followed by administering a therapeutic amount of energy (e.g., laser energy, light from a light emitting diode, radiofrequency (RF) energy, audio frequency energy, etc.) to the wound or damaged tissue.

In certain embodiments, a therapeutically effective amount of a composition is administered as a mouth wash or oral rinse, for example for treatment of damaged tissue located on the tongue or in the mouth. Accordingly, in some embodiments, 5-100 ml of a composition described herein is introduced into the mouth of a subject such that the composition contacts a damaged tissue within the mouth for a period of 0.1 to 3 minutes, followed by the subject expelling or spitting the composition from the mouth. After administering the composition, the wound or damaged tissue is treated by administering a therapeutic amount of energy (e.g., laser energy, light from a light emitting diode, radiofrequency (RF) energy, audio frequency energy, etc.) to the wound or damaged tissue.

A therapeutically effective amount of energy, in some embodiments, is administered prior to administration of a composition described herein. Accordingly, a therapeutically effective amount of energy, in some embodiments, is administered 0.1 min. to 1 hour before administration of a composition described herein. In some embodiments, a therapeutically effective amount of energy is administered 1 min. to 30 min., or 1 min. to 15 min. before administration of a composition described herein.

Kits

In some embodiments, provided herein is a kit comprising a composition disclosed herein or a pharmaceutical composition comprising a composition disclosed herein. In some embodiments, a kit comprises one or more doses of a pharmaceutical composition comprising a composition disclosed herein. In some embodiments, a kit comprises one or more packs and/or one or more dispensing devices, which can contain one or more doses of a composition disclosed herein, or pharmaceutical composition thereof, as described herein. Non-limiting examples of a pack include a metal, glass, or plastic container, syringe or blister pack that comprises a composition disclosed herein or a composition described herein. In certain embodiments, a kit comprises a dispensing device such as a syringe or inhaler, that may or may not comprise a composition disclosed herein or a composition described herein. A pack and/or dispenser device can be accompanied by instructions for administration. The pack or dispenser can also be accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert.

In some embodiments a kit or pack comprises an amount of a composition disclosed herein sufficient to treat a patient for 1 day to 1 year, 1 day to 180 days, 1 day to 120 days, 1 day to 90 days, 1 day to 60 days, 1 day to 30 days, 1-24 hours, 1-12 hours, 1-4 hours, or amount of time there between.

A kit optionally includes a product label and/or one or more packaging inserts, that provide a description of the components or instructions for use in vitro, in vivo, or ex vivo, of the components therein. Exemplary instructions may include instructions for a treatment protocol or therapeutic regimen. In certain embodiments, a kit comprises packaging material, which refers to a physical structure housing components of the kit. The packaging material can maintain the components sterilely and can be made of material commonly used for such purposes (e.g., paper, corrugated fiber, glass, plastic, foil, ampules, vials, tubes, etc.). Product labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory-type cards. Product labels or inserts can include identifying information of one or more components therein, dose amounts, clinical pharmacology of the active ingredient(s) including mechanism of action, pharmacokinetics (PK) and pharmacodynamics (PD). Product labels or inserts can include information identifying manufacturer information, lot numbers, manufacturer location, date, information on an indicated condition, disorder, disease or symptom for which a kit component may be used. Product labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. A kit can additionally include labels or instructions for practicing any of the methods described herein. Product labels or inserts can include information on potential adverse side effects and/or warnings.

EXAMPLES

Example 1—An Exemplary Fibrous Collagen Composition

Ingredients:
a) 1 g dried collagen fibers
b) 2.3 g HCl
c) 0.5 g hyaluronic acid (HA) powder
d) 0.1 g Cu or 0.15 g $CuCl_2$ or 0.15 g $CuCl_3$
e) 0.1 g Fe or 0.15 g $FeCl_3$ Collagen fiber (1 g) was added to a 1N HCl solution (2.3 g) and incubated for 14-18 hours with intermittent stirring. The insoluble collagen was pelleted by centrifugation and the supernatant was removed. The damp pellet was resuspended in isopropanol (99-100%) for 60 minutes at 37° C. with intermittent stirring. The partially hydrolyzed collagen was fluffed dry by separating the fiber clumps as much as possible during drying. Drying was finished in a fluidized bed at 45° C. Hyaluronic acid was added and mixed with a vortexer. The iron, or iron salt, was added and mixed, then the copper or copper salt was added and mixed again with a vortexer. The final pH of the dry composition was about 2-3 as measured by litmus paper (pH 0-14 LAB RAM SUPPLIES pH Litmus paper). Additional ingredients can be added as needed to complete each of formulas 1-23 as shown in the tables of FIGS. 35-47. Metals were added at 0.1 g per composition, metal salts at 0.15 g per composition and other ingredients at 0.5 g per composition.

Example 2—An Exemplary Powdered Collagen Composition

Ingredients:
a) 1 g dried collagen fibers
b) 2.3 g HCl
c) 0.5 g hyaluronic acid (HA) powder
d) 0.1 g Cu or 0.15 g $CuCl_2$ or 0.15 g $CuCl_3$
e) 0.1 g Fe or 0.15 g $FeCl_3$ Collagen fiber (1 g) was added to a 1N HCl solution (2.3 g) and incubated for 14-18 hours with intermittent stirring. The insoluble collagen was pelleted by centrifugation and the supernatant was removed. The damp pellet was resuspended in isopropanol (99-100%) for 60 minutes at 37° C. with intermittent stirring. The partially hydrolyzed collagen was fluffed dry by separating the fiber clumps as much as possible during drying. Drying was finished in a fluidized bed at 45° C. The dried fiber was milled to specification (e.g., 20 mesh size fibers instead of fiber clumps) using a 20-mesh screen and an 18-gage needle.

Hyaluronic acid was added to the milled collagen and mixed with a vortexer. The iron, or iron salt, was added and mixed, then the copper or copper salt was added and mixed again with a vortexer. The final pH of the dry composition was about 2-3 as measured by litmus paper (pH 0-14 LAB RAM SUPPLIES pH Litmus paper). Additional ingredients can be added as needed to complete each of formulas 1-23 as shown in the tables of FIGS. 35-47. Metals were added at 0.1 g per composition, metal salts at 0.15 g per composition and other ingredients at 0.5 g per composition.

Example 3—An Exemplary HA Gel Composition

Ingredients:
a) 30 g HA powder
b) 5 g Collagen
c) 0.01 g-0.3 g HCl
d) 473.18 ml water
e) 0.3 g Fe or 0.15 g $FeCl_3$
f) 0.3 g Cu or 0.15 g $CuCl_2$ or 0.15 g $CuCl_3$ All ingredients were added to a laboratory blending dish and mixed. The final pH of the dry composition was about 3-7 as measured by litmus paper (pH 0-14 LAB RAM SUPPLIES pH Litmus paper). Additional ingredients can be added as needed to complete each of formulas 1-23 as shown in the tables of FIGS. 35-47. Metals were added at 0.3 g per composition, metal salts at 0.15 g per composition and other ingredients at 0.5 g per composition.

Example 4—Treatment of Acute Wound (Tooth Extraction Site)

Figure 35:
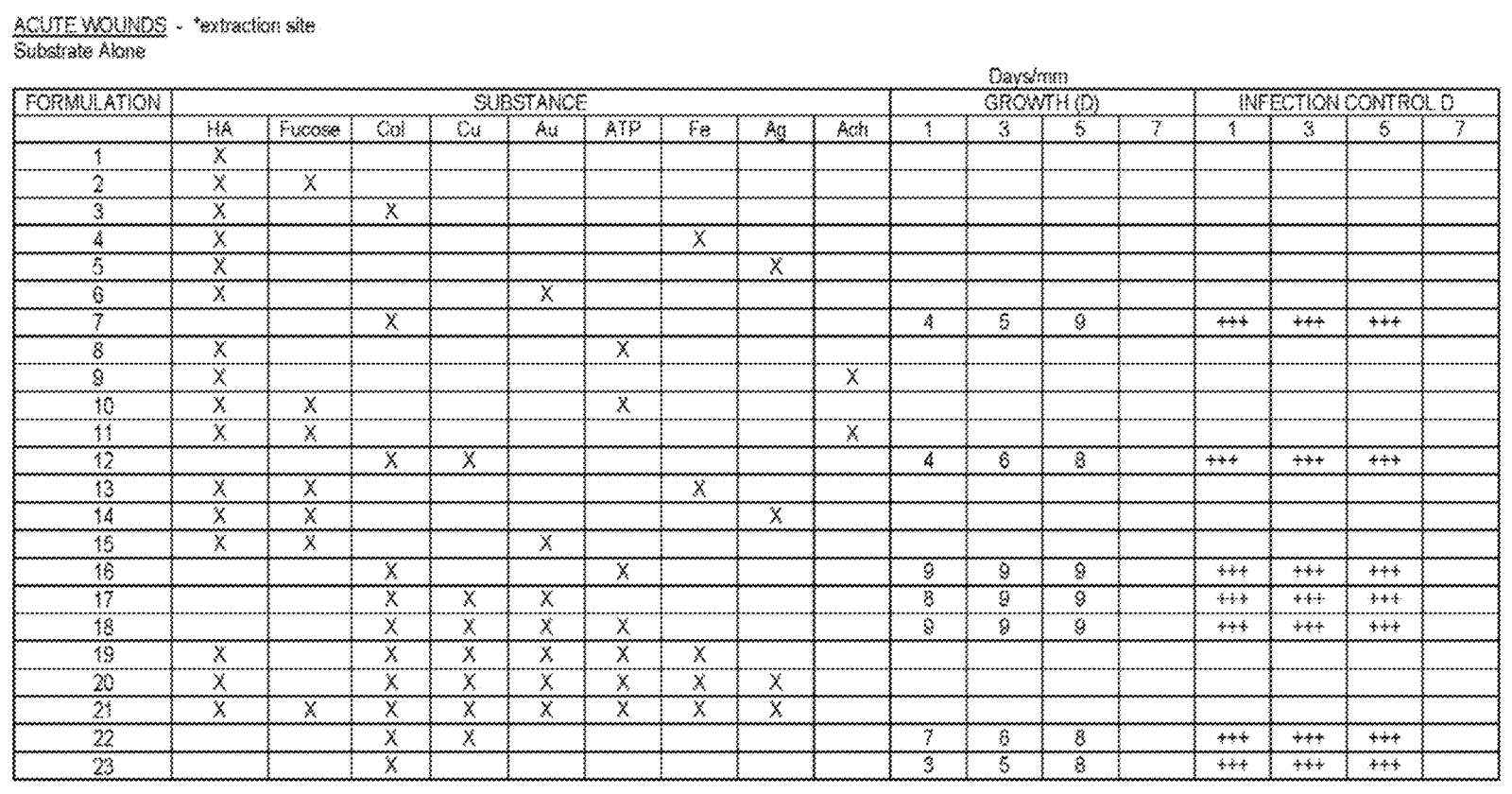

A tip of a laser energy source as described herein was inserted onto the gingiva, just above the periodontal ligament (pdl) of a tooth prior to extraction (1 mm distance from the light source to the pdl). The laser was set at a wavelength of 850 nm. The area was treated by moving the laser circumferentially for 1 minute. The tooth was extracted leaving an extraction site wound of about 4-5 mm in diameter. The extraction site was treated for 1 minute by placing the Evo-lase tip on the extraction site and rotating for 1 minute. A composition (substrate; 0.6 ml) as indicated in the table of FIG. 31 (substrate and laser treatment), formulated as a fibrous mass (Example 1), was placed into the extraction site while disrupting blood clotting. After 1 minute, the extraction site was treated by placing the laser tip over the extraction site (1 mm distance from energy source to extraction site) and rotating for 2 minutes taking care not to disrupt blood clotting. The total treatment time was 4 minutes at 13.2 Joules/cm$^2$ at a wavelength of 850 nm. The compositions and data for tooth extraction sites treated with substrate alone (0.6 ml; no laser treatment), or laser alone are shown in the table of FIGS. 35 & 39, respectively.

Example 5—Treatment of Acute Wound (Head)

A tip of a laser energy source as described herein was placed onto an acute wound of the head (1 mm distance from the light source to the wound) having a diameter of about 3-5 mm. The laser was set at a wavelength of 850 nm. The area was treated by moving the laser circumferentially for 1 minute. A composition (substrate; 0.3-0.6 ml) as indicated in the table of FIG. 41, Formulation 3, formulated as a fibrous mass (Example 1), was placed onto the wound while disrupting blood clotting. The wound was immediately covered with clear tape. After 1 minute, the wound site was treated by placing the energy source tip over the wound site (1 mm distance from energy source to wound site) and rotating for 2 minutes. The total treatment time was 3 minutes at 9.9 Joules/cm$^2$ at a wavelength of 850 nm. The tape was left on until the tissue has grown epithelium. The data for head wound sites treated with substrate alone (0.3-0.6 ml; no laser treatment), or laser and substrate, are shown in the tables of FIGS. 41 and 40 (Formulation 3), respectively. FIG. 41 shows a table of results for the treatment of acute wounds with the substrates of the indicated formulas alone. The row of Formulation #3 provides data for a head wound.

Example 6—Treatment of Acute Wound (Leg)

A tip of a laser energy source as described herein was placed onto an acute wound of the leg (1 mm distance from the wound) having dimensions of about 4 cm×6 cm. The laser was set at a wavelength of 850 nm. The wound area was treated by moving the laser circumferentially for 7 minutes. A composition (substrate; 10 ml) as indicated in table of FIG. 38 (substrate and laser treatment), formulated as a gel, was placed onto the wound. The wound was immediately covered with clear tape. The wound site was treated by placing the tip over the wound site (1 mm distance from energy source to wound site) and rotating for 7 minutes. The total treatment time was 15 minutes at 50 Joules/cm$^2$ at a wavelength of 850 nm. The tape was left on until the next appointment. The data for leg wound sites treated with substrate alone (10 ml; no laser treatment), or laser alone, are shown in table of FIGS. 37 and 39, respectively.

Example 7—Treatment of Diabetic Foot

A tip of a laser energy source as described herein was placed over a dark blue area of a diabetic foot lacking circulation (3 mm distance from the affected area). The laser was set at a wavelength of 850 nm. The affected area was treated for 15 minutes. A composition (substrate; 10 ml) as indicated in the table of FIG. 43 (substrate and laser treatment), formulated as a gel, was placed onto the affected area until the gel absorbed into the tissue. The affected area was again treated with the energy source (3 mm distance from energy source to affected area) for 15 minutes. The total treatment time was 30 minutes at 100 Joules/cm$^2$ at a wavelength of 850 nm. The data for treatment with substrate alone (10 ml; no laser treatment), or laser alone, are shown in the tables of FIGS. 38 (formulation 20) and 39 (formulation 20), respectively. Circulation improvement was detected by a change in color of the affected area from dark blue to pinkish/red after 3 weeks of daily self-administered treatment and the patient described the affected area as feeling warm after treatment.

Example 8—Treatment of Obstructed Circulation

A tip of a laser energy source as described herein was placed over a dark blue area of a leg (1 cm in diameter) having circular obstruction (1 mm distance from the affected area to the light source). The laser was set at a wavelength of 810 nm. The affected area was treated for 15 minutes. A composition (substrate; 5 ml) as indicated in the table of FIG. 43 (Formulation 20) (substrate and laser treatment), formulated as a gel, was placed onto the affected area until the gel absorbs into the tissue. The affected area was again treated with the energy source (1 mm distance from energy source to affected area) for 15 minutes. The total treatment time was 30 minutes at 36 Joules/cm$^2$ at a wavelength of 810 nm. The data for treatment with substrate alone (5 ml; no laser treatment), or laser alone, are shown in the table of FIGS. 41 (formulation 20) and 42 (formulation 20), respectively. Circulation improvement was observed by a change in color of the affected area as the dark blue 1 cm diameter obstruction diminished in color. After 5 treatments, the dark blue obstruction was observed to have disappeared and the tone of the tissue was an even warm pinkish/olive color.

Example 9—Treatment of Tongue and/or Surrounding Tissue (1) Drink 4 oz of diluted Substrate 1, 2, 3, 4, 5 and/or 6.
(2) Wait 15 minutes.
(3) Optionally repeat 1 and/or 2.
(4) Direct RF/laser, RF or laser energy at tongue and/or surrounding tissue of the oral cavity and head/neck region. Keep energy in place for 10-20 minutes or until desired effect is achieved.
(5) Repeat step 4 until desired result is achieved.
(6) Procedure can start at step 1 or step 4.

Non-limiting examples of surrounding tissues include bone, cartilage, muscles, tendons, nerves, blood vessels, epithelium, the like or combinations thereof.

Example 10—Certain Non-Limiting Embodiments

A1. A system for use in tissue generation, comprising:
- (a) providing at least one device comprising a light, radio frequency and/or electric current energy source with at least one opening and/or optionally with at least one opening of a handpiece, fiber, panel, pad, lead and/or current through which the light, radio frequency and/or electric current energy source can emit a beam of light and/or a radio frequency waveform and/or an electric current, further wherein the device is connected to a power source;
- (b) providing at least one substrate and/or portion/s thereof, wherein the at least one substrate and/or portion/s thereof is applied to a tissue;
- (c) contacting the tissue with the beam of light and/or the radio frequency waveform and/or the electron current via the handpiece, wherein the contacting of the tissue occurs before, during or after the at least one substrate and/or portion/s thereof is applied to the tissue, further wherein the at least one device and the at least one substrate and/or portion/s thereof is capable of inducing a biological reaction.

A2. A system for use in repairing tissue subsequent to an acute or chronic injury to an individual, comprising:
- (a) a device comprising a light, radio frequency and/or electric current energy source with at least one opening, through which the light, radio frequency or electric current energy source can emit a beam of light and/or a radio frequency waveform and/or an electric current, further wherein the instrument is connected to a power source;
- (b) at least at least one substrate and/or portion/s thereof, wherein the at least one substrate and/or portion/s thereof is applied to the tissue;
- (c) at least at least one substrate and/or portion/s thereof, wherein the at least one substrate and/or portion/s thereof is applied to the tissue, further wherein optionally the beam of light and/or the radio frequency waveform and/or the electron current is placed over the tissue;
- (d) at least one energy source wherein the beam of light and/or the radio frequency waveform and/or the electron current is placed over the tissue, further wherein optionally the at least one substrate and/or portion/s thereof is applied to the tissue.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

The phrase "induced by", encompasses "worsened by", "aggravated by", "exacerbated by", and/or "magnified by", unless clearly indicated otherwise.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in some embodiments or aspects of the methods disclosed herein, some materials and/or method steps are excluded. Thus, even though the invention is generally not expressed herein in terms of what the invention does not include aspects that are not expressly excluded in the invention are nevertheless disclosed herein.

Some embodiments of the technology described herein suitably can be practiced in the absence of an element not specifically disclosed herein. Accordingly, in some embodiments the term "comprising" or "comprises" can be replaced with "consisting essentially of" or "consisting of" or grammatical variations thereof. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

Further embodiments are described in the following list of clauses:

1. A composition with wound healing and tissue regenerative properties, the composition comprising two or more of, or three or more of: collagen, hyaluronic acid, fucose, copper, and iron.
2. The composition of clause 1, wherein the collagen comprises collagen fibers.
3. The composition of clause 1 or 2, wherein the collagen comprises partially or completely hydrolyzed collagen.
4. The composition of any one of clauses 1 to 3, wherein the collagen is acid treated collagen.
5. The composition of any one of clauses 1 to 4, wherein the copper comprises a copper salt.
6. The composition of clause 5, wherein the copper salt comprises $CuCl_2$ or $CuCl_3$.
7. The composition of any one of clauses 1 to 6, wherein the iron comprises an iron salt.
8. The composition of clause 7, wherein the iron salt comprises $FeCl_3$.
9. The composition of any one of clause 1 to 8, wherein the composition has a pH in a range of 1 to 4, or 2 to 3.
10. The composition of any one of clauses 1 to 9, wherein the composition comprises a water content in a range of 0% to 20%, or 0% to 10%, or 0% to 5% (wt/wt).
11. The composition of any one of clauses 1 to 10, wherein the composition is in the form of a powder, foam, paste, or gel.
12. The composition of any one of clauses 1 to 11, where the percentage of collagen in the composition is a range of 25-70%, 40-60% or 50-60% (wt/wt).
13. The composition of any one of clauses 1 to 11, wherein the percentage of collagen in the composition is about 55-60% (wt/wt).
14. The composition of any one of clauses 1 to 13, wherein the percentage of hyaluronic acid in the composition is in a range of 20-80%, 25-35% or 25-30% (wt/wt).
15. The composition of any one of clauses 1 to 14, wherein the percentage of copper and/or iron in the composition is in a range of 0.1-15%, 1-15%, or 5%-10% (wt/wt).
16. The composition of any one of clauses 1 to 15, wherein the collagen is present in the composition in a range of 50-70% (wt/wt), the hyaluronic acid is present in the composition in a range of 25-35% (wt/wt), the copper is present in the composition in a range of 4-10% (wt/wt) and the iron is present in the composition in a range of 4-10% (wt/wt).
17. The composition of any one of clauses 1 to 16, wherein the composition comprises HCl.
18. The composition of any one of clauses 1 to 17, wherein the percentage of HCL in the composition is in a range of 0.0005-0.5% (wt/wt).
19. The composition of any one of clauses 1 to 8, wherein the composition has a pH in a range of 2 to 3, or 3 to 7.
20. The composition of any one of clauses 1 to 8 and 19, wherein the composition comprises a water content in a range of 75% to 99%, or 85% to 99%, or 90% to 95% (wt/wt).
21. The composition of any one of clause 1 to 8 and 19 to 20, wherein the composition is in the form of a gel, emulsion, slurry or a liquid.
22. The composition of any one of clauses 1 to 8 and 19 to 21, wherein the percentage of collagen in the composition is a range of 0.005-5% or 0.01-1% (wt/wt).
23. The composition of any one of clauses 1 to 8 and 19 to 22, wherein the percentage of collagen in the composition is about 0.1% (wt/wt).
24. The composition of any one of clauses 1 to 8 and 19 to 23, wherein the percentage of hyaluronic acid in the composition is in a range of 0.01-10%, 0.05-5%, or 0.1-1% (wt/wt).
25. The composition of any one of clauses 1 to 8 and 19 to 24, wherein the percentage of copper and/or iron in the composition is in a range of 0.001%-5%, 0.005%-1% or 0.01%-0.1% (wt/wt).
26. The composition of any one of clauses 1 to 8 and 19 to 25, wherein the collagen is present in the composition in a range of 0.01-0.5% (wt/wt), the hyaluronic acid is present in the composition in a range of 0.1-1.5% (wt/wt), the copper is present in the composition in a range of 0.01%-0.1% (wt/wt) and the iron is present in the composition in a range of 0.01%-0.1% (wt/wt).
27. The composition of any one of clauses 1 to 8 and 19 to 26, wherein the composition comprises HCl.
28. The composition of any one of clauses 1 to 8 and 19 to 27, wherein the percentage of HCL in the composition is in a range of 0.0005-0.5% (wt/wt).
29. The composition of any one of clauses 1 to 28, further comprising gold or a salt thereof.
30. The composition of clause 29, wherein the gold comprises gold particles or gold nanoparticles.
31. The composition of clause 29 or 30, wherein the percentage of gold in the composition is in a range of 0.001%-10%, 0.001%-5%, or 0.01%-0.1% (wt/wt).
32. The composition of any one of clauses 1 to 31, further comprising silver or a salt thereof.
33. The composition of clause 32, wherein the percentage of silver in the composition is in a range of 0.001%-10%, 0.001%-5%, or 0.01%-0.1% (wt/wt).
34. The composition of any one of clauses 1 to 33, further comprising Fucose.
35. The composition of clause 34, wherein the percentage of Fucose in the composition is in a range of 0.01%-30%, 0.05%-15%, 0.05% to 2% or 20-25% (wt/wt).
36. The composition of any one of clauses 1 to 35, further comprising adenosine triphosphate.
37. The composition of clause 36, wherein the percentage of adenosine triphosphate in the composition is in a range of 0.01%-30%, 0.05%-15%, 0.05% to 2% or 20-25% (wt/wt).

38. The composition of any one of clauses 1 to 37, further comprising acetylcholine.
39. The composition of clause 38, wherein the percentage of acetylcholine in the composition is in a range of 0.01%-30%, 0.05%-15%, 0.05% to 2% or 20-25% (wt/wt).
40. The composition of any one of clauses 1 to 39 wherein the composition comprises collagen and copper.
41. The composition of any one of clauses 1 to 40 wherein the composition comprises collagen and iron.
42. The composition of any one of clauses 1 to 41 wherein the composition comprises collagen, copper and iron.
43. The composition of any one of clauses 1 to 42, wherein the composition comprises hyaluronic acid and copper.
44. The composition of any one of clauses 1 to 43, wherein the composition comprises hyaluronic acid and iron.
45. The composition of any one of clauses 1 to 44, wherein the composition comprises hyaluronic acid, iron and copper.
46. The composition of any one of clauses 1 to 45 wherein the composition comprises hyaluronic acid and fucose.
47. The composition of any one of clauses 1 to 46, further comprising fucose and/or silver.
48. The composition of any one of clauses 1 to 47, further comprising gold.
49. The composition of any one of clauses 1 to 47, further comprising ATP and/or acetylcholine.
50. The composition of any one of clauses 1 to 49, wherein the composition is formulated as a pharmaceutical composition.
51. The composition of any one of clauses 1 to 50, wherein the pharmaceutical composition is formulated as a tablet, capsule, emulsion, powder, gel, paste, liquid, or spray,
52. The composition of any one of clauses 1 to 51, wherein the pharmaceutical composition is formulated for delivery by an inhaler.
53. A kit comprising the composition or pharmaceutical composition of any one of clauses 1 to 52.
54. The composition, pharmaceutical composition or kit of any one of clauses 1 to 53 for use in treating a wound in a subject, inducing tissue regeneration in a subject, or improving circulation in a tissue of a subject.
55. A method of treating a wound or tissue damage in a subject comprising administering a therapeutically effective amount of the composition of any one of clauses 1 to 52 to the subject.
56. A method of inducing tissue regeneration in a subject comprising administering a therapeutically effective amount of the composition of any one of clauses 1 to 52 to a wound of the subject.
57. A method of improving circulation in a subject comprising administering a therapeutically effective amount of the composition of any one of clauses 1 to 52 to a tissue of the subject.
58. The method of any one of clauses 55 to 57, further comprising administering a therapeutically effective amount of energy to the wound or damaged tissue of the subject.
59. The method of clause 58, wherein the energy comprises a wavelength in a range of 350 nm to 1400 nm.
60. The method of clause 59, wherein the energy comprises a wavelength in the range of 700-900 nm.
61. The method of any one of clauses 58 to 60, wherein the therapeutically effective amount of energy comprises a dose of 1 to 400 joules/cm$^2$ or 10 to 100 joules/cm$^2$.
62. The method of clause 61, wherein the dose is delivered to the wound or tissue for 1 to 30 minutes.
63. The method of any one of clauses 58 to 62, wherein the therapeutically effective amount of energy is administered 1 to 20 times.
64. The method of any one of clauses 58 to 63, wherein the energy is administered before and/or after administration of the composition.
65. The method of any one of clauses 58 to 64, wherein the composition is administered by local or systemic administration; by topical, oral, sublingual, parenteral, intranasal or intratracheal administration; or by inhalation.
66. The method of any one of clauses 58 to 65, wherein the therapeutically effective amount of the composition comprises a volume in a range of 0.1 to 20 ml, or 0.1 to 10 ml.
67. The method of any one of clauses 58 to 66, wherein the therapeutically effective amount of the composition comprises a dose of 0.1 to 50 mg/kg of body weight of the subject when administered systemically.
68. The method of any one of clauses 58 to 67, wherein the therapeutically effective amount of the composition comprises a dose of 0.1 mg/cm$^2$ to 1 gram/cm$^2$ when administered locally or topically.
69. The method of any one of clauses 58 to 68, wherein the wound is an acute wound or a chronic wound.
70. The method of clause 69, wherein the acute wound is a surgical incision.
71. The method of clause 69, wherein the acute wound is a tooth extraction site.
72. The method of clause 69, wherein the chronic wound is an ulcer.
73. The method of any one of clauses 58 to 68, wherein the tissue is hypoxic, ischemic, lacks sufficient circulation, is restricted of blood flow and/or comprises a vasculature obstruction.
74. The method of any one of clauses 58 to 68, wherein the subject is diabetic.
75. A system configured to be used to treat and/or generate tissue, the system comprising:
    a device configured to generate one or more types of therapeutic energy for provision to the tissue, the one or more types of therapeutic energy comprising one or more of laser radiation, radio frequency (RF) waves, audio frequency waves, or light from a light emitting diode (LED); and
    a composition with wound healing and/or tissue regenerative properties, the composition comprising two or more of, or three or more of: collagen, hyaluronic acid, fucose, copper, and iron.
76. The system of clause 75, wherein the collagen is present in the composition in a range of 0.01-0.5% (wt/wt), the hyaluronic acid is present in the composition in a range of 0.1-1.5% (wt/wt), the copper is present in the composition in a range of 0.01%-0.1% (wt/wt) and the iron is present in the composition in a range of 0.01%-0.1% (wt/wt).
77. The system of clause 75, wherein the device comprises a laser configured to generate the laser radiation, the laser comprising one or more individual fibers configured to conduct the laser radiation, the laser radiation having a power of about 0.1-5 W per fiber.

78. The system of clause 75, wherein the one or more types of therapeutic energy have a wavelength of about 200 nm to about 2500 nm.
79. The system of clause 75, wherein the device comprises an LED configured to generate light comprising photons configured to be received by the tissue, the LED arranged on a board with a plurality of other LEDs configured to generate the same and/or similar light.
80. The system of clause 75, wherein the device comprises an RF and/or an audio frequency function generator, the RF and/or audio frequency comprising a frequency of about 100 Hz-4 MHz.
81. A device configured to generate one or more types of therapeutic energy for provision to tissue, the device comprising:
one or more energy sources configured to generate one or more types of therapeutic energy, the one or more types of therapeutic energy comprising one or more of laser radiation, radio frequency (RF) waves, audio frequency waves, or light from a light emitting diode (LED), wherein the one or more types of therapeutic energy have a wavelength of about 200 nm to about 2500 nm and/or frequency of 1-2.4 GHz.
82. The device of clause 81, wherein the device comprises a laser configured to generate the laser radiation, the laser comprising one or more individual fibers configured to conduct the laser radiation, the laser radiation having a power of about 0.1 to about 5 W per fiber, wherein the laser radiation is not pulsed.
83. The device of clause 81, wherein the device comprises an LED configured to generate light comprising photons configured to be received by the tissue, the LED arranged on a board with a plurality of other LEDs configured to generate the same and/or similar light.
84. The device of clause 81, wherein the device comprises an RF and/or an audio frequency function generator, the RF and/or audio frequency comprising a frequency of about 100 Hz-4 MHz.
85. The device of clause 81, wherein the one or more energy sources comprise two or more of, or three or more of a laser, an LED, an RF frequency function generator, and an audio frequency function generator.
86. A method for generating one or more types of therapeutic energy for provision to tissue, the device comprising:
generating, with one or more energy sources, one or more types of therapeutic energy, the one or more types of therapeutic energy comprising one or more of laser radiation, radio frequency (RF) waves, audio frequency waves, or light from a light emitting diode (LED), wherein the one or more types of therapeutic energy have a wavelength of about 200 nm to about 2500 nm; and
directing the one or more types of therapeutic energy toward the tissue.
87. The method of clause 86, wherein the generating comprises generating laser radiation with a laser, the laser comprising one or more individual fibers configured to conduct the laser radiation, the laser radiation having a power of about 0.1-5 W per fiber, and wherein the laser radiation is not pulsed.
88. The method of clause 86, wherein the generating comprises generating light with an LED, the light comprising photons configured to be received by the tissue, the LED arranged on a board with a plurality of other LEDs configured to generate the same and/or similar light.
89. The method of clause 86, wherein the generating comprises generating RF and/or audio frequency energy with an RF and/or an audio frequency function generator, the RF and/or audio frequency comprising a frequency of about 100 Hz-4 MHz.
90. The method of clause 86, wherein the generating comprises generating two or more, or three or more, of the types of therapeutic energy and directing the two or more, or three or more, types of therapeutic energy toward the tissue.
91. A device for imaging tissue, comprising:
one or more light emitting diodes (LED) configured to emit light for illuminating the tissue, the light have a wavelength of about 790-860 nm (IR), and a power of about 0.5-10 W per LED, and
a camera configured to obtain images of the illuminated tissue;
wherein the one or more LEDs and the camera are configured to be moved back and forth over the tissue such that the camera acquires a plurality of images during the movement.
92. The device of clause 91, wherein the one or more LEDs are configured to emit light in the green wavelength range of the visible spectrum or the infrared wavelength range.
93. The device of clause 91, further comprising one or more processors configured to analyze images obtained by the camera by combining individual images into a common image, and identifying anatomical features in the tissue based on the common image.
94. The device of clause 91, further comprising a handle or a stand coupled to the one or more LEDs and the camera, the handle or the stand configured to be manipulated by a user such that the light from the one or more LEDs is directed at the tissue.
95. The device of clause 91, further comprising a display screen and a keyboard configured to facilitate entry or selection of information configured to control the imaging device.
96. The device of clause 91, wherein one or more veins in tissues are located using the plurality of images.
97. The device of clause 91, wherein reflected light from the tissue is captured by the camera.
98. The device of clause 91, wherein the one or more processors are formed by a raspberry pi computing module.

I claim:
1. A composition with wound healing and tissue regenerative properties, the composition comprising:
a. collagen
b. hyaluronic acid
c. copper chloride or nano particle copper,
d. iron chloride or nano particle iron,
f. silver, and
e. gold
wherein the collagen is present in the composition in a range of 0.01-0.5% (wt/wt), the hyaluronic acid is present in the composition in a range of 0.1-1.5% (wt/wt), the copper chloride or nano particle copper is present in the composition in a range of 0.00001%-15% (wt/wt), the iron chloride or nano particle iron is present in the composition in a range of 0.00001%-15% (wt/wt), the silver is present in the composition in a range of 0.00001%-15% (wt/wt), and the gold is present in the composition in a range of 0.00001%-15% (wt/wt).

2. The composition of claim 1, wherein the collagen comprises collagen fibers.

3. The composition of claim 1, wherein the collagen comprises partially or completely hydrolyzed collagen.

4. The composition of claim 1, wherein the collagen is acid treated collagen.

5. The composition of claim 1, wherein the composition has a pH in a range of 1-8, 1 to 4, or 2 to 3.

6. The composition of claim 1, wherein the composition comprises a water content in a range of 0 to 90%, 0% to 20%, or 0% to 10%, or 0% to 5% (wt/wt).

7. The composition of claim 1, wherein a ratio of the hyaluronic acid to the silver is about 10-50,000 to 1.

8. The composition of claim 1, wherein the silver comprises silver chloride or nano particle silver.

9. A composition with wound healing and tissue regenerative properties, the composition comprising:
   a. collagen
   b. hyaluronic acid
   c. copper,
   d. iron, and
   f. silver
   wherein the collagen is present in the composition in a range of 0.01-0.5% (wt/wt), the hyaluronic acid is present in the composition in a range of 0.1-1.5% (wt/wt), the copper is present in the composition in a range of 0.01%-0.1% (wt/wt) and the iron is present in the composition in a range of 0.01%-0.1% (wt/wt).

10. A composition with wound healing and tissue regenerative properties, the composition comprising:
   a. collagen
   b. hyaluronic acid
   c. copper,
   d. iron, and
   e. silver,
   wherein the collagen is present in the composition in a range of 0.01-0.5% (wt/wt), the hyaluronic acid is present in the composition in a range of 0.1-1.5% (wt/wt), the copper is present in the composition in a range of 0.00001%-15% (wt/wt), the iron is present in the composition in a range of 0.00001%-15% (wt/wt), and the silver is present in the composition in a range of 0.00001%-15% (wt/wt).

* * * * *